United States Patent
Luyt et al.

(10) Patent No.: US 11,186,571 B2
(45) Date of Patent: Nov. 30, 2021

(54) QUINAZOLINONE DERIVATIVES USEFUL FOR IMAGING

(71) Applicant: LONDON HEALTH SCIENCES CENTRE RESEARCH INC., London (CA)

(72) Inventors: Leonard Luyt, London (CA); Jinqiang Hou, Thunder Bay (CA)

(73) Assignee: LONDON HEALTH SCIENCES CENTRE RESEARCH INC., London (CA)

( * ) Notice: Subject to any disclaimer, the term of this patent is extended or adjusted under 35 U.S.C. 154(b) by 0 days.

(21) Appl. No.: 16/500,867

(22) PCT Filed: Apr. 6, 2018

(86) PCT No.: PCT/CA2018/050425
§ 371 (c)(1),
(2) Date: Oct. 4, 2019

(87) PCT Pub. No.: WO2018/184115
PCT Pub. Date: Oct. 11, 2018

(65) Prior Publication Data
US 2020/0031821 A1    Jan. 30, 2020

Related U.S. Application Data

(60) Provisional application No. 62/482,467, filed on Apr. 6, 2017.

(51) Int. Cl.
*C07D 417/14* (2006.01)
*C07D 401/06* (2006.01)

(52) U.S. Cl.
CPC ......... *C07D 417/14* (2013.01); *C07D 401/06* (2013.01)

(58) Field of Classification Search
CPC .................................................. C07D 417/14
See application file for complete search history.

(56) References Cited

FOREIGN PATENT DOCUMENTS

WO      2006012577        2/2006
WO      WO2006/012577  *  2/2006  ........... C07D 413/12

OTHER PUBLICATIONS

Potter et al., Bioorganic & Medicinal Chemistry (2011), 19(7), 2368-2372.*
Rudolph et al., Journal of Medicinal Chemistry (2007), 50(21), 5202-5216.*
Jeffery, P L, et al., Expression and action of the growth hormone releasing peptide ghrelin and its receptor in prostate cancer cell lines, Journal of Endocrinology (2002) 172, R7-R11.
Tovmassian, D., et al., The Role of [18F]FDG-PET/CT in Predicting Malignant Transformation of Plexiform Neurofibromas in Neurofibromatosis-1, International Journal of Surgical Oncology, vol. 2016, Article ID 6162182, pp. 1-7.
Lu, C., et al., Ghrelin Receptor as a Novel ImagingTarget for Prostatic Neoplasms. The Prostate 72:825-833 (2012).
Douglas, G.A.F., et al.. Characterization of a far-red analog of ghrelin for imaging GHS-R inP19-derived cardiomyocytes. Peptides 54 (2014) 81-88.
Rudolph, J., et al., Quinazolinone Derivatives as Orally Available Ghrelin Receptor Antagonists for the Treatment of Diabetes and Obesity, J. Med. Chem. 2007, 50, 5202-5216.
Esler, W.P., et al., Small-Molecule Ghrelin Receptor Antagonists Improve Glucose Tolerance, Suppress Appetite, and Promote Weight Loss, Endocrinology 148(11):5175-5185.
Hanrahan, P., et al., Substituted azaquinazolinones as modulators of GHSr-1a for the treatment of type II diabetes and obesity, Bioorg. Med. Chem Lett. 22 (2012) 2271-2278.
Potter, R., et al., Synthesis and in vivo evaluation of (S)-6-(4 fluorophenoxy)-3-((1 [11C]methylpiperidin-3-yl)methyl)-2-o-tolylquinazolin-4(3H)-one, a potential PET tracer for growth hormone secretagogue receptor (GHSR), Bioorg. Med. Chem. 19 (2011) 2368-2372.
Vodnik, M., et al., Ghrelin Receptor Ligands Reaching Clinical Trials: From Peptides to Peptidomimetics; from Agonists to Antagonists, Horm Metab Res 2016; 48: 1-15.
Nikolopoulos, D., et al., Ghrelin: A potential therapeutic target for cancer, Regulatory Peptides 163 (2010) 7-17.
Written Opinion of the International Searching Authority, PCT/CA2018/050425, dated Jul. 5, 2018.

* cited by examiner

*Primary Examiner* — Paul V Ward
(74) *Attorney, Agent, or Firm* — Eduardo Krupnik

(57) ABSTRACT

Compounds comprising quinazolinone derivatives and methods of identification and use of imaging agents. The compounds have the general formula I: wherein R2 is selected from halogen, halosubstituted alkyl, alkyl, hydroxyl-alkyl, and amino-alkyl; X is selected from ester, carbonyl or —CH2—; R1 is selected from mono-, or bicyclic aromatic or heteroaromatic ring systems, wherein the mono-, or bicyclic aromatic or heteroaromatic ring systems are optionally substituted by halo, alkyl, nitro, alkoxy, amino; R3 is selected from one or two halo, halosubstituted alkyl, alkyl, nitro, hydroxyl-alkyl, and alkyl tosylate; or a pharmaceutically acceptable salt thereof. The compounds of the present invention may be used for detection, diagnosis and/or staging of prostate or other forms of cancer, and may also be used for cardiac disease.

19 Claims, 28 Drawing Sheets

QUINAZOLINONE DERIVATIVES USEFUL FOR IMAGING

CROSS REFERENCE TO RELATED APPLICATIONS

This application is a national stage application under 35 U.S.C. 371 of International Application No. PCT/CA2018/050425, filed Apr 6, 2018, which in turn claims the benefit under 35 U.S.C. 119(e) of U.S. Provisional Ser. No. 62/482,467, filed Apr. 6, 2017, the contents of each of which are hereby incorporated by reference into the present disclosure.

FIELD OF THE INVENTION

The present invention relates to small molecules with enhanced affinity to the growth hormone secretagogue receptor 1a (GHS-R1a) relative to the endogenous ligand for GHS-R1a and their uses in imaging the ghrelin receptor, cancer cells and cardiomyocytes.

BACKGROUND OF THE INVENTION

Growth hormone releasing peptides (GHRPs) belong to a class of compounds known as growth hormone secretagogues. These are compounds that are specifically defined as molecules that stimulate the secretion of pituitary GH through a route different from that of GH releasing hormone (GHRH).

The endogenous ligand for the GHS-R1a was isolated from the rat stomach by Kojima and co-workers, thereby completing the cycle of reverse pharmacology. This ligand, termed "ghrelin" is a 28 amino acid peptide with an n-octanoyl group on the Ser 3 side-chain that is important for binding to the GHS-R1a and releasing GH in vivo. In addition, this acylation is also responsible for ghrelin's numerous biological activities, such as regulation of glucose metabolism, insulin release, gut motility and many others. Since ghrelin is the endogenous ligand for the GHS-R1a, this receptor is also referred to as the ghrelin receptor.

Other than treating GH deficiency, GHS-R1a agonists could also be developed for treating a variety of disorders such as anorexia nervosa and heart failure. Additionally, the GHS-R1a was recently found to be expressed in a number of prostate cancer cell lines such as ALVA-41, LNCaP, DU145 and PC3.[1] Development of GHS-R1a agonists that specifically target prostate cancer cells could provide a means to detect and visualize prostatic tumours in vivo through the use of a suitable imaging modality. This would enable an alternative means to image prostate cancer (PCa).

Prostate cancer (PCa) is the foremost male malignancy in North America. Clinical methods currently used to diagnose PCa involve a combination of the digital rectal examination (DRE), the serum prostate-specific antigen (PSA) test and transrectal ultrasound (TRUS)-guided biopsy. These methods are not only used to predict the recurrence of tumours after radical prostatectomy and the potential for cancer to spread from the prostate, but also to divide patients into groups based on the risk of PCa reappearance after localized treatment. Despite the utility that these techniques provide, the presence of sampling error in TRUS-guided biopsies coupled with patients who have consistently elevated levels of serum PSA in spite of negative prostate biopsies, suggests that developing non-invasive imaging methods that improve disease identification at an earlier phase of illness is crucial.

One such non-invasive technique for PCa diagnosis and staging is a combination of magnetic resonance imaging (MRI) and functional MRI methods such as diffusion-weighted MRI (DW-MRI), magnetic resonance spectroscopic imaging (MRSI) and dynamic contrast-enhanced MRI (DCE-MRI). Briefly, these methodologies collect information on in vivo diffusion coefficients for biological tissues, metabolism and tissue vascularity respectively. The combination of T2-weighted MRI and two or more functional techniques make up the multi-parametric prostate MRI (mpMRI) exam, which is currently a highly effective way to identify and localize PCa. Despite the usefulness of the data gathered by functional MRI, it tends to suffer from difficult and lengthy procedures (MRSI), limited lesion detection in the central gland, the requirement for dedicated computer software for data analysis (DCE-MRI) and the inability to specify cut-off values in apparent diffusion coefficients (ADC) in DW-MRI thus making the delineation between benign and malignant tumours problematic.

In addition to these factors, there are currently no guidelines available that can specify which functional sequence is most appropriate in a particular clinical scenario.

Alternative imaging methods for diagnosing and staging PCa include computed tomography (CT) and positron emission tomography (PET). These two techniques are often used in tandem. Unfortunately, much like in the case of MRI, a number of limitations exist. The former imaging modality alone is unable to distinguish between benign and malignant prostatic tissue, [thereby restricting its use in detecting primary prostate cancer. A combination of PET/CT using the radiotracer $^{18}$F-FDG enables tumour localization via the Warburg effect but suffers from renal excretion, thus masking possible prostatic tumours due to build-up of activity in the bladder.[2] In addition to this, PET has a limited ability to distinguish between benign and malignant disease, despite the use of alternative radiotracers such as [$^{18}$F]fluorodihydrotestosterone (FDHT), [$^{11}$C]acetate, [$^{11}$C]Choline, and [$^{11}$C]methionine. It is therefore clear that the development of novel imaging techniques to improve differentiation between benign and malignant prostatic tumours, as well as addressing the clinical issue of over-diagnosing prostate cancer and thus over-treating potentially benign tumours is of paramount importance. The GHS-R1a is known to have differential expression in breast carcinomas, ovarian tumours as well as in normal, benign and cancerous prostatic tissue.[3] Previous work within the Luyt group has shown that targeting the GHS-R1a expressed in PCa cell lines may enable non-invasive radionuclide imaging of prostate cancer.[3] This was indicated by the specificity of the peptidic imaging probe fluorescein-ghrelin(1-19) towards PCa, with low level association in benign prostatic hyperplasia (BPH) or normal prostatic tissue.[3]

In cardiomyocytes, ghrelin regulates signaling pathways that link to myocardial metabolism and cardiomyocyte growth and survival, thus indicating that ghrelin may play a vital role in the progression of cardiomyopathy. Recent efforts in collaboration with Dr. Savita Dhanvantari have also identified GHSR as a marker related to cardiovascular disease.[4] Quinazolinone derivatives were initially developed by Bayer Pharmaceuticals for the treatment of diabetes and obesity (FIG. 1A).[5, 6] Extensive structural modifications were performed and structure activity relationship investigation demonstrated that, (1) piperidine substituent is essential for the binding affinity, (2) decreasing the size of the $R_3$ substituent gradually weaken binding affinity, (3) a bulky group in $R_1$ position is essential for activity, (4) alkyl groups in the $R_2$ position affect the functional profiles of the small molecules, (5) (S)-stereoisomers are significantly more potent than the (R)-isomers. The most potent compound synthesized from their work (FIG. 1B) has an $IC_{50}$ of 0.9 nM (3.7 nM determined in our lab, which is equivalent to that of natural ghrelin). However, the compound maybe too lipophilic (cLogP$_{7.4}$=3.32) to be a promising oral drug candidate for the treatment of diabetes. Another group Hanrahan et al. focused on the modification of the lipophilicity of the central core by changing the quinazolinone type structure to the aza-quinazolinone type structures as exemplified in FIG. 1C.[7] The SAR suggested that adding one or two nitrogen to the quinazolinone core at any position (1, 2 or 3 in FIG. 1C) decreased the potency, while modification on substituents provide good chances to improve the potency. Dr. Andrew G. Horti from Johns Hopkins Medicine reported a $^{11}C$ radio labeled quinazolinone derivative (Ki=22 nM, cLogD=2.89) for PET imaging of GHSR in mice.[8] The studies suggested that, to image GHS-R1a, the compound should have much stronger binding affinity and moderate lipophilicity.[8]

SUMMARY OF THE INVENTION

The present invention discloses quinazolinone derivatives that have enhanced affinity for the growth hormone secretatogue receptor 1a (GHS-R1a) relative to naturally occurring ghrelin, and moderate lipophilicity. The small molecules of the present invention, in another embodiment, include a label that confers upon them the ability to non-invasively image using positron emission tomography (PET). The quinazolinone derivatives targeting GHS-R1a can be used as a clinical tool for accurate cancer diagnosis, including prostate cancer, breast cancer, ovarian cancer and any other condition or disease where GHS-R1a is highly expressed, such as cardiovascular disease.

The present invention provides for compounds having stronger binding affinity than natural ghrelin and moderate lipophilicity with a cLogD ranging from 1-3. In one embodiment of the present invention, the compounds exhibits sub-nanomolar $IC_{50}$ (0.02 nM) and cLogD of 2.39.

Generally, the present disclosure relates to compounds, which can be described as quinazolinone derivatives that can be useful as radiotracers for positron emission tomography (PET).

The compounds of the present invention have binding affinity to the GHS-R1a. Accordingly, the present disclosure also relates to a method of detecting ghrelin receptors in a subject. Given that the differential expression of GHS-R1a in carcinomas such as breast, ovarian and prostatic carcinomas, also disclosed are methods of diagnosing carcinomas using the quinazolinone derivative compounds of the present invention.

Also disclosed herein are compositions, dosage forms, methods, uses, commercial packages and kits relating to the compounds of the present invention.

In one aspect, there is provided a compound having the general formula I:

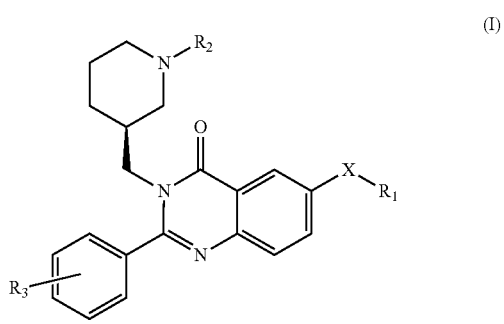

wherein $R_2$ is halogen, halosubstituted alkyl, alkyl, hydroxyl-alkyl, amino-alkyl;

X is ester, carbonyl or —CH$_2$—;

$R_1$ is mono-, or bicyclic aromatic or heroaromatic ring systems, optionally substituted by halo, alkyl, nitro, alkoxy, amino;

$R_3$ is one or two halo, halosubstituted alkyl, alkyl, nitro, hydroxyl-alkyl, alkyl tosylate;

and to pharmaceutically acceptable salts.

In one embodiment of the present invention, halo and halosubstituted includes substitution with F, Br, or I.

In some embodiments, the halogen is F, Br or I.

In some embodiments, the compound of the present invention includes a detectable label selected from $^{18}F$, $^{76}Br$, $^{123}I$, $^{125}I$, and $^{131}I$.

In some embodiments, the compound of the present invention is conjugated to other molecular entities or nanoparticles.

In some embodiments, Ri is selected from the group consisting of:

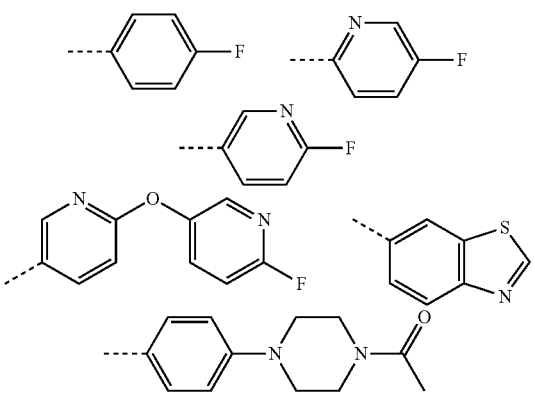

In some embodiments R2 is selected from the group consisting of:

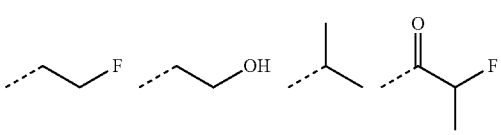

In some embodiments R₃ is selected from the group consisting of:

Methyl

Fluorine

[Structures of fluoroethoxy and hydroxyethoxy groups]

In some embodiments R₁ is selected from the group consisting of:

[Structures of 5-fluoropyridin-2-yl and benzothiazol-6-yl groups]

In some embodiments, R₂ is selected from the group consisting of:

[Structures of isopropyl, sec-butyl, and 2-fluoroethyl groups]

In some embodiments, the compound of the present invention is selected from the group consisting of:

5i

[Chemical structure]

5g

[Chemical structure]

10b

[Chemical structure]

15b

[Chemical structure]

19

[Chemical structure]

20

[Chemical structure]

or a pharmaceutical acceptable salt thereof.

In some embodiments, the compound of the present invention is selected from the group consisting of:

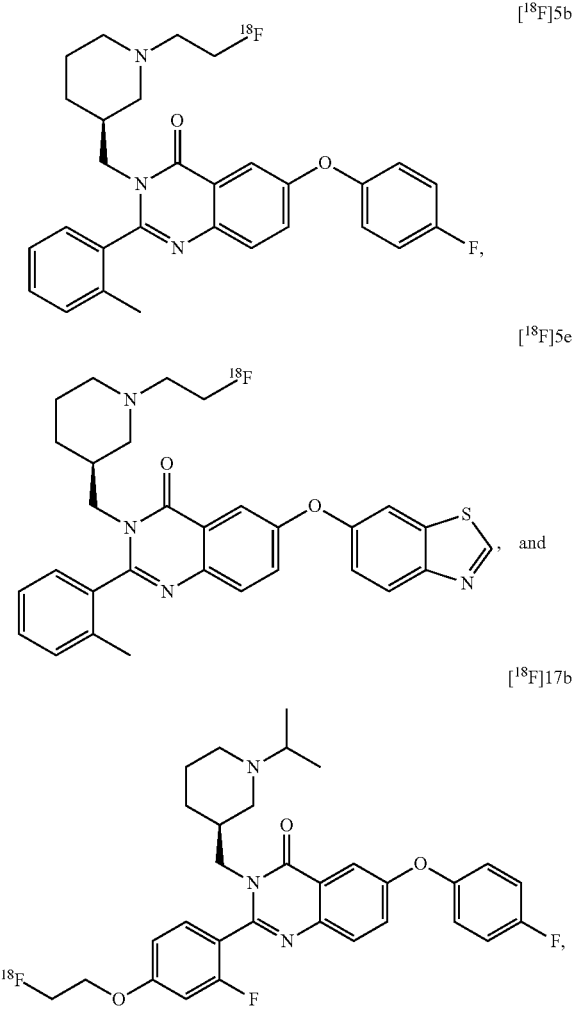

or a pharmaceutical acceptable salt thereof.

In another embodiment, the compound of the present invention is conjugated to other molecular entities or nanoparticles.

In another embodiment, the compound of the present invention is conjugated to or incorporated within a nanoparticle.

In another embodiment, the compound of the present invention the nanoparticle is selected from a group comprising: gold nanoparticles, dendrimers, iron oxide particles, liposomes, protein nanoparticles, or other polymeric nanoparticles.

In another embodiment, the compound of the present invention the compound is conjugated to a cytotoxic molecule.

In another embodiment, the compound of the present invention the cytotoxic molecule is selected from a group comprising: anthracyclins, taxanes, nucleotide analogues, platinum complexes, and kinase inhibitors.

In another embodiment, the present invention relates to a method of detecting ghrelin receptors at a target site of a subject, the method including: (a) providing a quinazolinone derivative of the present invention having a detectable label, such as $^{18}F$, $^{76}Br$, $^{123}I$, $^{125}I$, or $^{131}I$ and having enhanced affinity for GHS-R1a relative to natural ghrelin and moderate lipophilicity; (b) administering the derivative of step (a) to the subject in an amount effective to detect the growth hormone receptors at the target site; (c) allowing the quinazolinone derivative to accumulate at the target site within the subject; and (d) detecting the quinazolinone derivative having the label at the target site thereby detecting the GHS-R1a at the target site.

In one embodiment of the method of detecting ghrelin receptors at a target site of a subject, the target site is a tumor or cardiac tissue.

In one embodiment of the method of detecting ghrelin receptors at a target site of a subject, the detecting is performed with positron emission tomography (PET), PET-computed tomography (CT) hybrid or PET-magnetic resonance imaging (MRI) hybrid.

In another embodiment, the present invention relates to a method of assessing the malignancy of a tumor, the method including: (a) contacting the tumor with a quinazolinone derivative of the present invention labeled with $^{18}F$, $^{76}Br$, $^{123}I$, $^{125}I$, or $^{131}I$, (b) detecting the expression of the quinazolinone derivative with the label in the tumor, (c) comparing the expression of step (b) with the expression of said quinazolinone derivative with the label in a control tissue, and (d) assessing the malignancy of the tumor based on the comparison. In aspects, the detecting is performed with positron emission tomography (PET), PET-computed tomography (CT) hybrid or PET-magnetic resonance imaging (MRI) hybrid.

In another embodiment, the present invention is a use of the quinazolinone derivative with $^{18}F$, $^{76}Br$, $^{123}I$, $^{125}I$, or $^{131}I$ according to any one of the previous embodiments for imaging cancer cells and cardiac tissue in vivo, ex vivo or in vitro.

In another embodiment, the present invention is a use of the quinazolinone derivative according to any one of the previous embodiments for the treatment of GH deficiency, stimulate GH secretion from the pituitary, increase appetite, attenuate cachexia in patient with cancer or chronic obstructive pulmonary disease, suppressing ghrelin's orexigenic effects, treating obesity, regulating food intake, GI motility, gastric emptying, body weight, and treating ulcer or gastroparesis, treating anorexia nervosa, heart failure, diabetes mellitus (including Type 1 and 2) or diabetes mellitus complications, constipation and Parkinson's disease.

In another embodiment the present invention is a method of treating a disorder associated with the regulation of ghrelin receptor, the method including administering to a subject in need, an effective amount of a quinazolinone derivative of the present invention. In aspects, the disorder is selected from GH deficiency, cachexia in patient with cancer or chronic obstructive pulmonary disease, obesity, GI motility, gastric emptying, ulcer or gastroparesis, anorexia nervosa, heart failure, diabetes mellitus (including Type 1 and 2) or diabetes mellitus complications, constipation and Parkinson's disease.

In another embodiment, the present invention is a quinazolinone derivative as defined in any one of previous embodiments for use in imaging GHS-R1a.

In another embodiment, the present invention is a quinazolinone derivative as defined in any one of the previous embodiments for use in imaging GHS-R1a.

In another embodiment, the present invention is a quinazolinone derivative as defined in any one of the previous embodiments for use in imaging, diagnosing or staging cancer, and heart disease.

In another embodiment, the present invention is a pharmaceutical composition comprising a quinazolinone derivative as defined in any of the previous embodiments, and a pharmaceutically acceptable carrier.

In another embodiment, the present invention is a method of increasing the level of endogenous growth hormone in a subject comprising administering to the subject a pharmaceutically effective amount of a pharmaceutical composition according to any of the previous embodiments.

In another embodiment, the present invention is a method for treating a subject of a ghrelin receptor related disorder or condition, the method including administering to the subject a pharmaceutically effective amount of the pharmaceutical composition of the present invention, wherein the disorder or condition is selected from increase appetite, attenuate cachexia in patient with cancer or chronic obstructive pulmonary disease, suppressing ghrelin's orexigenic effects, treating obesity, regulating food intake, GI motility, gastric emptying, body weight, and treating ulcer or gastroparesis, treating anorexia nervosa, heart failure, diabetes mellitus (including Type 1 and 2) or diabetes mellitus complications, constipation and Parkinson's disease.

BRIEF DESCRIPTION OF THE DRAWINGS

The following figures illustrate various aspects and preferred and alternative embodiments of the invention.

DESCRIPTION OF THE INVENTION

Definitions and Abbreviations

Figure 1A:
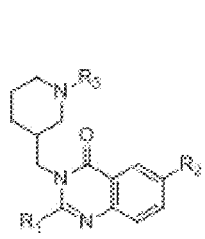
FIGS. 1A to 1C are the chemical structure of prior art quinazolinones.
Figure 1B:
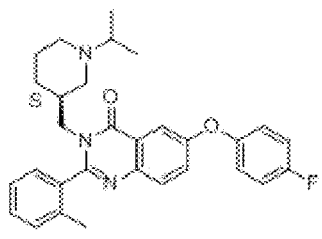
Figure 1C:
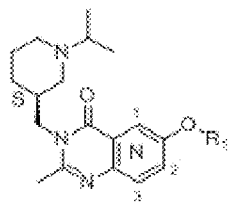

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. In order to aid in the understanding and preparation of the within invention, the following illustrative, non-limiting, examples are provided. Terms of degree such as "substantially," "about" and "approximately", mean a reasonable amount of deviation of the modified term such that the end result is not significantly changed. These terms of degree should be construed as including a deviation of at least 5% of the modified term if this deviation would not negate the meaning of the word it modifies. All publications cited are incorporated herein by reference.

$EC_{50}$: half-maximal effective concentration
$IC_{50}$: half-maximal inhibitory concentration
"hot": the radioactive form of the compound
"cold": the non-radioactive form of the compound
"GHRPs": growth hormone releasing peptides
"GH": growth hormone
"GHS": growth hormone secretagogues
"Subject" or "patient" refers to a subject in need of treatment for a condition, disorder or disease, or in need of a diagnosis for a condition, disorder or disease.

Presented herein are compounds and imaging tools that may be used to investigate changes in the GHS-R1a, in cancer cells and in cardiomyocytes as a possible marker of disease severity.

The term "cancer" (e.g. neoplastic disorder) as used in this document, refers to a disorder involving aberrant cell growth, proliferation or division (e.g. neoplasia). As cancer cells grow and divide the pass on their genetic mutations and proliferate characteristics to progeny cells. A "tumour" (e.g. neoplasm) is an accumulation of cancer cells. The compounds and methods disclosed herein may be used in the imaging, diagnosis and treatment of cancer, cancer cells, tumours, and/or symptoms associated therein.

Exemplary types of cancer that may be imaged or treated in accordance to the present invention, include testicular cancer, bladder cancer, cervical cancer, ovarian cancer, breast cancer, prostate cancer, neck and head cancer, lung cancer (e.g. non small cell lung cancer), endometrial cancer, pancreatic cancer, Kaposi's sarcoma, adrenal cancer, stomach cancer, colon cancer, rectal cancer, liver cancer, esophageal cancer, renal cancer, thyroid cancer, uterine cancer, skin cancer, oral cancer, brain cancer, spinal cord cancer, gallbladder cancer. The cancer may, for example, include sarcoma, carcinoma, melanoma, lymphoma, myeloma, or germ cell tumours. In some embodiments, the cancer is prostate cancer.

"Metastasis" refers to the dissemination of tumor cells via lymphatics or blood vessels. Metastasis refers also to the migration of tumor cells by direct extension through serous cavities, or subarachnoid or other spaces. Through the process of metastasis, tumor cell migration to other areas of the body establishes neoplasms in areas away from the site of initial appearance.

The present invention also provides a method of imaging a target site in a subject. The target site may be a tumor, for example prostate cancer, and may be used to distinguish between malignant and benign tumors by targeting the ghrelin receptor, which is known to have a differential expression in benign and malignant tumors.

Current clinical methods for PET imaging of prostate cancer remain unsatisfactory, due to their limited ability to distinguish benign prostatic hyperplasia (BPH) from malignancy. Growth Hormone Secretagogue Receptor 1a (GHS-R1a) is a G-protein Coupled Receptor that is highly expressed in prostate cancer. Previous studies by the applicant showed that, by targeting GHSR-1a, a fluorescein probe effectively distinguishes BPH and cancerous tissue. Therefore, it is proposed that the development of PET imaging agent targeting GHS-R1a has the potential to create a next generation clinical tool for accurate diagnosis of cancers, including prostate cancer. Four series of quinazolinone derivatives have been synthesized and their binding affinities with GHS-R1a were evaluated using radio ligand binding assay. A 3D QSAR model (CoMSIA) was developed to assist in the design of the $1^{st}$ series of fluorine-containing molecules, resulting two lead compounds (compounds 5b and 5e) with strong binding affinity with GHS-R1a (20.6 nM and 9.3 nM respectively). These two compounds were $^{18}$F-radiolabeled with radio-purity of greater than 98%. Further medicinal chemistry efforts have resulted in the $2^{nd}$, $3^{rd}$ and $4^{th}$ series of compounds. Among them, four compounds (5g, 15b, 19, 20) showed equivalent binding affinity to natural ghrelin and three compounds (5i, 10b, 17b) showed sub-nanomolar binding affinity. Compound 17b ($IC_{50}$: 0.33 nM; cLog D: 2.53) was successfully $^{18}$F-radiolabeled with a decay corrected radiochemical yield of 42% and a radio-purity of >99%. Preliminary in vivo evaluation on all radiolabelled compounds were performed in a murine model of prostate cancer.

Positron emission tomography (PET), including fluorine-18 PET, PET-computed tomography (CT) hybrid and PET-magnetic resonance imaging (MRI) hybrid imaging with the compounds of the present invention may enable oncologists to diagnose and stage cancer(s), and to enable cardiologists to predict LV dysfunction before it occurs through detection of early derangements in GHS-R1a, and to gauge the response to therapy. The compounds of the present invention can also be labeled with $^{76}$Br, $^{123}$I, $^{125}$I, and $^{131}$I.

In some embodiments, the compound of the present invention has the general formula I:

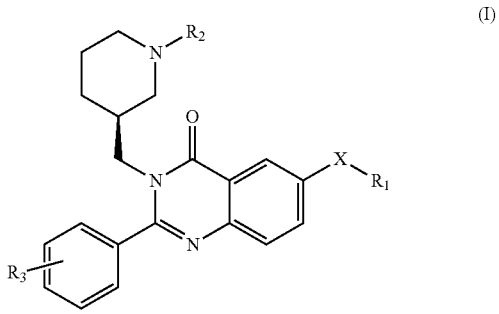

wherein R₂ is halogen, halosubstituted alkyl, alkyl, hydroxyl-alkyl, amino-alkyl;
X is ester, carbonyl or —CH₂—;
R₁ is mono-, or bicyclic aromatic or heroaromatic ring systems, optionally substituted by halo, alkyl, nitro, alkoxy, amino;
R₃ is one or two halo, halosubstituted alkyl, alkyl, nitro, hydroxyl-alkyl, alkyl tosylate; and to pharmaceutically acceptable salts.

In one embodiment of the present invention, halo and halosubstituted includes substitution with F, Br, or I.

In some embodiments, the halogen is F, Br or I.

In some embodiments, the compound of the present invention includes a detectable label selected from ¹⁸F, ⁷⁶Br, ¹²³I, ¹²⁵I, and ¹³¹I.

In some embodiments, the compound of the present invention is conjugated to other molecular entities or nanoparticles.

In some embodiments, R₁ is selected from the group consisting of:

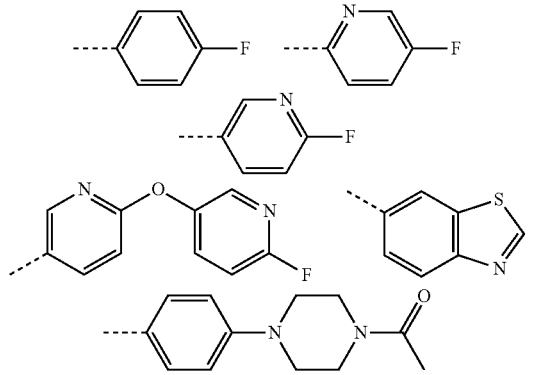

In some embodiments R₂ is selected from the group consisting of:

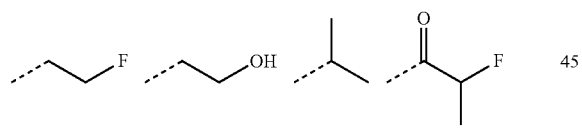

In some embodiments R₃ is selected from the group consisting of:
Methyl
Fluorine

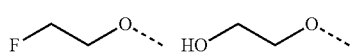

In some embodiments R₁ is selected from the group consisting of:

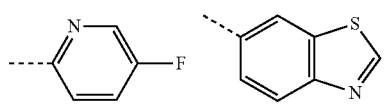

In some embodiments, R₂ is selected from the group consisting of:

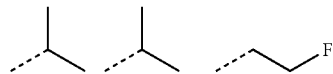

In some embodiments, the compound of the present invention is selected from the group consisting of:

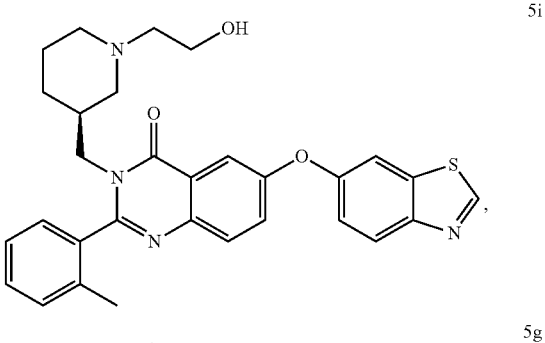

5i

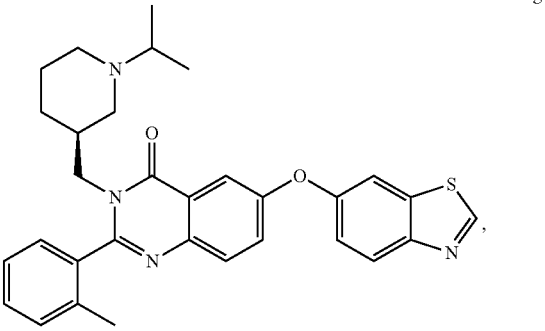

5g

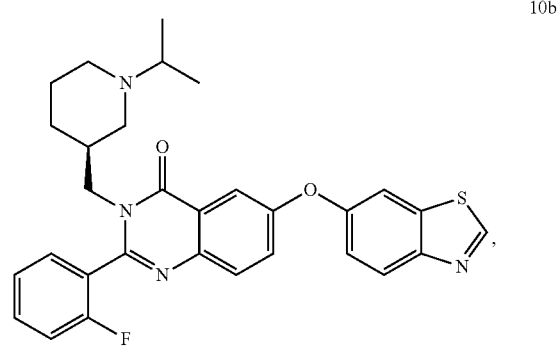

10b

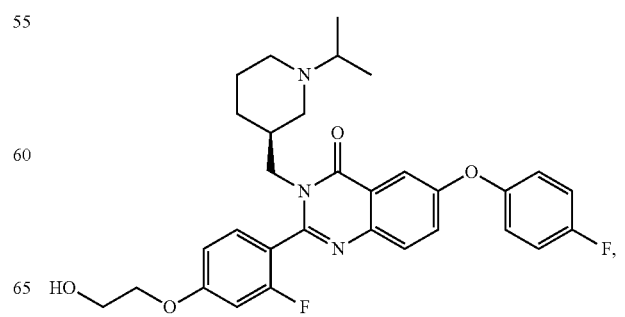

15b

19

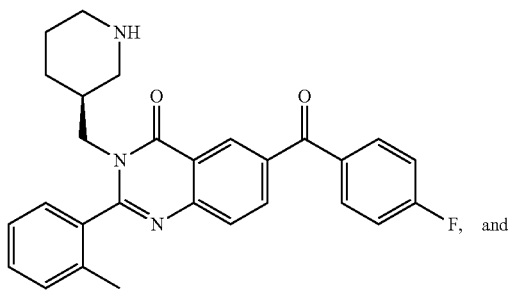

or a pharmaceutical acceptable salt thereof.

In some embodiments, the compound of the present invention is selected from the group consisting of:

[¹⁸F]5b

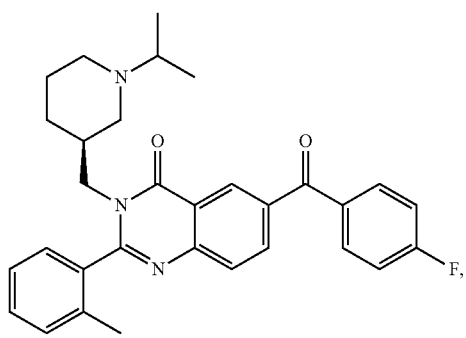

[¹⁸F]5e

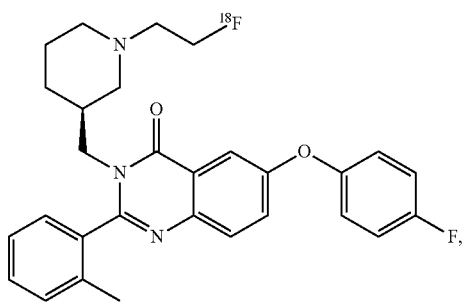

and

[¹⁸F]17b

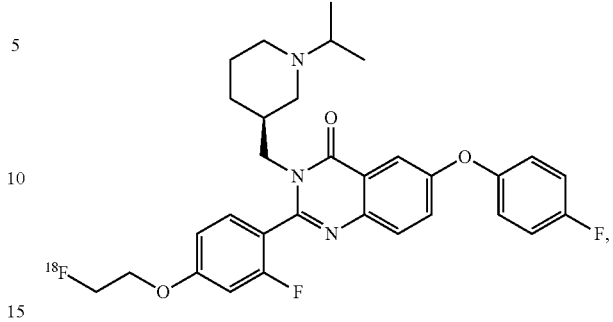

or a pharmaceutical acceptable salt thereof.

In another embodiment, the compound of the present invention is conjugated to other molecular entities or nanoparticles.

In another embodiment, the compound of the present invention is conjugated to or incorporated within a nanoparticle.

In another embodiment, the compound of the present invention the nanoparticle is selected from a group comprising: gold nanoparticles, dendrimers, iron oxide particles, liposomes, protein nanoparticles, or other polymeric nanoparticles.

In another embodiment, the compound of the present invention the compound is conjugated to a cytotoxic molecule.

In another embodiment, the compound of the present invention the cytotoxic molecule is selected from a group comprising: anthracyclins, taxanes, nucleotide analogues, platinum complexes, and kinase inhibitors.

In a further embodiment, the present invention provides a pharmaceutical composition comprising a quinazolinone derivative of the present invention and a pharmaceutically acceptable carrier.

Such pharmaceutical compositions may be used for diagnostic purposes, preferably, for visualization of organs and tissues having a ghrelin receptor, preferably, for diagnosis of tumors, including distinguishing between benign and malignant tumors. Any suitable solid tumor may be encompassed by the invention, both primary tumors and metastasis, of tumors selected from, but not limited to, from melanoma, colon, breast, lung, prostate, brain or head and neck cancer. Preferably for diagnosis of prostate cancer, including distinguishing between benign and malignant prostate cancer. Such pharmaceutical compositions may also be used for diagnosis of heart disease or growth hormone (GH) deficiency.

The pharmaceutical compositions of the present invention may be used for administration to subjects in a biologically compatible form suitable for administration in vivo. By "biologically compatible form suitable for administration in vivo" is meant a form of the substance to be administered in which any toxic effects are outweighed by the therapeutic or diagnostic effects. Administration of a therapeutically active amount of the pharmaceutical compositions of the present invention, or an "effective amount", is defined as an amount effective at dosages and for periods of time, necessary to achieve the desired result. A therapeutically effective amount of a substance may vary according to factors such as the disease state/health, age, sex, and weight of the recipient, and the inherent ability of the particular quinazolinone derivative to elicit a desired response. Dosage regimen may

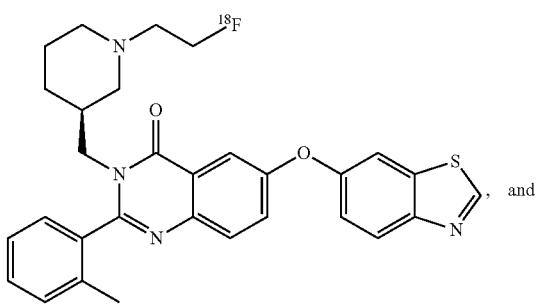

be adjusted to provide the optimum therapeutic response. For example, several divided doses may be administered daily or on at periodic intervals, and/or the dose may be proportionally reduced as indicated by the exigencies of the therapeutic situation. The amount of quinazolinone derivative for administration will depend on the nature of the quinazolinone derivative, the route of administration, time of administration and varied in accordance with individual subject responses. Suitable administration routes may be intramuscular injections, subcutaneous injections, intravenous injections or intraperitoneal injections, oral and intranasal administration. In a preferred embodiment, the administration route may be intravenous injection.

The pharmaceutical compositions may be provided in a kit that includes instructions or labels as to the use of the conjugate (i.e. imaging, diagnosis, etc. of ghrelin-receptors containing sites, such as tumors or cardiac tissue).

Such pharmaceutical compositions may be used to treat GH deficiency, stimulate GH secretion from the pituitary or increase appetite, attenuate cachexia in patient with cancer or chronic obstructive pulmonary disease. Such pharmaceutical compositions may also be used for suppressing ghrelin's orexigenic effects, treating obesity, regulating food intake, GI motility, gastric emptying or body weight, and treating ulcer or gastroparesis.

Such pharmaceutical compositions may also be used to treat a variety of disorders such as anorexia nervosa, heart failure, diabetes mellitus (including Type 1 and 2) or diabetes mellitus complications, constipation and Parkinson's disease. Such pharmaceutical compositions may also be used as a therapeutic agent to treat cancer.[9,10]

The quinazolinone derivatives of the present invention have been found to have high affinity for GHS-R1a receptors as demonstrated by receptor-ligand binding assays described in Example 1, some compounds having $IC_{50}$ nanomolar values in the single digits and even sub-nM values. As such, the quinazolinone derivative of the present invention are GH-SR1a ligands.

The quinazolinone derivatives of the present invention were also found to have low $EC_{50}$ values and may serve as GHS-R1a agonists. As such, quinazolinone derivatives of the present invention may be used for indications such as suppressing ghrelin's orexigenic effects, treating obesity, regulating food intake, GI motility, gastric emptying or body weight, and treating ulcer or gastroparesis, to treat a variety of disorders such as anorexia nervosa, heart failure, diabetes mellitus (including Type 1 and 2) or diabetes mellitus complications, constipation and Parkinson's disease.

As such, the present application includes methods of treating a disorder associated with GHS-R1a, including stimulation of growth hormone release, increase in appetite, gastric emptying, and cachexia, including cachexia in patients with cancer. The method may include administering to a person in need, an effective amount of a quinazolinone derivatives of the present invention.

In order to aid in the understanding and preparation of the within invention, the following illustrative, non-limiting, examples are provided.

Advantages

The quinazolinone derivatives of the present invention are different from existing technology in that it attempts to distinguish between malignant and benign tumours by targeting the ghrelin receptor, which is known to have a differential expression in benign and malignant tumours compare to, for example, normal prostetic tissue. This is an issue prevalent with imaging modalities in current clinical use (18F- and 11C-PET CT, PET/CT, MRI and mpMRI).

Applying the principles disclosed herein, a person of skill in the art will be able to identify compounds that have binding affinity with GHS-R1a. Thus, the scope of the present disclosure extends beyond the exemplary compounds disclosed.

A number of theories, hypothesis, beliefs and postulations are discussed herein. Such theories, hypothesis, beliefs and postulations are not intended to be binding or to limit the scope of the disclosure.

The Examples set forth below are intended to illustrate but not limit the scope of the disclosure.

EXAMPLE 1

Figure 2:
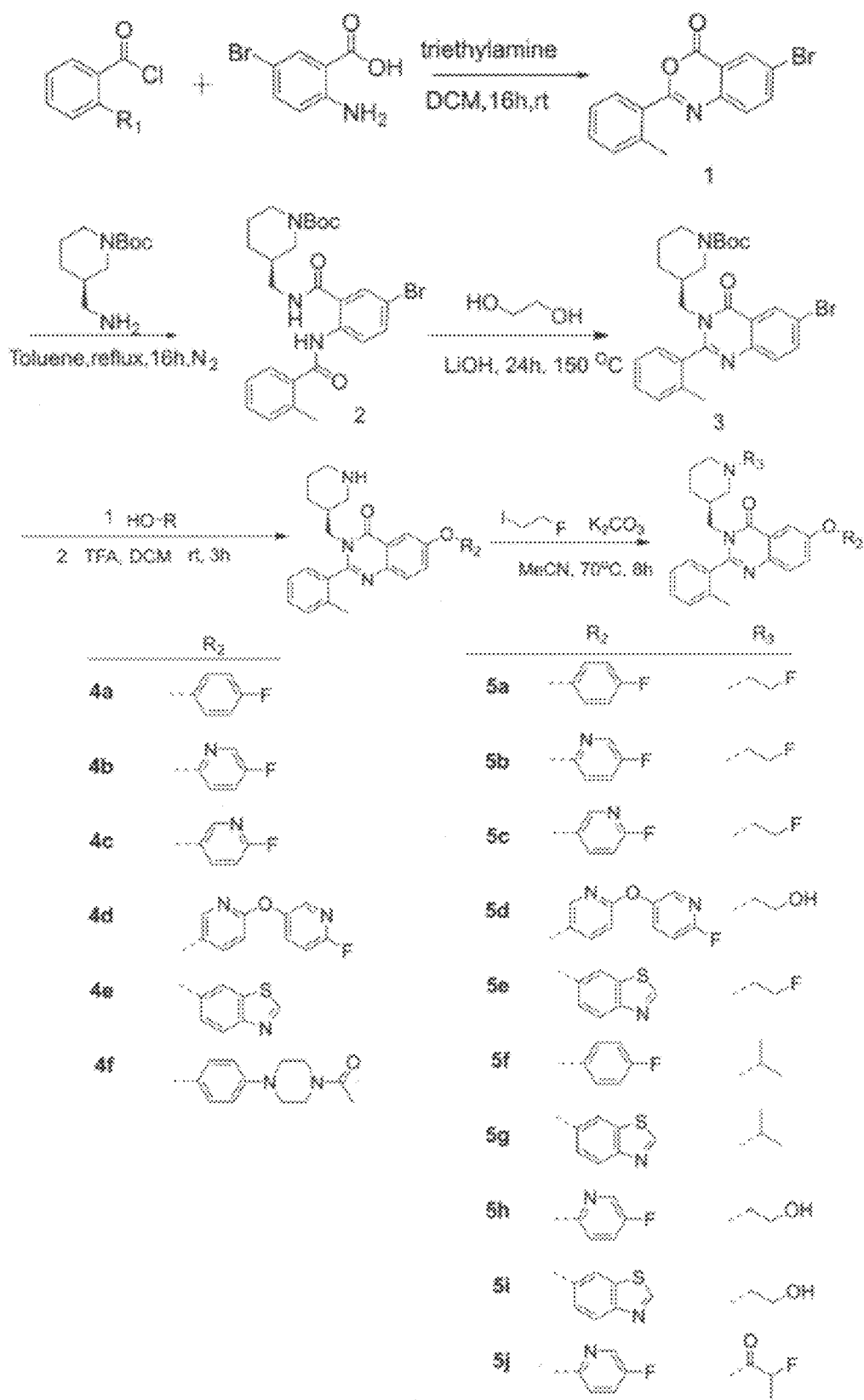
FIG. 2 is a scheme (scheme 1) showing the synthesis of fluoride containing compound in accordance to one embodiment of the present invention.

Aim: to synthesize fluorine-containing compounds with strong binding affinity with GHS-R1a. Candidate molecules that exhibit strong binding affinity will proceed to the radiolabelling stage using fluorine-18 ($^{18}F$), a commonly used radioisotope for PET imaging. To acquire thorough and complete SAR information, some compounds without fluorine were also synthesized. Our initial effort was put on modifying the $R_1$ and $R_2$ substituents as suggested by the above mentioned SAR data. Compound 4a and 5f reported previously were used as references. The 1$^{st}$ series of quinazolinone analogues was synthesized according to Scheme 1 (see FIG. 2), which are similar to the reported methods. 2-amino-5-bromobenzoic acid was treated with o-toluoyl chloride to form benzoxazinone 1. The addition of BOC-protected aminomethylpiperidine led to uncyclized product 2, which was cyclized under microwave irritation to give compound 3. Ullmann coupling reactions were then performed with aromatic hydroxy building block to form the intermediates, followed by BOC-deportation to furnish compound 4a-4f. Further N-alkylations on the piperidine nitrogen atoms using nucleophilic substitution conditions furnish compound 5a-5j.

Besides the effort of improving the binding affinity, we also considered the lipophilicity which is indicated by Log P and/or Log D. Generally, the less lipophilic imaging agents (lower log P values) potentially resulted in more favorable biodistribution characteristics due to fast clearance and less blood protein bindings. We aim to optimize the lipophilicity of the small molecules to have calculated Log P in the approximate range 1-5.

Based on previous SAR data, we decided to synthesize only (S)-stereoisomers. The Ki value of compound 4a reported in the literature was 0.9 nM, while it was determined to have $IC_{50}$ of 5.6 nM in our lab. This compound has favorable lipophilicity (cLog $D_{7.4}$=2.22). To allow for F18 radiolabelling, compound 5a was made by alkylation to incorporate fluoroethyl group on the piperidine, the $IC_{50}$ and cLog D were increased to 29.5 nM and 4.5. To reduce the cLog D, compounds 5b and 5c were synthesized by replacing the fluorophenyl with fluoropyridinyl group. The binding affinity of compound 5b was increased to 20.6 nM while the binding affinity of compound 5c was decreased to 64.2 nM. The SAR suggested by comparing compounds 4a, 4b, 4c with compounds 5a, 5b, 5c showed that incorporation of fluoroethyl group on the piperidine resulted in decreased or similar binding affinity and increased cLogD. As suggested by compounds 4d, 5d, 4f, a bulkier substituent in $R_1$ position is not beneficial for the binding affinity. However, a benzothiazolyl group in the same position improved the $IC_{50}$ to 5.3 nM (compound 4e), which is nearly equivalent to that of natural ghrelin (3.3 nM). After incorporation of fluoroethyl group on the piperidine, the IC$_{50}$ surprisingly increased to 9.3 nM, which is opposite to the SAR obtained previously. It has been demonstrated that the free amines on every studied molecule played an important role in binding with GHS-R1a. The amines were protonated and the positive charge established salt bridge interactions with Glu124, thus anchoring the ligands to the binding pocket of GHS-R1a. Without surprise, the introduction of the 2-fluoropropionyl group into piperidine diminished the binding affinity (compound 5h). This is probably due to the formation of amide bond preventing the molecule from protonation, thus not able to anchor the ligand to the binding pocket of GHS-R1a. Previous studies suggested that incorporation of isopropyl group on the piperidine gave the best binding affinity. Compound 5g was made and tested to have IC$_{50}$ of 1.8 nM.

TABLE 1 the 1$^{st}$ series of quinazolinone derivatives with IC$_{50}$ values

| Compds. | IC$_{50}$ (nM) | cLog D$_{7.4}$ |
|---|---|---|
| 4a | 5.6 (0.9)$^a$ | 2.22 |
| 4b | 52.0 | 0.90 |
| 4c | 68.5 | 1.24 |
| 4d | 82.9 | 1.24 |
| 4e | 5.3 | 1.89 |
| 4f | 587.0 | 1.62 |
| 5a | 29.5 | 4.5 |
| 5b | 20.6 | 3.4 |
| 5c | 62.4 | 3.53 |
| 5d | 65.2 | 2.48 |
| 5e | 9.3 | 4.25 |
| 5f | 3.7 (0.9)$^a$ | 3.32 |
| 5g | 1.8 | 2.25 |
| 5h | 18.2 | 2.08 |
| 5i | 0.4 | 2.62 |
| 5j | >1000 | 3.43 |
| Ghrelin (1-28) | 3.3 | |

$^a$The Ki values reported in the literature.

The first round of modification provided us two lead compounds 5b and 5e, both compounds were proceeded to radiolabelling stage as described in latter session. The optimization also provided a high quality compound 5g and compound 5i with strong binding affinity and optimal cLogD. Unfortunately, these compounds do not possess a fluorine atom, which makes F18 radiolabelling impossible. The second round of structural modification will focus on compound 5g with the aim to make F18 radiolabelling possible while maintaining the strong binding affinity with GHS-R1a.

Figure 3:
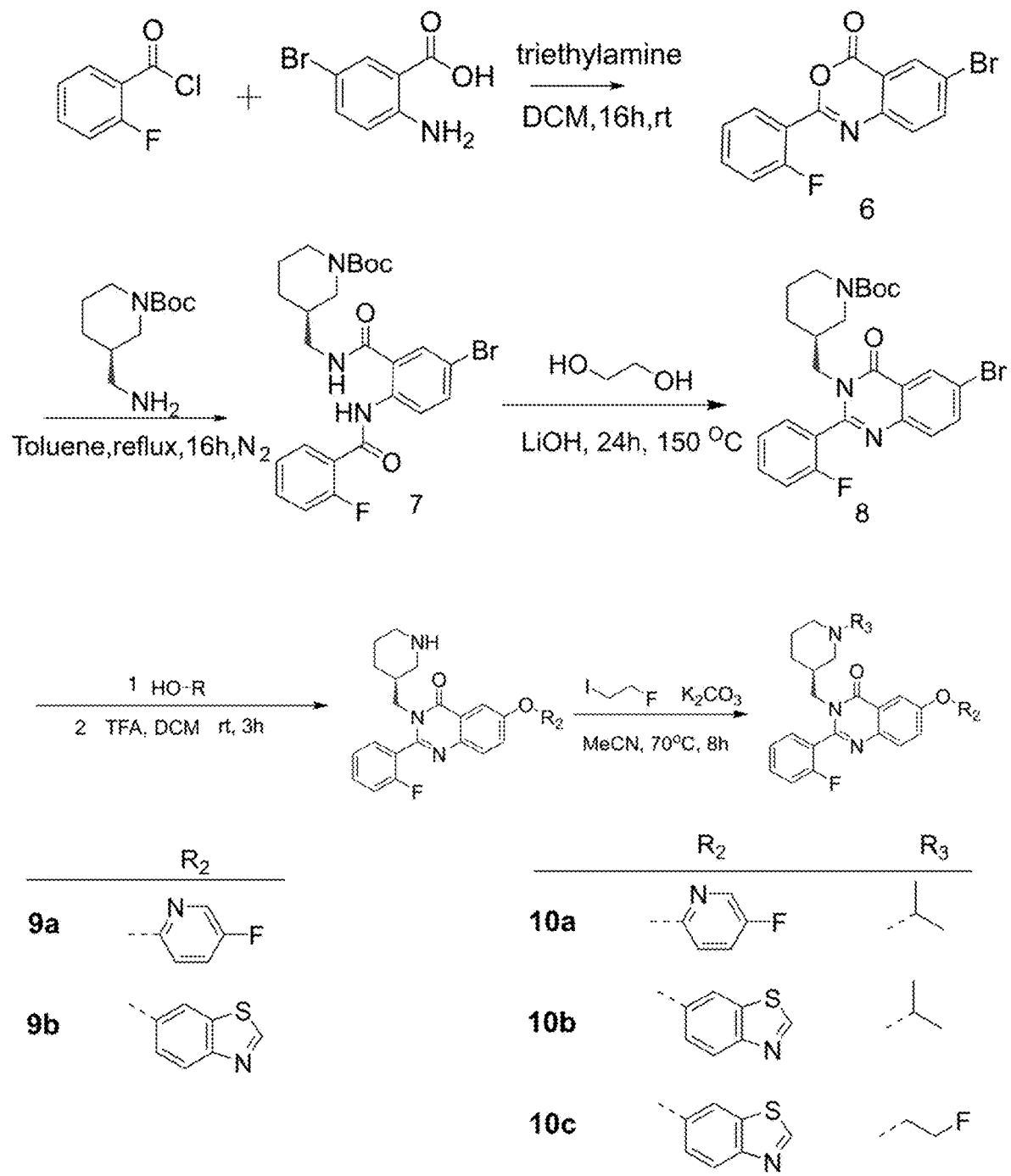
FIG. 3 is a scheme (scheme 2) showing the synthesis of fluoride containing compound in accordance to another embodiment of the present invention.

Design, Synthesis and Evaluation of the 2$^{nd}$ Series of Quinazolinone Derivatives Given the fact that the size of a methyl group is similar to that of the fluoride, we decided to replace the methyl group at the western part of the molecule with fluoride for compound 5g. Following the synthesis route as depicted in Scheme 2 (similar to Scheme 1 except replacing the o-toluoyl chloride with 2-fluorobenzoyl chloride; see FIG. 3), compound 10b was made. Surprisingly, this compound turned out to have subnanomolar IC$_{50}$ (0.02 nM), implying that fluoride substitution with methyl group is actually more favorable in the binding affinity. Compound 10b also showed excellent cLog D (2.39). Encouraged by the result, we further synthesized a precursor for F18 radiolabelling of this compound by replacing fluorine with nitro leaving group, but the radiolabeling was not successful due to the nitro being a week leaving group. For ease of radiolabeling, compound 10c was made with fluoroethyl group in R$_2$ position, but the IC$_{50}$ increased to 8.1 nM.

TABLE 2 the 2$^{nd}$ serial of quinazolinone derivatives with IC$_{50}$ values

| Compds. | IC$_{50}$ (nM) | cLog D$_{7.4}$ |
|---|---|---|
| 9a | 935.2 | 0.53 |
| 9b | 16.0 | 1.57 |
| 10a | 70.5 | 1.53 |
| 10b | 0.02 | 2.39 |
| 10c | 8.1 | 3.99 |

Figure 4:
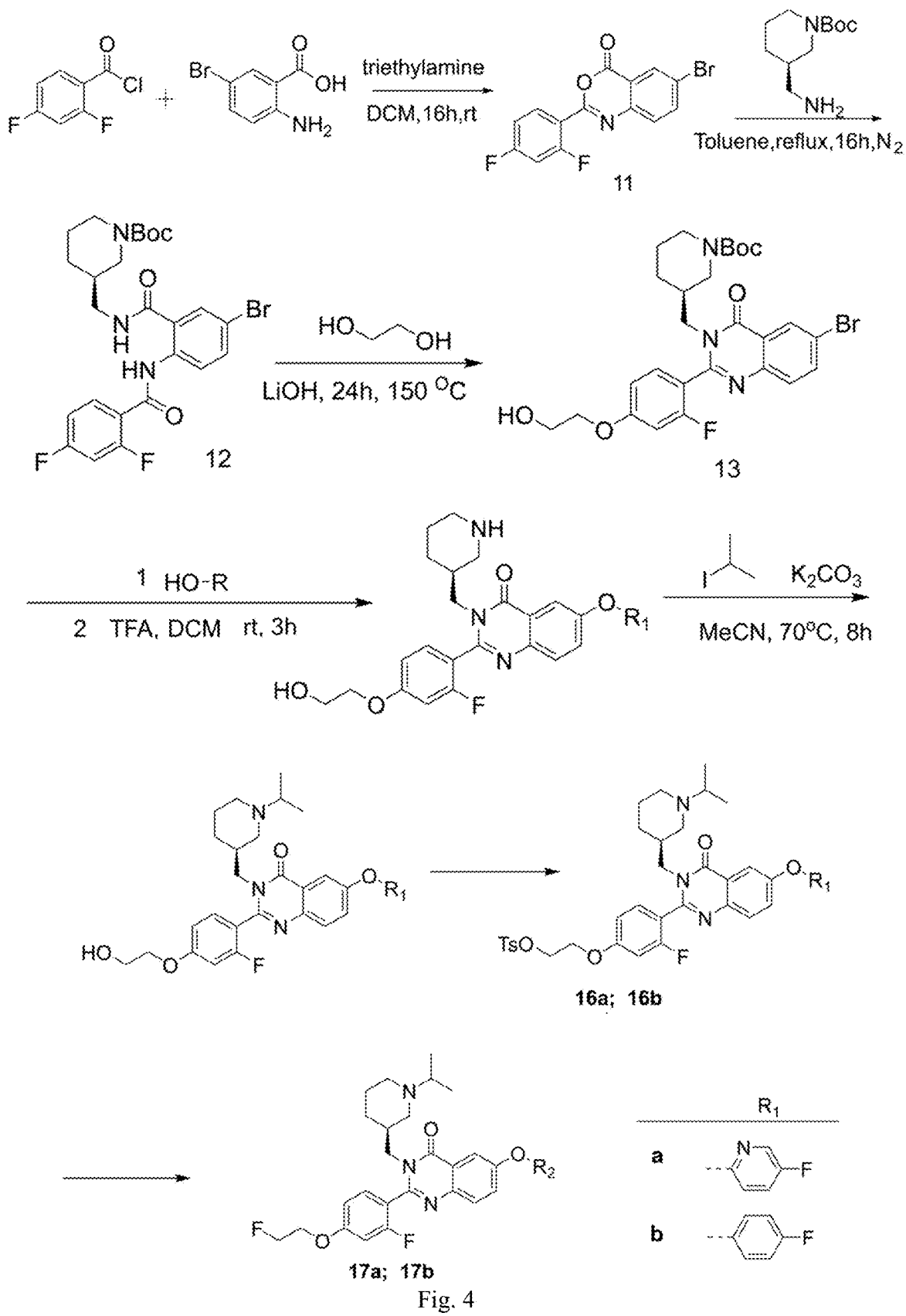
FIG. 4 is a scheme (scheme 3) showing the synthesis of fluoride containing compound in accordance to another embodiment of the present invention.

Design, Synthesis and Evaluation of the 3$^{rd}$ Series of Quinazolinone Derivatives The results from the second round of modification suggested that isopropyl substituent in R$_2$ position consistently gave an increased binding affinity regardless of modifications on the other part of the molecule. The SAR also suggested that the fluorine at ortho position of the phenyl group at the eastern part of the quinazolinone core has the potential to increase the binding affinity. We decided to keep the isopropyl substituent at R$_2$ and fluorine at ortho position of the phenyl group while explore other site for F18 radiolabelling. We decided to incorporate fluoroethoxy group on phenyl group at the eastern part of the quinazolinone core. Compound 14-17a and 14-17b were made according to scheme 3 (see FIG. 4). The hydroxyethoxy group was first introduced during the cyclization step via nucleophilic aromatic substitution of the para-fluorine. It was followed by Ullmann coupling reactions and Boc-deprotecion to furnish compound 14a and 14b. Alkylation with 2-bromopropane were then performed to furnish compound 15a and 15b. Ytterbium(III) catalyzed tosylation on the hydroxyl group gave compound 16a and 16b, which was followed by fluorination to furnish compound 17a and 17b. Compound 17b showed sub-nanomolar binding affinity (0.33 nM) and it was further radiolabeled by fluorine-18.

TABLE 3 the 3$^{rd}$ serial of quinazolinone derivatives with IC$_{50}$ values

| Compds. | IC$_{50}$ (nM) | cLog D$_{7.4}$ |
|---|---|---|
| 14a | 353.1 | −0.08 |
| 14b | 19.8 | 0.74 |
| 15a | 40.1 | 0.89 |
| 15b | 2.3 | 1.76 |
| 17a | 17.6 | 1.55 |
| 17b | 0.33 | 2.53 |

Figure 5:
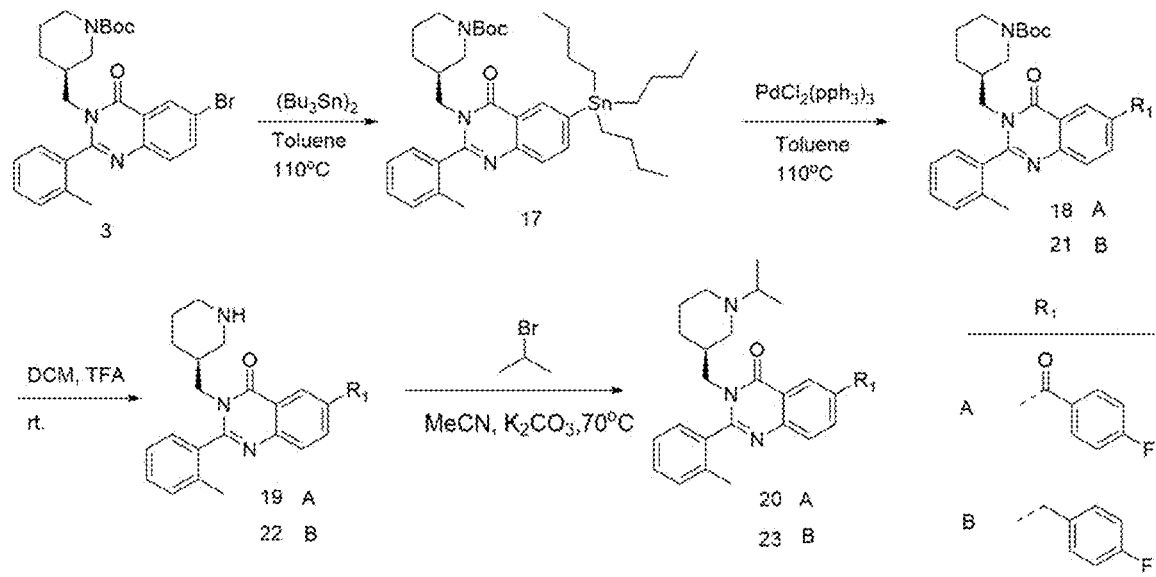
FIG. 5 is a scheme (scheme 4) showing the synthesis of fluoride containing compound in accordance to another embodiment of the present invention.

Design, Synthesis and Evaluation of the 4$^{th}$ Series of Quinazolinone Derivatives As suggested by literature and the IC$_{50}$ tested in our lab, compound 5f has equivalent binding affinity with natural ghrelin and a reasonable cLogD value (3.32). The compound possesses fluorine which can potentially be substituted by radioactive fluorine 18. To make the radiolabeling of this compound feasible, the 4-fluorophenoxy was replaced with fluorobenzoyl group. We hypothesized that the binding affinity will maintain. The precursor with nitro group in replacement of fluorine can be made readily, and the electron withdrawing carbonyl group will allow for F18-radiolabelling of the compound. Compounds 19 and 20 were made following the synthesis route as described in Scheme 4 (see FIG. 5). Staring from compound 3, the aryl stannane 17 was made by treating 3 with bis(tributyltin), which was followed by stille coupling reaction to give compound 18. Boc-deprotection was then performed to furnish compound 19, which was followed by alkylation to furnish compound 20. As expected, compound 20 has an $IC_{50}$ of 3.8 nM, which is equivalent to that of compound 5f and natural ghrelin. Surprisingly, compound 19 also showed very strong binding affinity (4.0 nM). Both compounds have excellent cLogD values. Compound 23, with a methylene bridge, also had favorable properties.

TABLE 4 the 4$^{th}$ series of quinazolinone derivatives with $IC_{50}$ values

| Compds. | $IC_{50}$ (nM) | cLog $D_{7.4}$ | Compds. | $IC_{50}$ (nM) | cLog $D_{7.4}$ |
|---|---|---|---|---|---|
| 19 | 4.0 | 1.82 | 20 | 3.8 | 2.76 |
| 23 | 0.3 | 4.80 | | | |

$^{18}$F Radiochemistry

Figure 6:
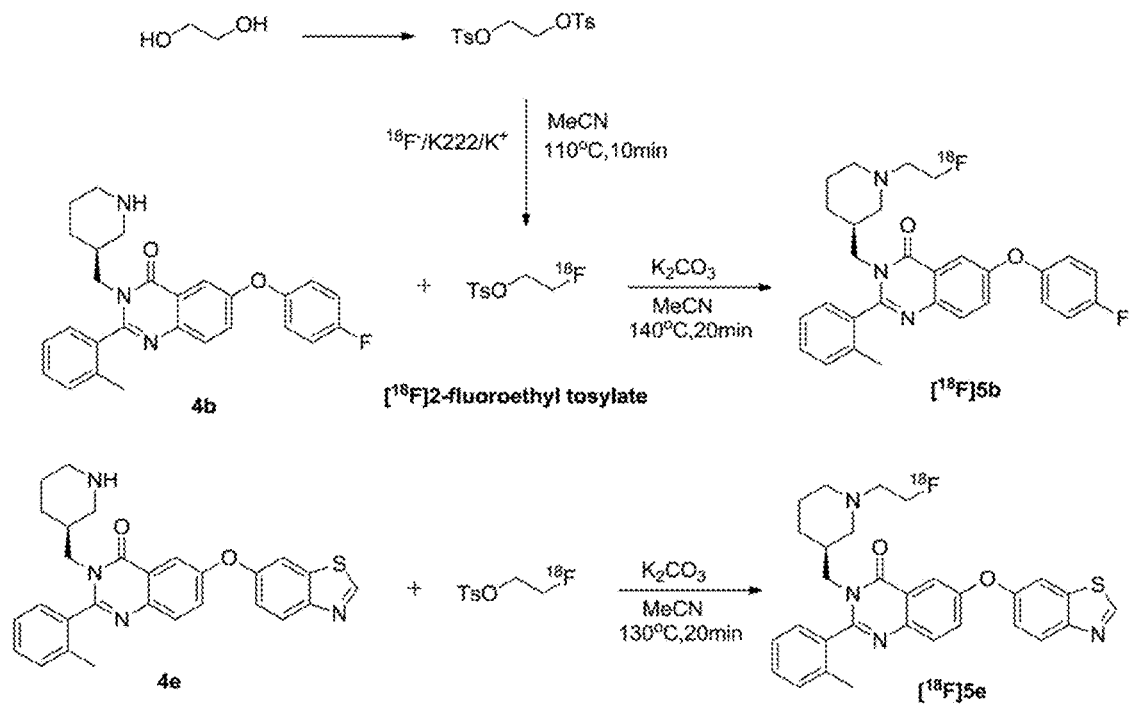
FIG. 6 is a scheme (scheme 5) showing the radiosynthesis of compounds [$^{18}$F]5b and [$^{18}$F]5e.

Compounds 5b and 5e obtained from the first round of optimization were proceeded to radiolabelling stage through a two-step approach as described in Scheme 5 (see FIG. 6). The bitosylate was first made from tosylation of ethylene glycol. Nucleophilic substitution of the bi-tosylate with the [$^{18}$F$^-$]anion acquired from the PET cyclotron led to the formation of radioactive compound [$^{18}$F]2-fluoroethyl tosylate. The non-decay corrected radiochemical yield of [$^{18}$F] 2-fluoroethyl tosylate was around 50%. After the workup and purification, only 20% yield was obtained. The loss of the yield mainly occurred during the long evaporation step as [$^{18}$F]2-fluoroethyl tosylate has relatively low boiling point.

Figure 7:
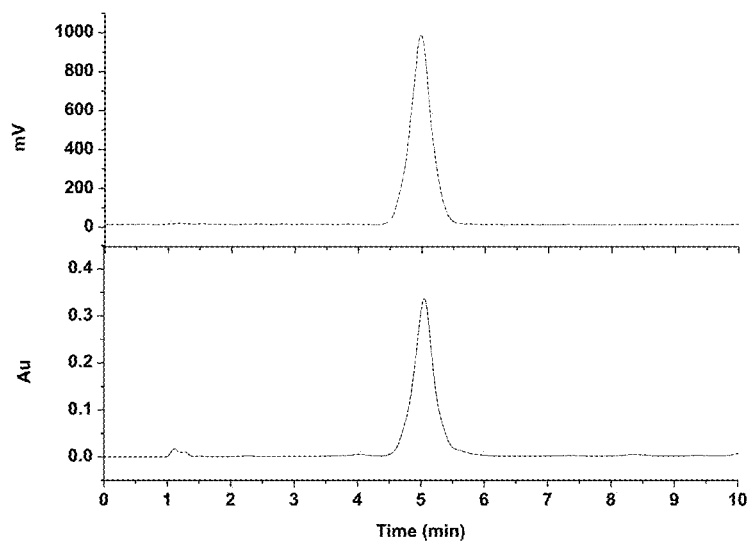
FIG. 7 stacked HPLC chromatograms ($\lambda$=254 nm) (bottom curve) and radio chromatograms (top curve) for 5b and [$^{18}$F]5b.
Figure 8:
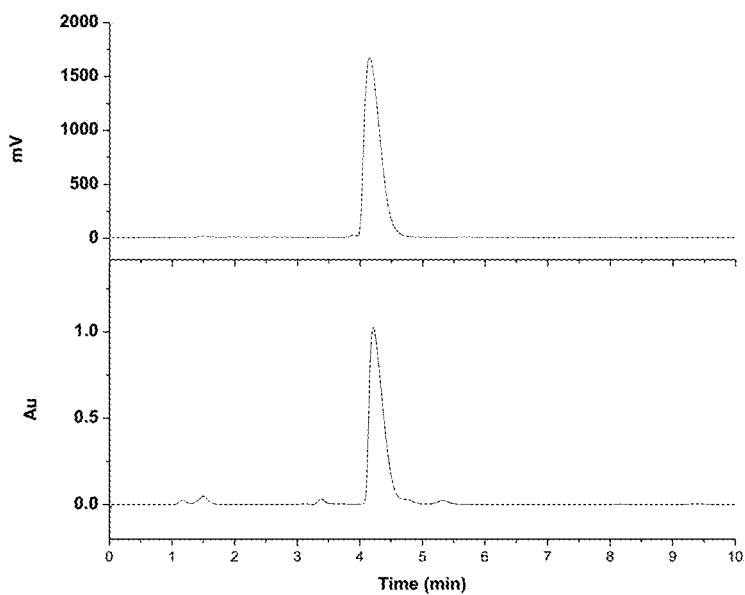
FIG. 8 stacked HPLC chromatograms ($\lambda$=254 nm) (bottom curve) and radio chromatograms (top curve) for 5e and [$^{18}$F]5e.

The [$^{18}$F]fluoroalkylation of amine precursor 4b using intermediate [$^{18}$F]2-fluoroethyl tosylate yielded the desired ligands [$^{18}$F]5b with moderate overall decay-corrected yields (10.3%) and high purities (≤99) (Table 5). Further evidence for successful labeling of 4b to [$^{18}$F]5b was provided by a co-injection of a pre-mixed solution of the cold standard 4b and "hot" ligand [$^{18}$F]5b (FIG. 7). By employing the same method, radioligand [$^{18}$F]5e was synthesized with overall decay-corrected yields of 7.0% and greater than 98% purity. Further evidence for successful labeling of [$^{18}$F]5e from 4e was also provided by a co-injection of a pre-mixed solution of the cold standard 4e and "hot" ligand [$^{18}$F]5e (FIG. 8).

TABLE 5

Radiosynthesis Data

| Radioligand | Radiochemical Yield (%) | Radiochemical Purity (%) | Total Synthesis Time (mins) |
|---|---|---|---|
| [$^{18}$F]5b | 10.3 ± 0.8 | ≥99 | 105 ± 1.7 |
| [$^{18}$F]5e | 7.0 ± 0.6 | ≥99 | 127 ± 7.1 |
| [$^{18}$F]17b | 42 ± 10 | ≥99 | 71 ± 1 |

Figure 9:
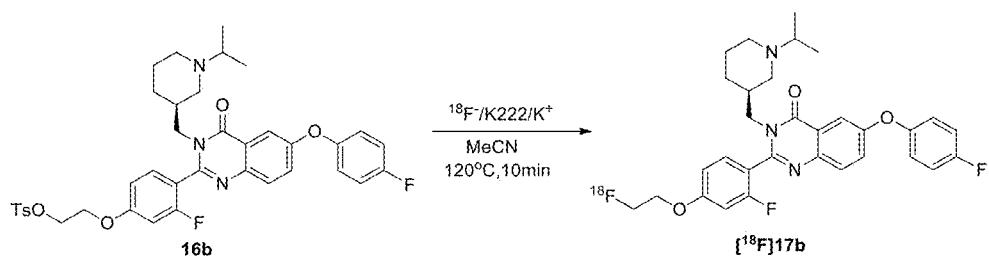
FIG. 9 is a scheme (scheme 6) showing the s radiosynthesis of compound [$^{18}$F]17b.

Compound 17b shows excellent binding affinity ($IC_{50}$: 0.33 nM) and cLogD (cLog D: 2.53). Using compound 16b as precursor (Scheme 6 seen in FIG. 9), it was successfully $^{18}$F-radiolabeled in one step with a decay corrected radiochemical yield of 53% and a radio-purity of >99%.

Figure 10:
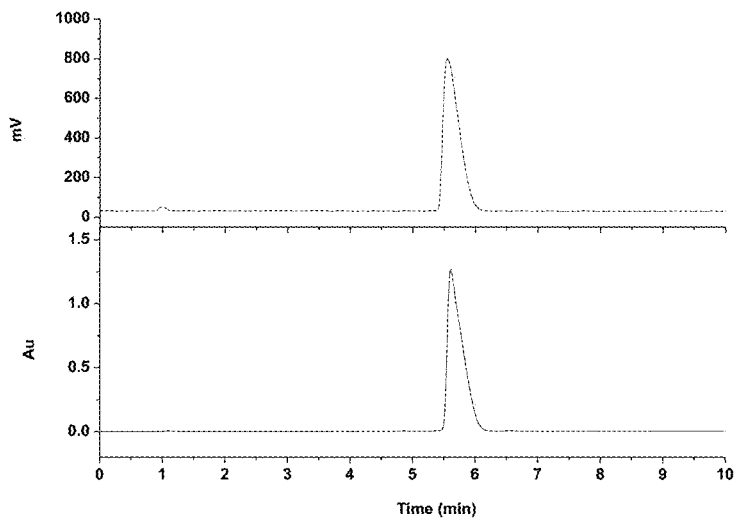
FIG. 10 stacked HPLC chromatograms ($\lambda$=254 nm) (bottom curve) and radio chromatograms (top curve) for 17b and [$^{18}$F]17b.
Figure 11:
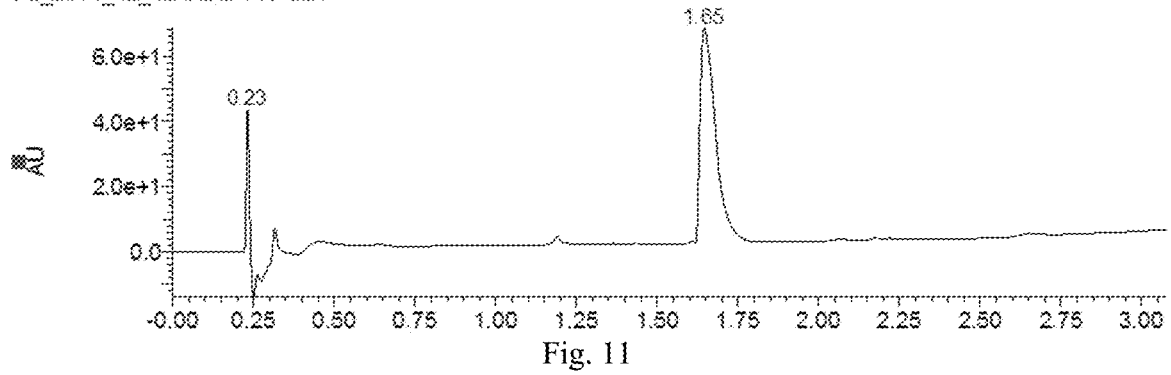
FIG. 11 is a U-HPLC chromatogram for compound 4a (purity 97%) [% product peak area/impurity peak areas].
Figure 12:
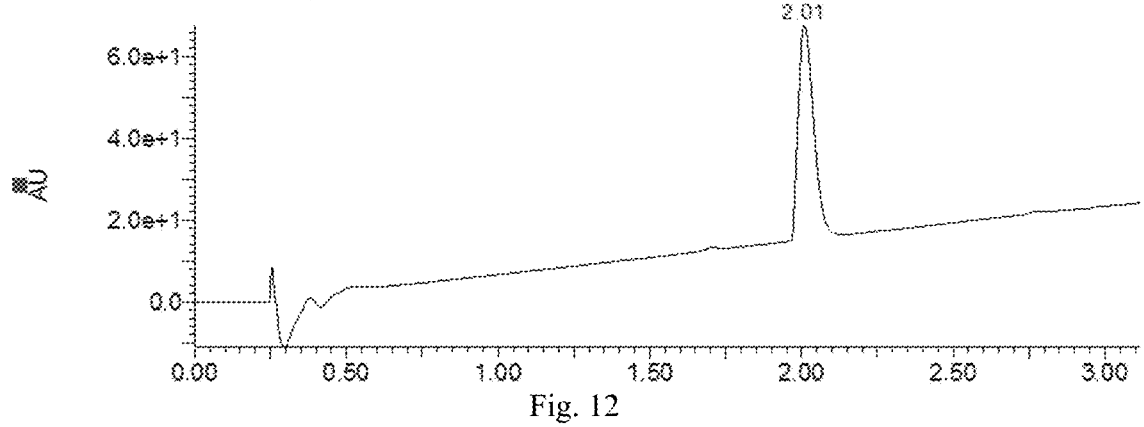
FIG. 12 is a U-HPLC chromatogram for compound 4b (purity 99%) [% product peak area/impurity peak areas].
Figure 13:
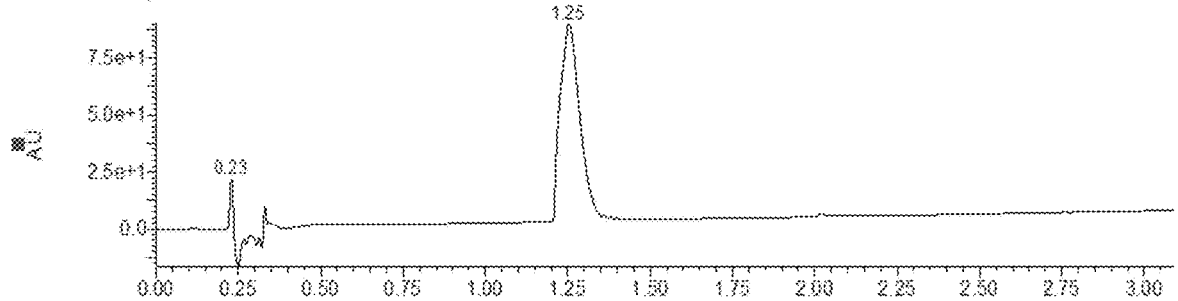
FIG. 13 is a U-HPLC chromatogram for compound 4c (purity 99%) [% product peak area/impurity peak areas].
Figure 14:
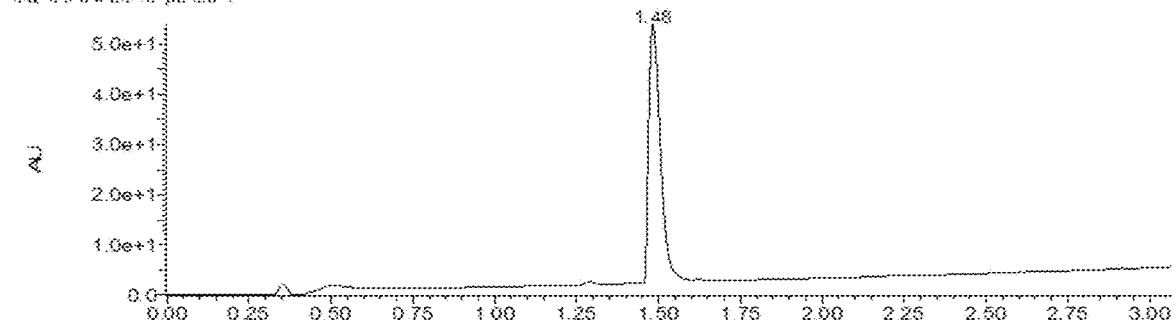
FIG. 14 is a U-HPLC chromatogram for compound 4d (purity 98%) [% product peak area/impurity peak areas].
Figure 15:
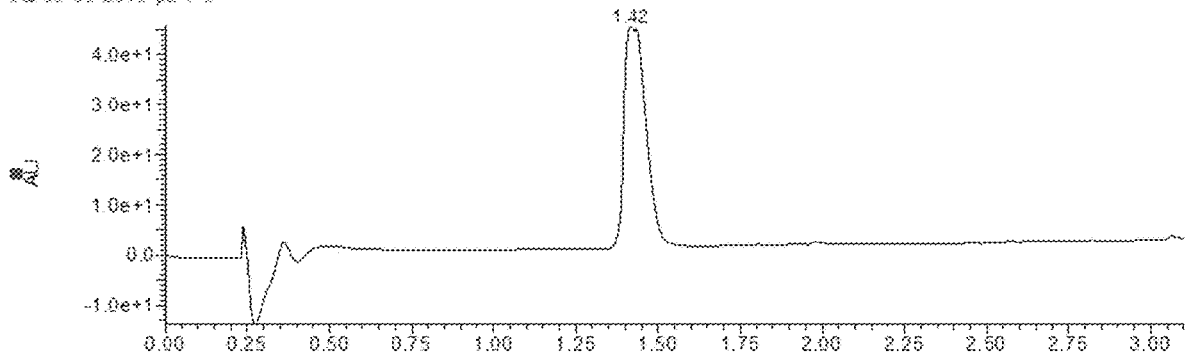
FIG. 15 is a U-HPLC chromatogram for compound 4e (purity 98%) [% product peak area/impurity peak areas].
Figure 16:
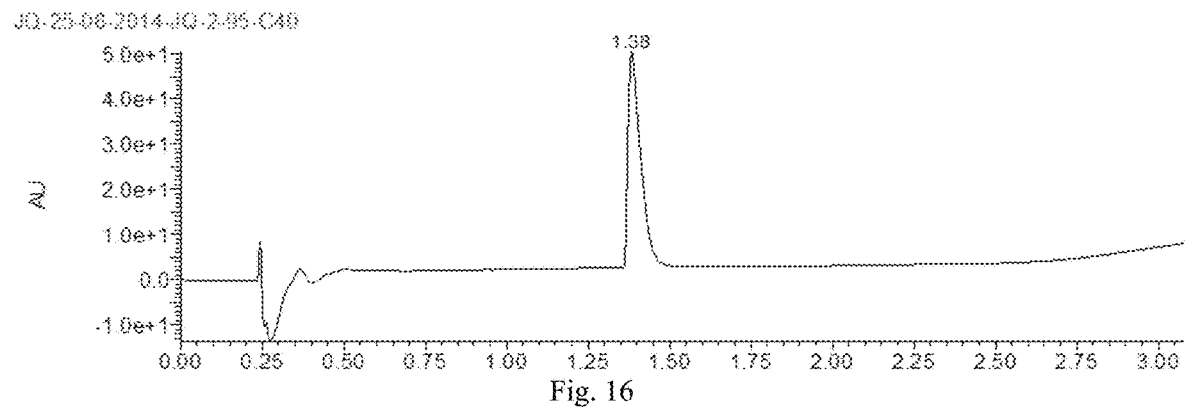
FIG. 16 is a U-HPLC chromatogram for compound 4f (purity 99%) [% product peak area/impurity peak areas].
Figure 17:
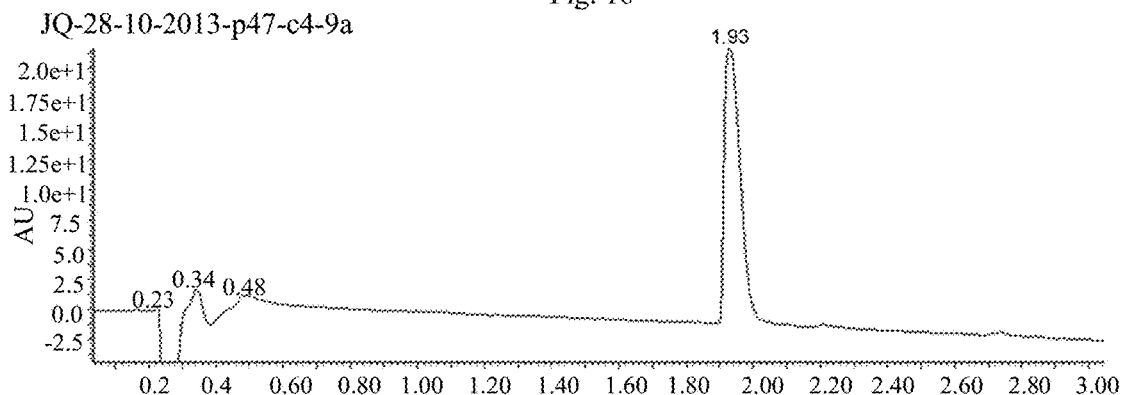
FIG. 17 is a U-HPLC chromatogram for compound 5a (purity 99%) [% product peak area/impurity peak areas].
Figure 18:
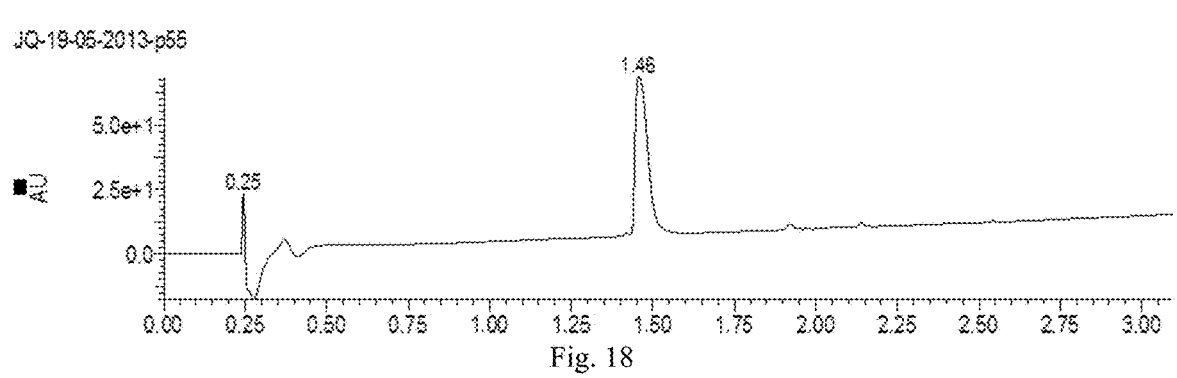
FIG. 18 is a U-HPLC chromatogram for compound 5b (purity 98%) [% product peak area/impurity peak areas].
Figure 19:
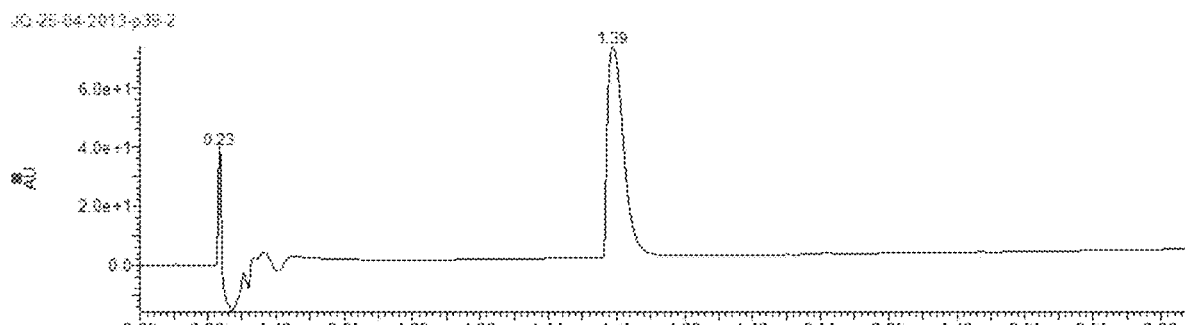
FIG. 19 is a U-HPLC chromatogram for compound 5c (purity 99%) [% product peak area/impurity peak areas].
Figure 20:
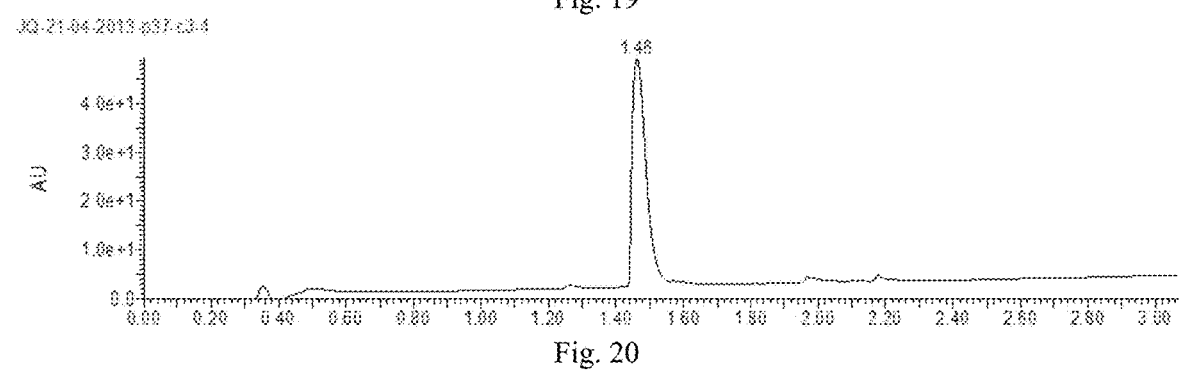
FIG. 20 is a U-HPLC chromatogram for compound 5d (purity 95%) [% product peak area/impurity peak areas].
Figure 21:
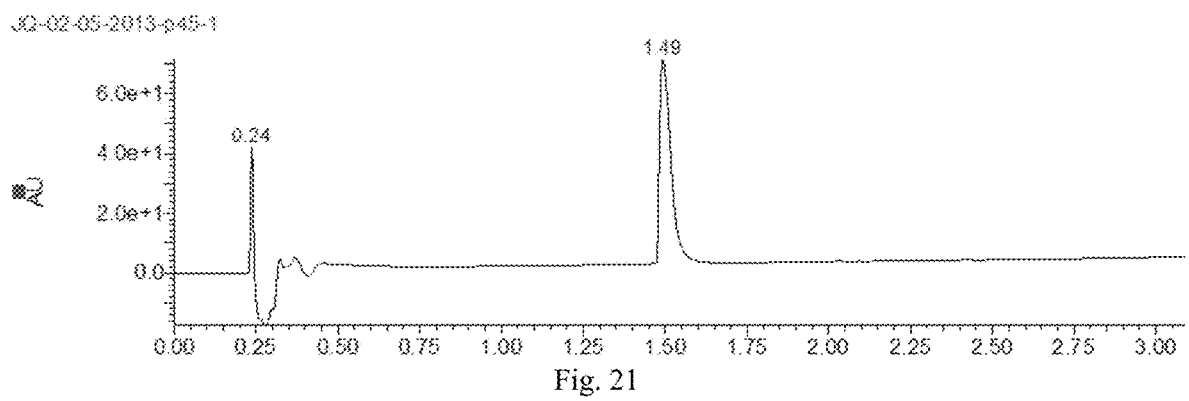
FIG. 21 is a U-HPLC chromatogram for compound 5e (purity 99%) [% product peak area/impurity peak areas].
Figure 22:
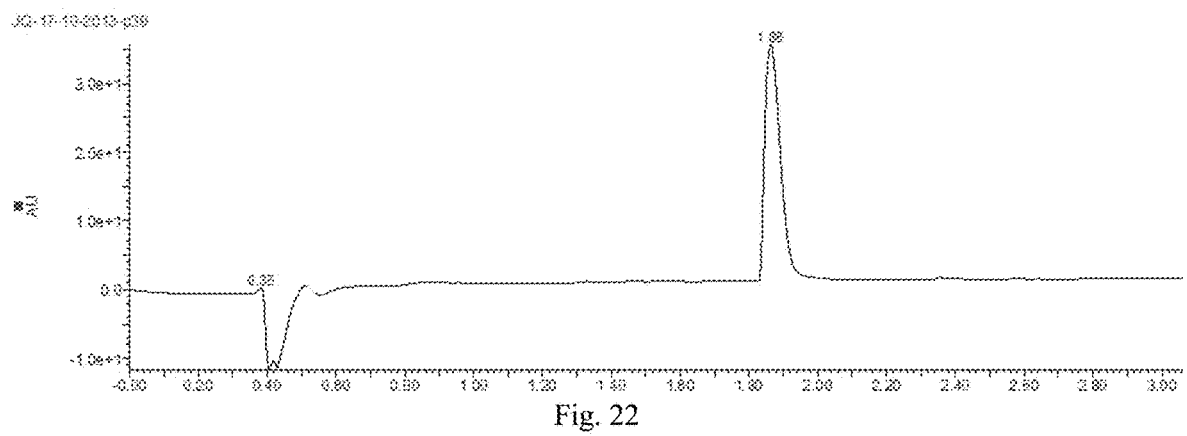
FIG. 22 is a U-HPLC chromatogram for compound 5f (purity 99%) [% product peak area/impurity peak areas].
Figure 23:
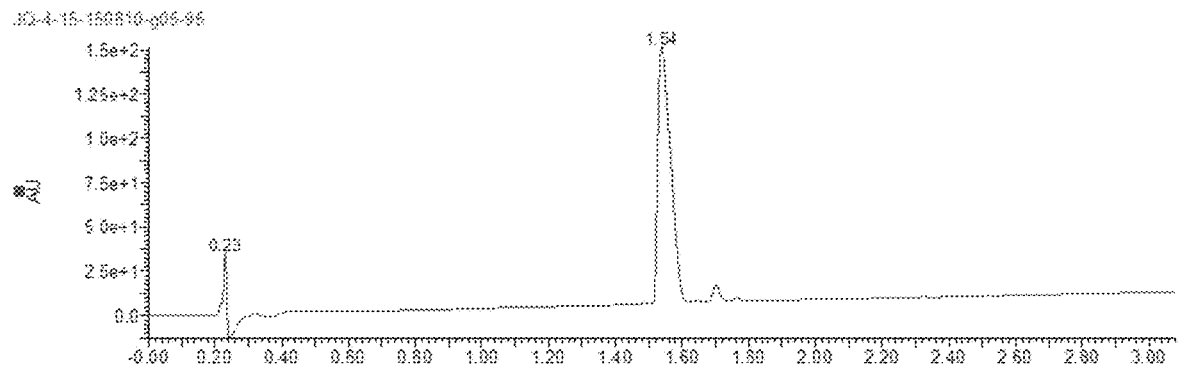
FIG. 23 is a U-HPLC chromatogram for compound 5g (purity 96%) [% product peak area/impurity peak areas].
Figure 24:
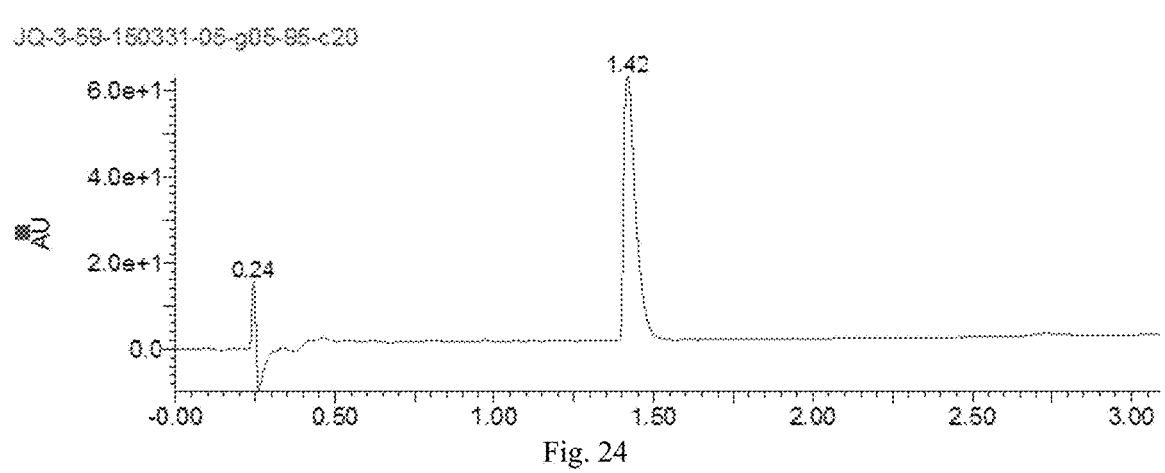
FIG. 24 is a U-HPLC chromatogram for compound 5h (purity 99%) [% product peak area/impurity peak areas].
Figure 25:
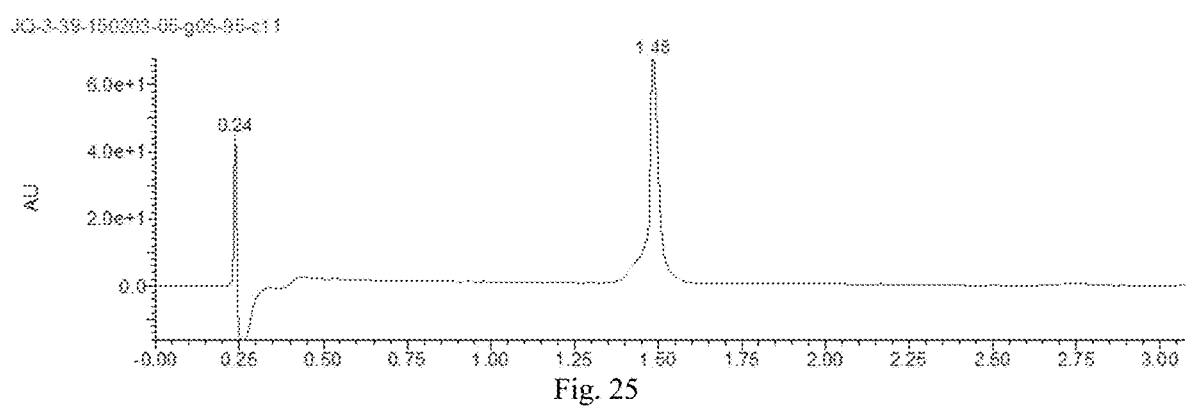
FIG. 25 is a U-HPLC chromatogram for compound 5i (purity 98%) [% product peak area/impurity peak areas].
Figure 26:
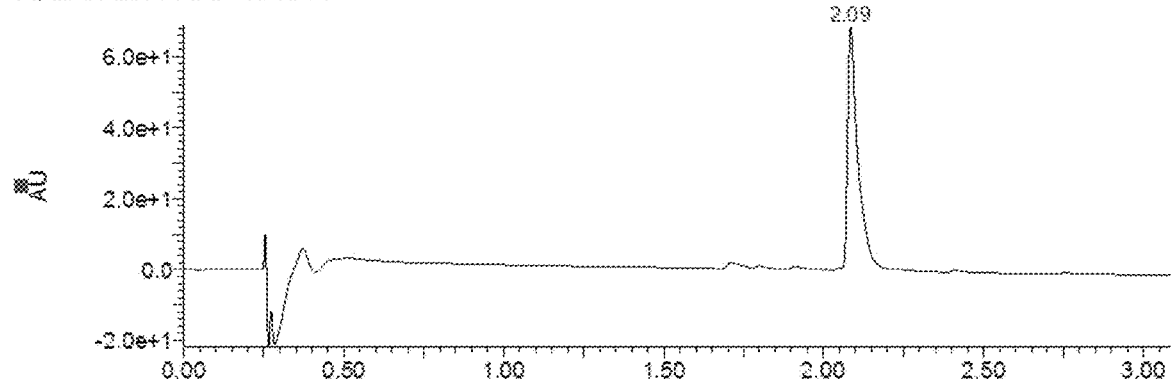
FIG. 26 is a U-HPLC chromatogram for compound 5j (purity 96%) [% product peak area/impurity peak areas].
Figure 27:
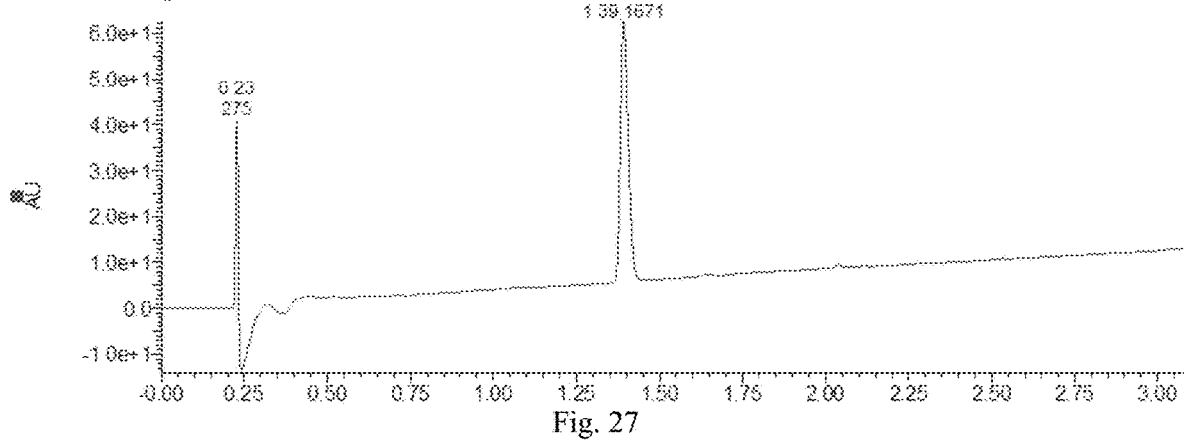
FIG. 27 is a U-HPLC chromatogram for compound 9a (purity 98%) [% product peak area/impurity peak areas].
Figure 28:
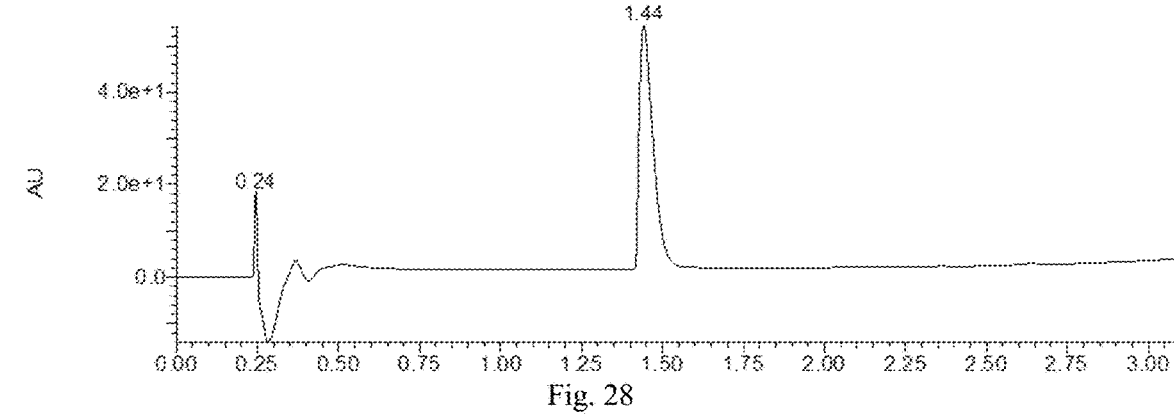
FIG. 28 is a U-HPLC chromatogram for compound 9b (purity 99%) [% product peak area/impurity peak areas].
Figure 29:
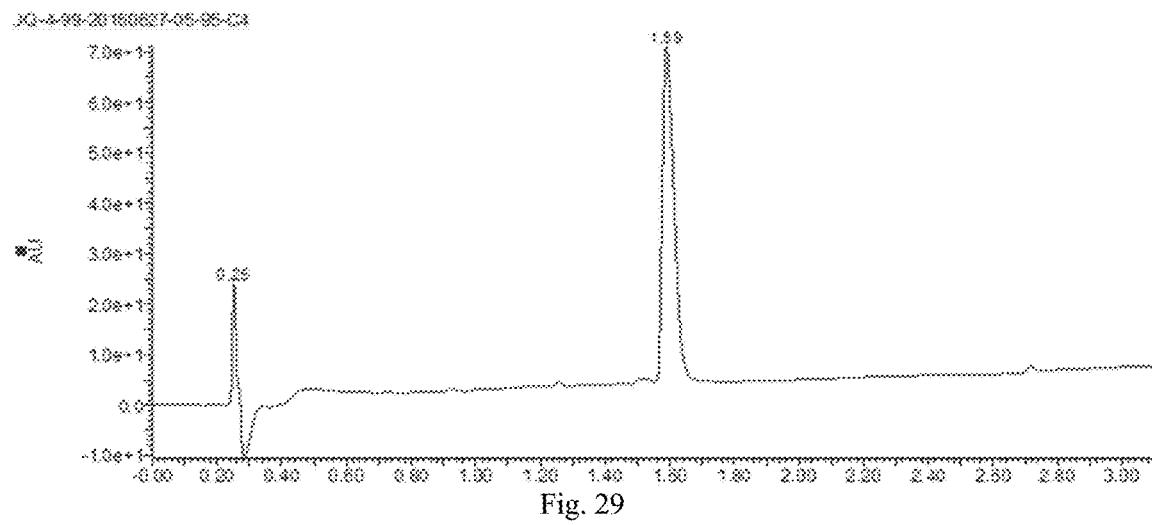
FIG. 29 is a U-HPLC chromatogram for compound 10a (purity 98%) [% product peak area/impurity peak areas].
Figure 30:
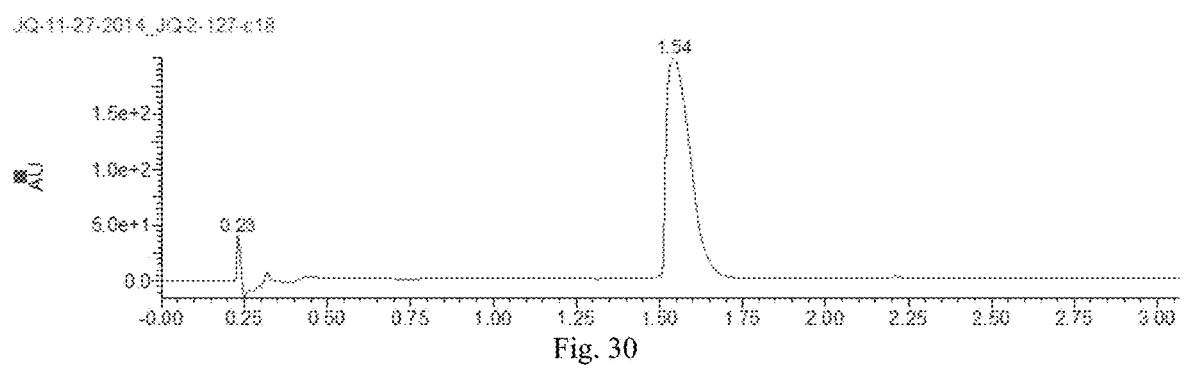
FIG. 30 is a U-HPLC chromatogram for compound 10b (purity 99%) [% product peak area/impurity peak areas].
Figure 31:
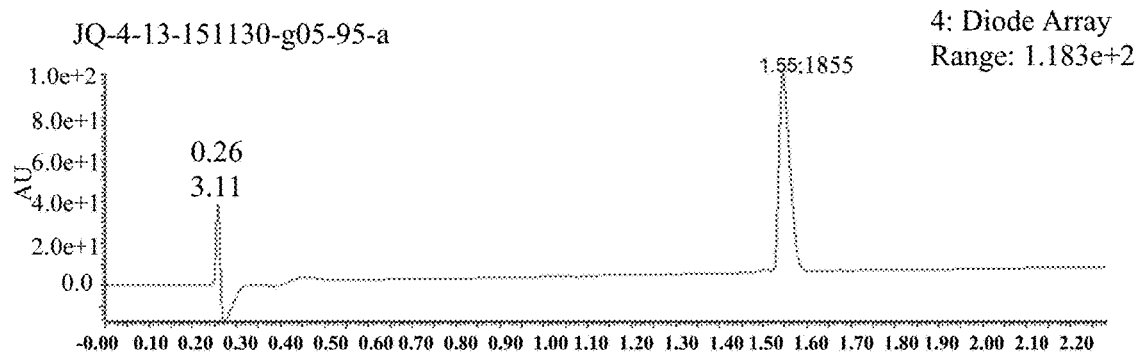
FIG. 31 is a U-HPLC chromatogram for compound 10c (purity 99%) [% product peak area/impurity peak areas].
Figure 32:
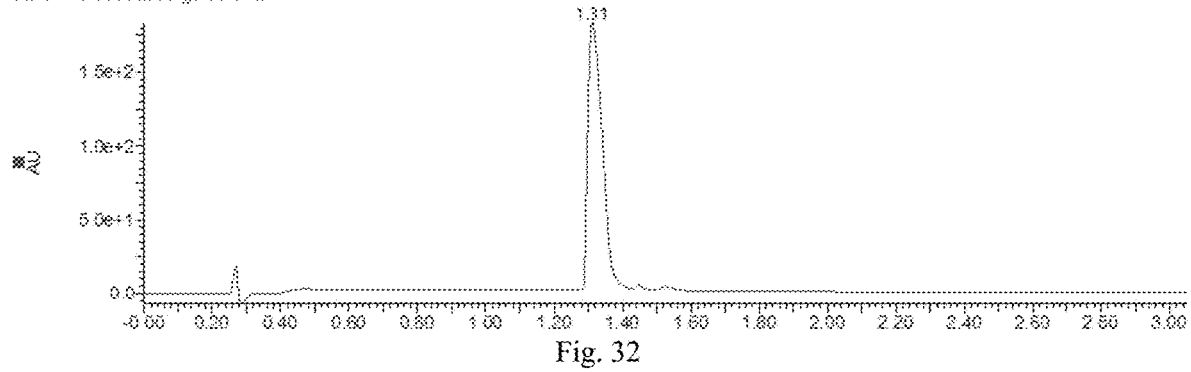
FIG. 32 is a U-HPLC chromatogram for compound 14a (purity 97%) [% product peak area/impurity peak areas].
Figure 33:
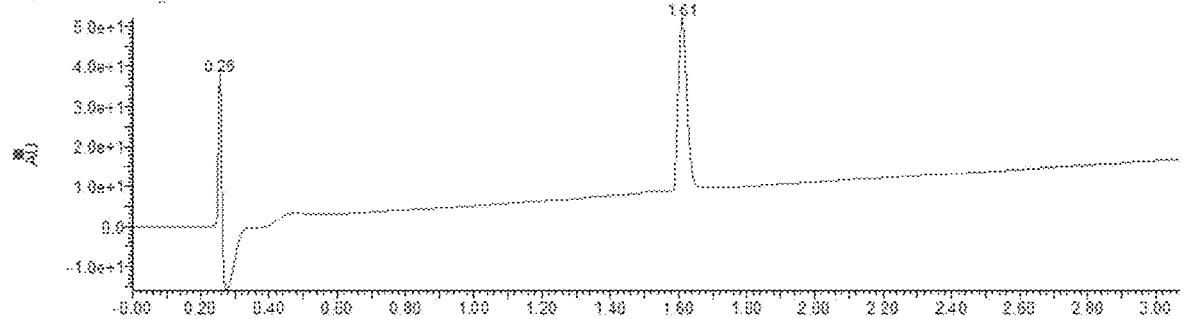
FIG. 33 is a U-HPLC chromatogram for compound 14b (purity 99%) [% product peak area/impurity peak areas].
Figure 34:
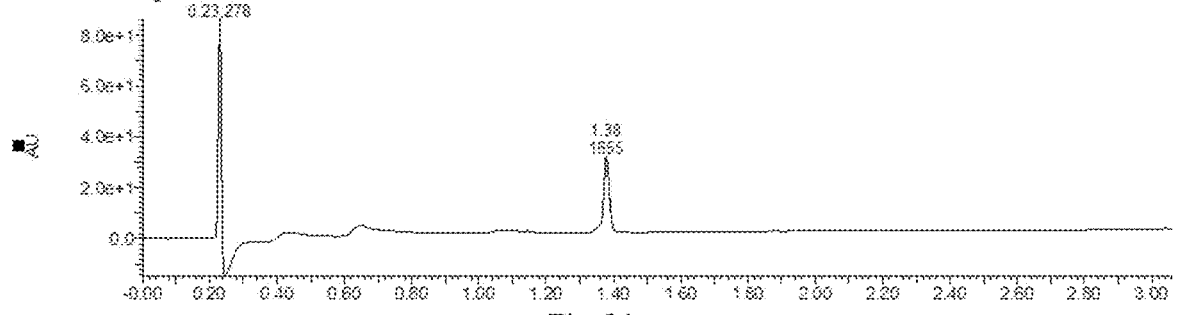
FIG. 34 is a U-HPLC chromatogram for compound 15a (purity 97%) [% product peak area/impurity peak areas].
Figure 35:
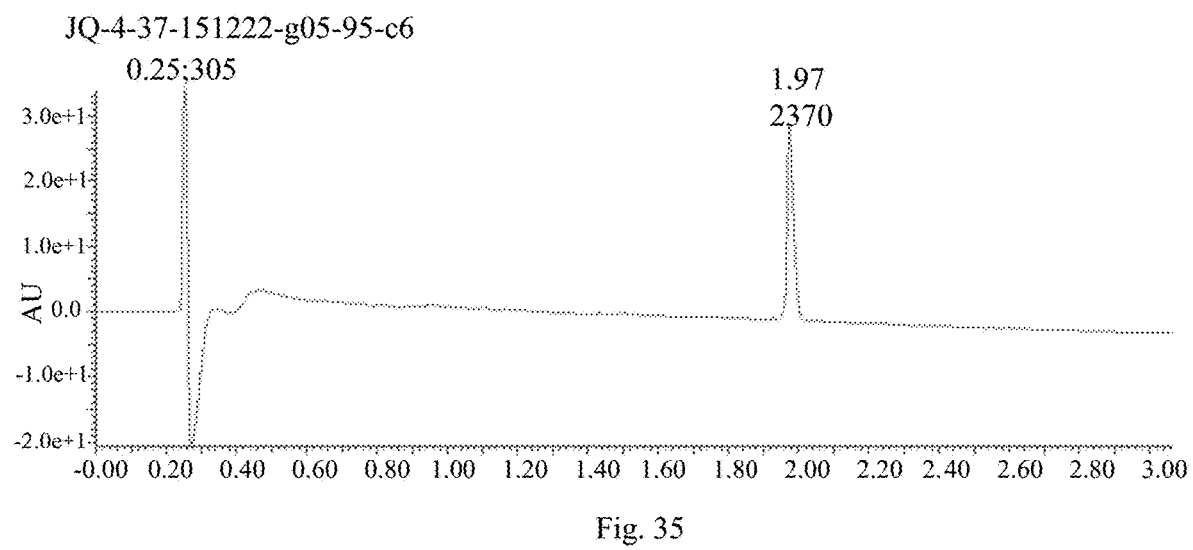
FIG. 35 is a U-HPLC chromatogram for compound 15b (purity 99%) [% product peak area/impurity peak areas].
Figure 36:
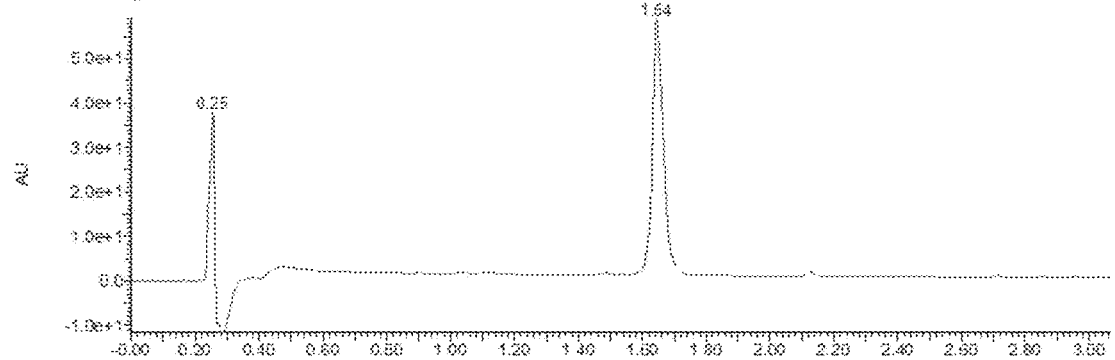
FIG. 36 is a U-HPLC chromatogram for compound 17a (purity 99%) [% product peak area/impurity peak areas].
Figure 37:
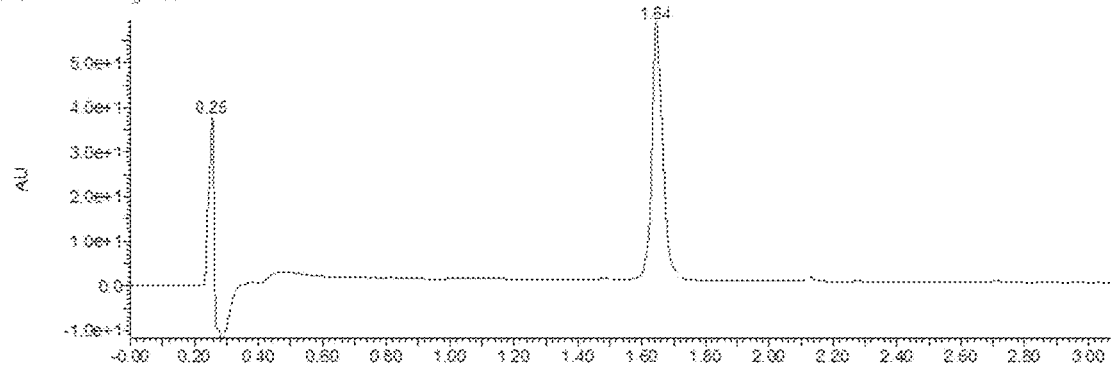
FIG. 37 is a U-HPLC chromatogram for compound 17b (purity 98%) [% product peak area/impurity peak areas].
Figure 38:
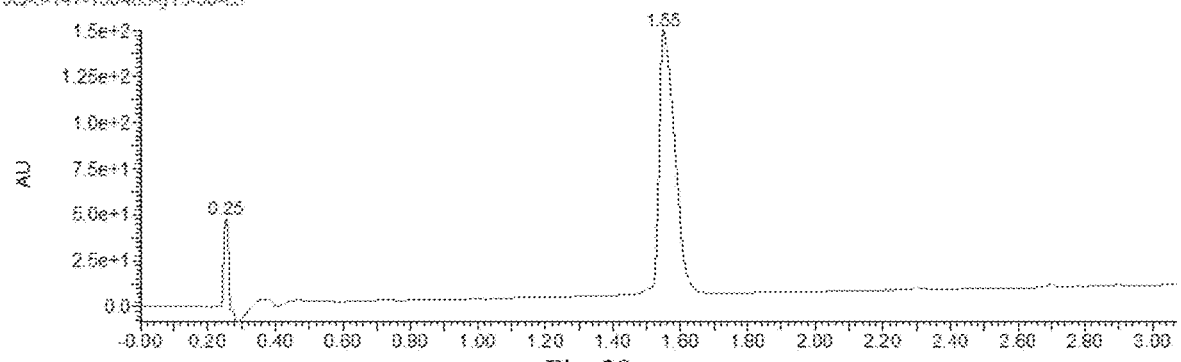
FIG. 38 is a U-HPLC chromatogram for compound 19 (purity 99%) [% product peak area/impurity peak areas].
Figure 39:
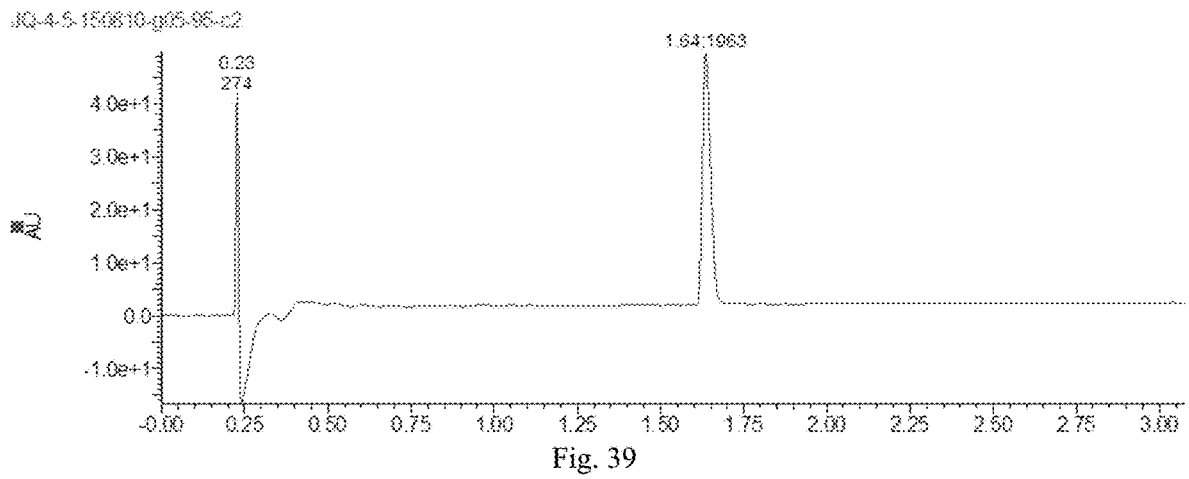
FIG. 39 is a U-HPLC chromatogram for compound 20 (purity 96%) [% product peak area/impurity peak areas].
Figure 40:
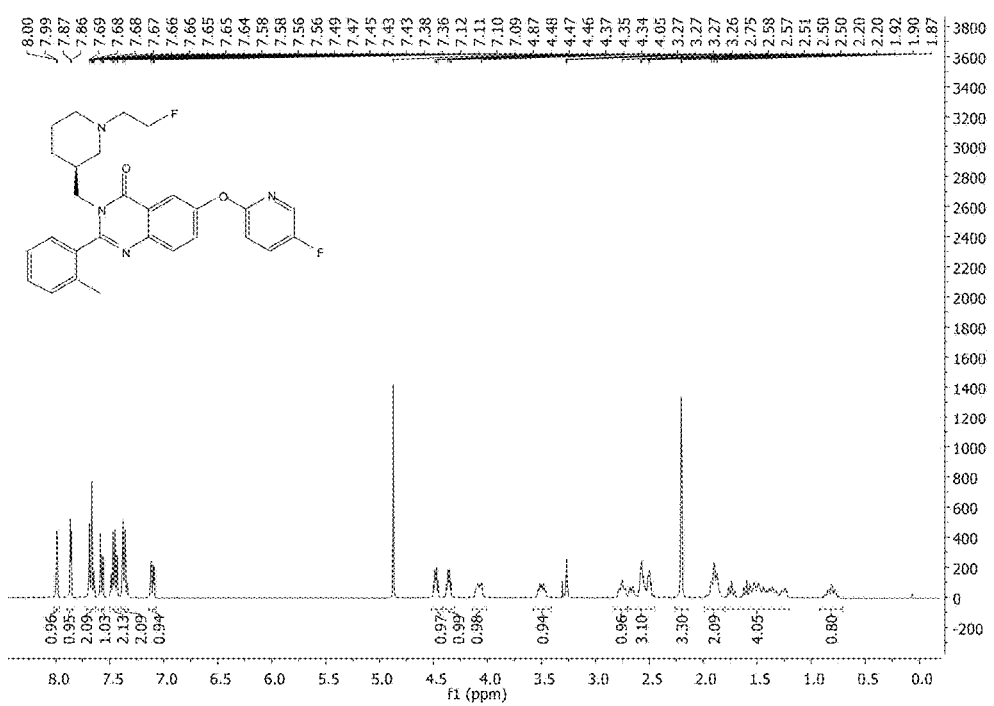
FIG. 40 is a 1H NMR spectrum for 5b.
Figure 41:
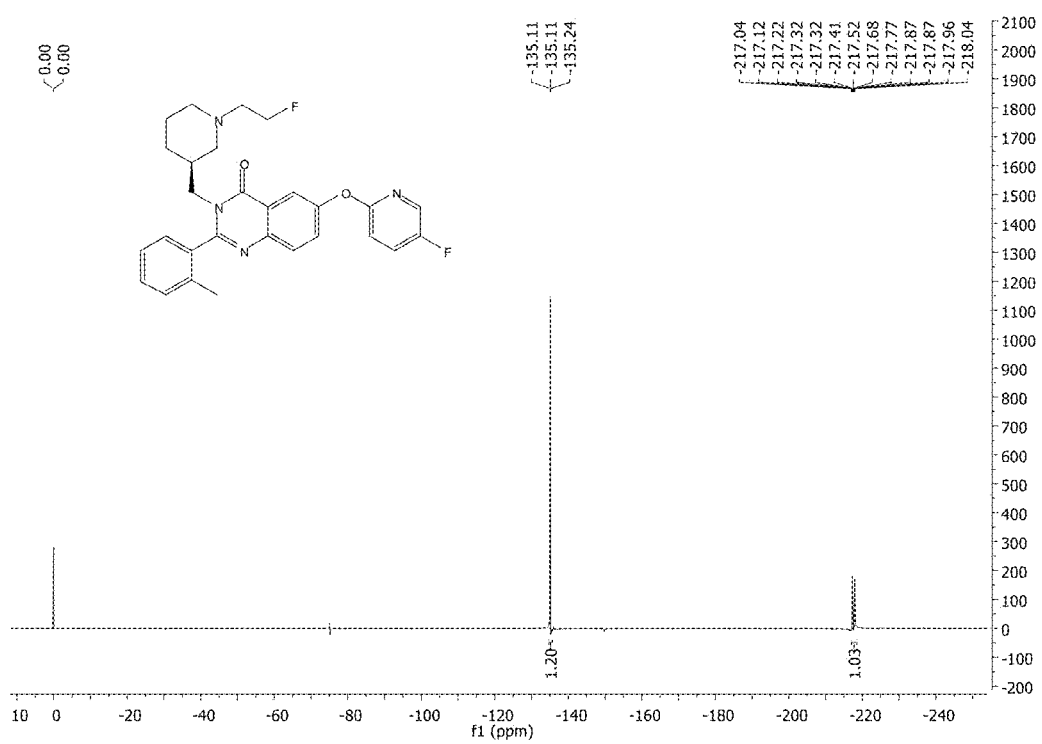
FIG. 41 is a 19F NMR spectrum for 5b.

FIG. 10 illustrates stacked HPLC chromatograms (λ=254 nm) (bottom curve) and radio chromatograms (top curve) for 17b and [$^{18}$F]17b.

FIGS. 18, 21, 23, 25, 30, 38, and 39 show U-HPLC chromatogram and purity of compounds 5b, 5e, 5g, 5i, 10b, 19 and 20.

FIGS. 40, 41, 45, 46, 51, 52, 53, and 54 show $^1$H and $^{19}$F NMR spectrum of compounds 5b, 10b, 19 and 20.

Figure 42:
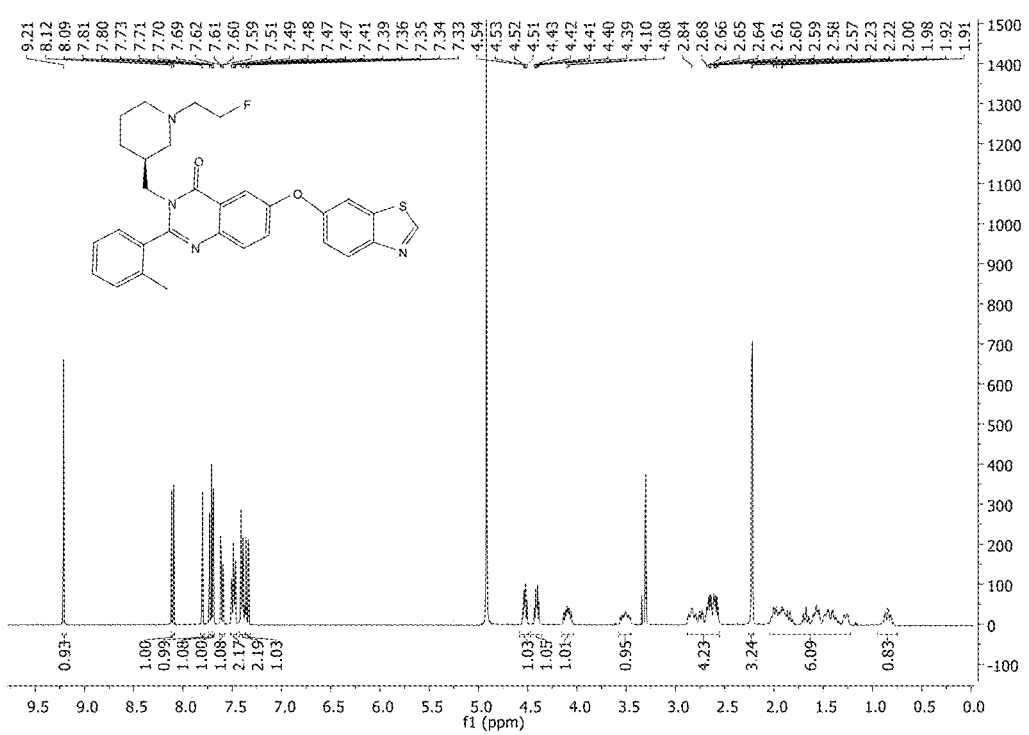
FIG. 42 is a 1H NMR spectrum for 5e.
Figure 43:
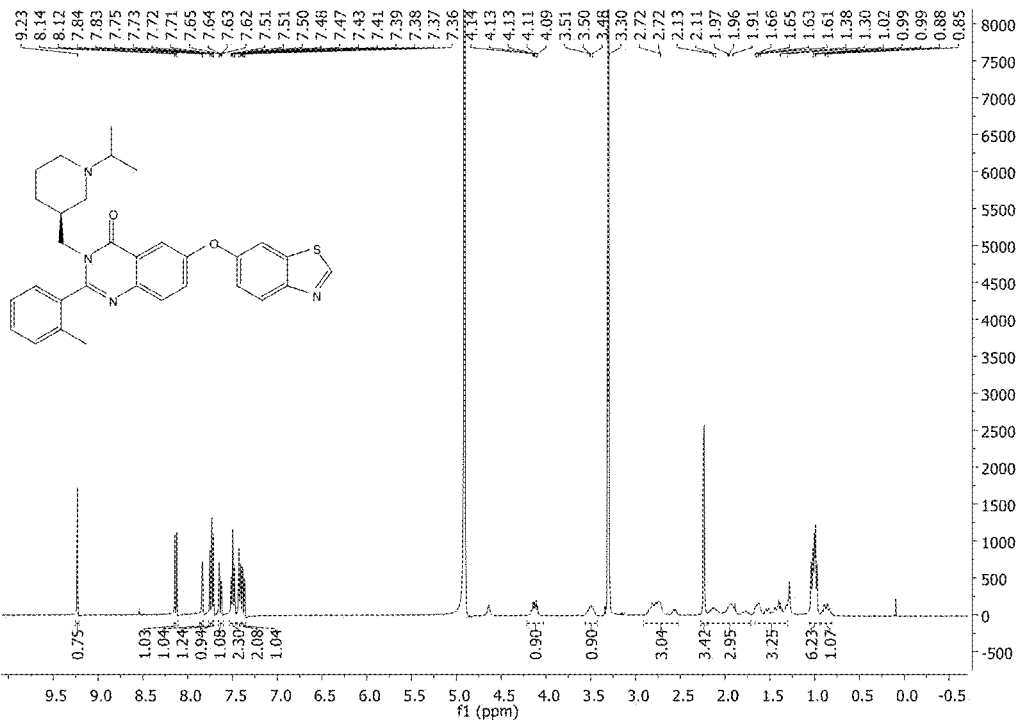
FIG. 43 is a 1H NMR spectrum for 5g.
Figure 44:
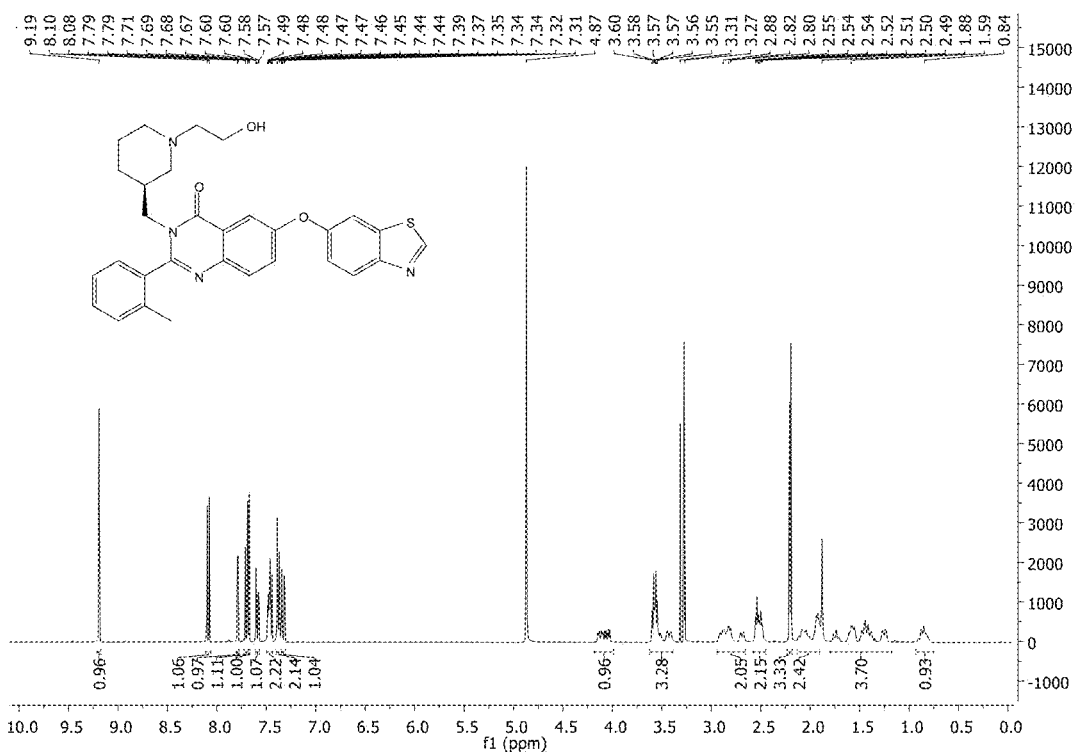
FIG. 44 is a 1H NMR spectrum for 5i.
Figure 45:
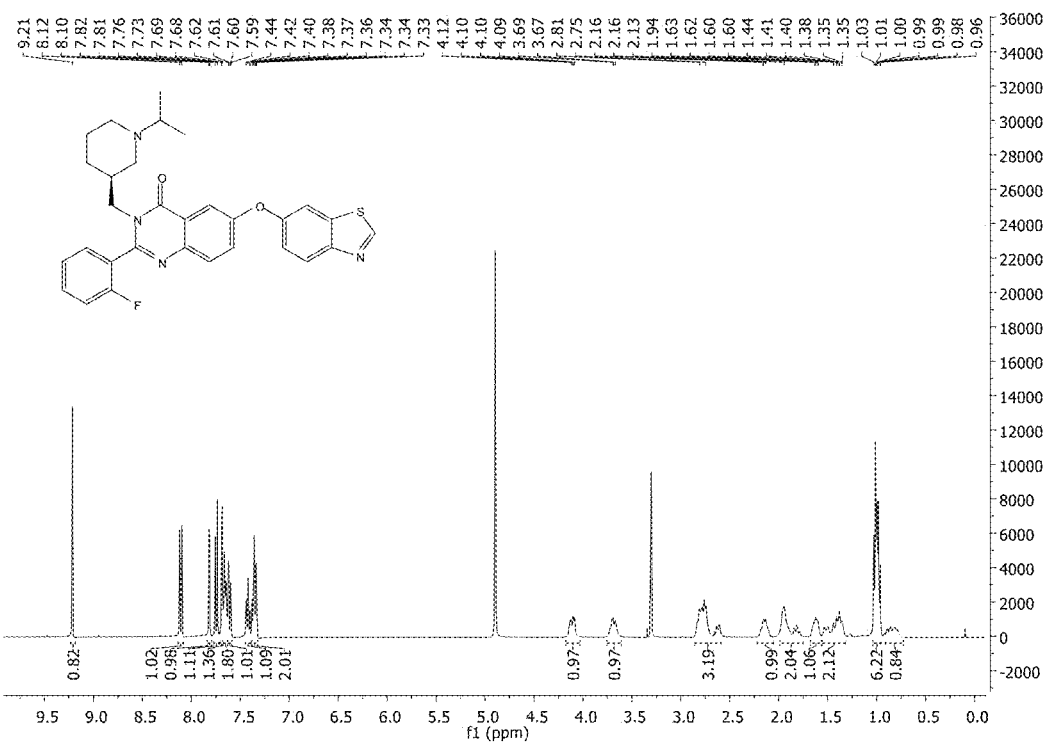
FIG. 45 is a 1H NMR spectrum for 10b.
Figure 46:
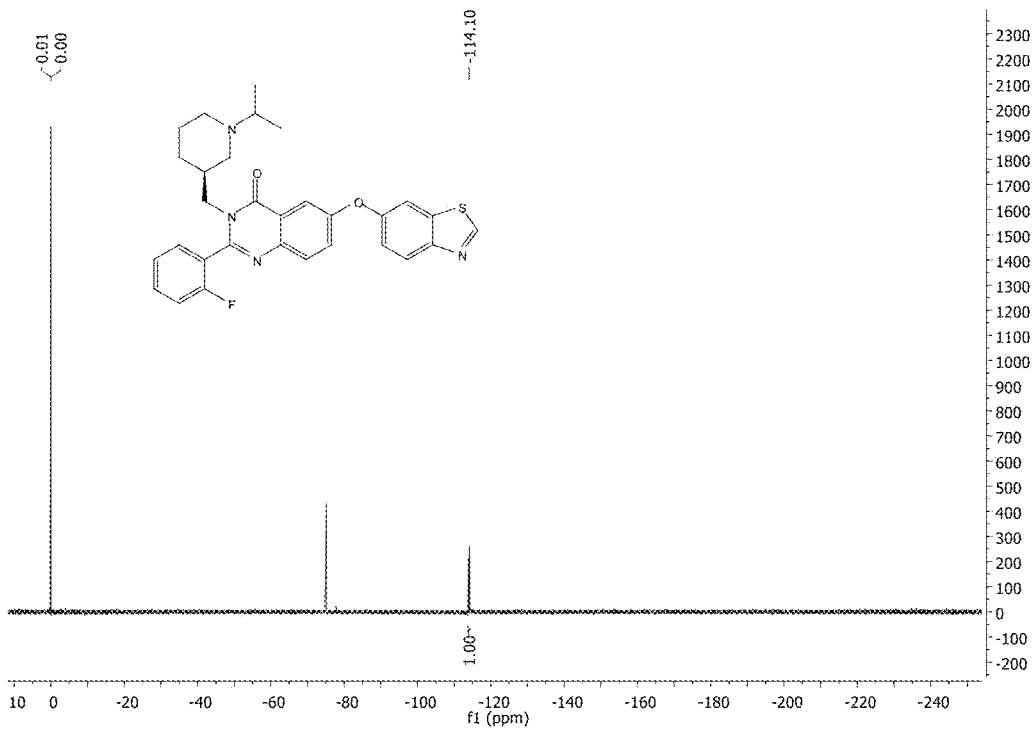
FIG. 46 is a 19F NMR spectrum for 10b.
Figure 47:
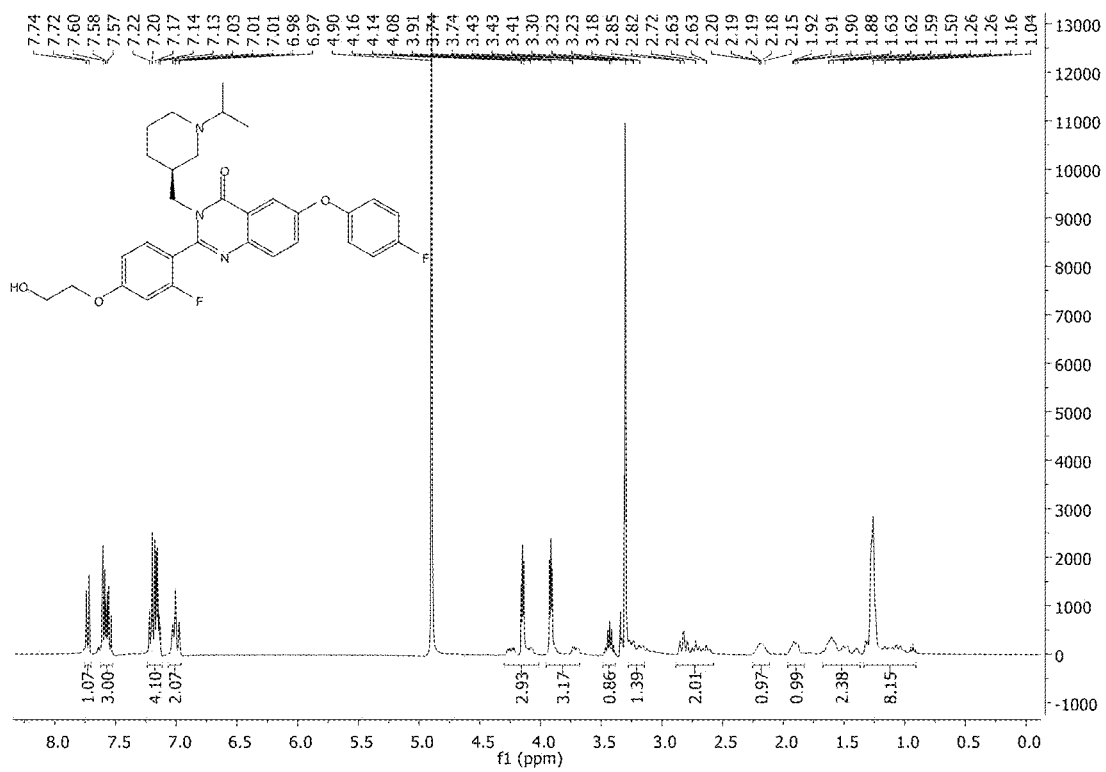
FIG. 47 is a 1H NMR spectrum for 15b.
Figure 48:
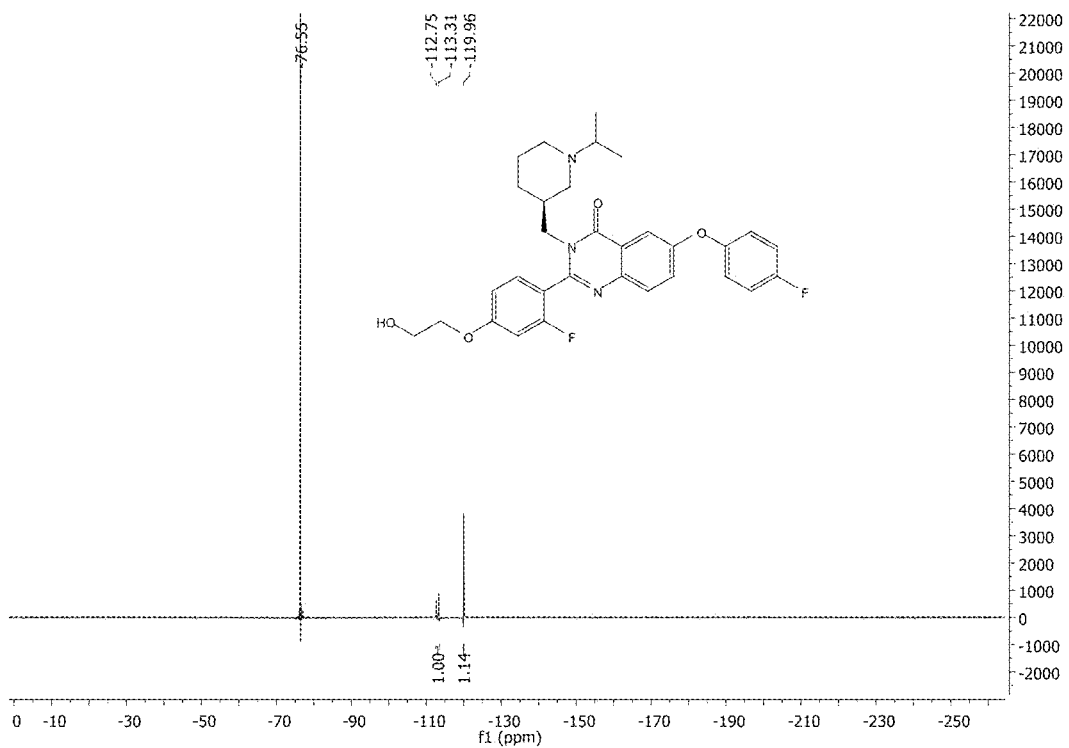
FIG. 48 is a 19F NMR spectrum for 15b.
Figure 49:
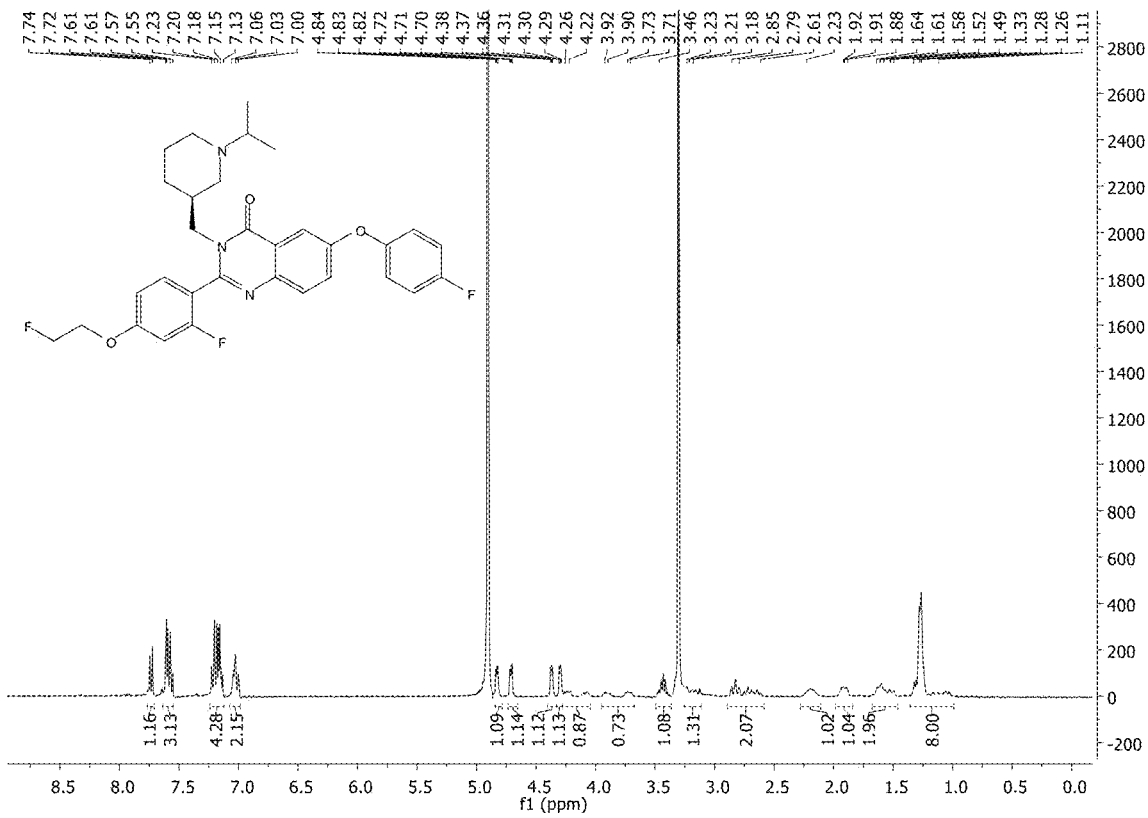
FIG. 49 is a 1H NMR spectrum for 17b.
Figure 50:
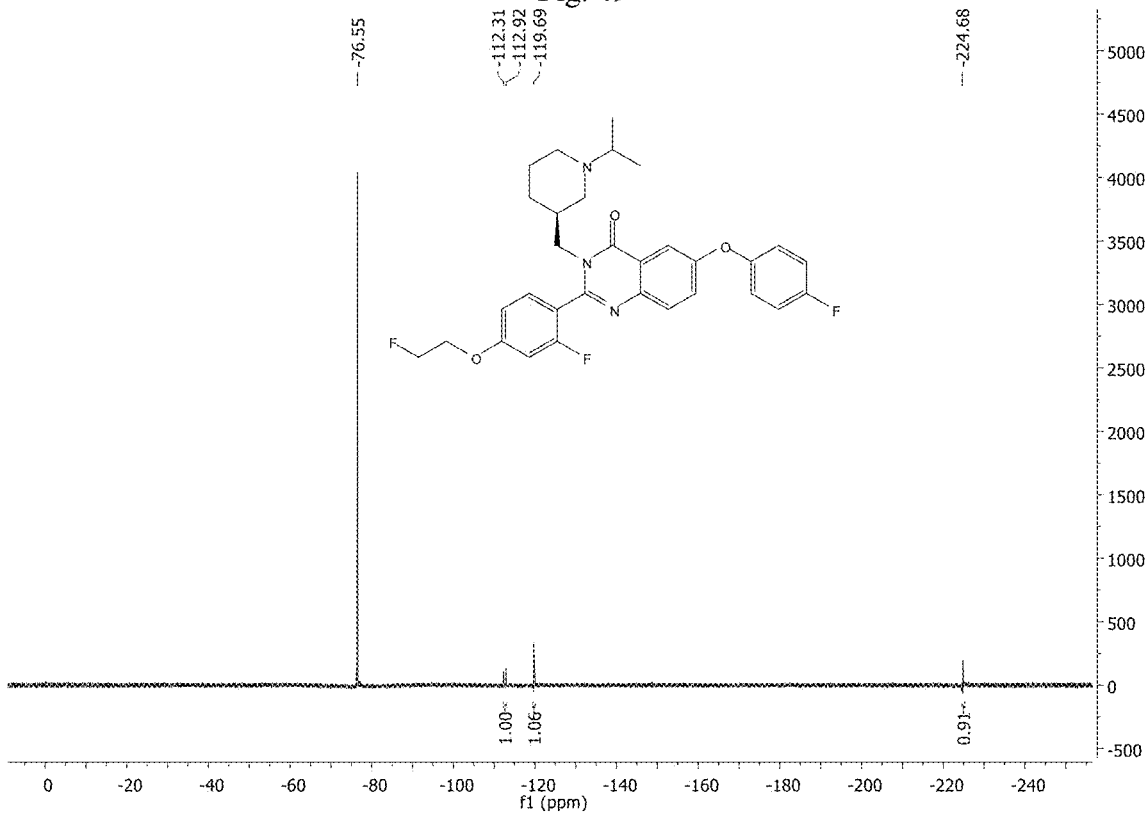
FIG. 50 is a 19F NMR spectrum for 17b.
Figure 51:
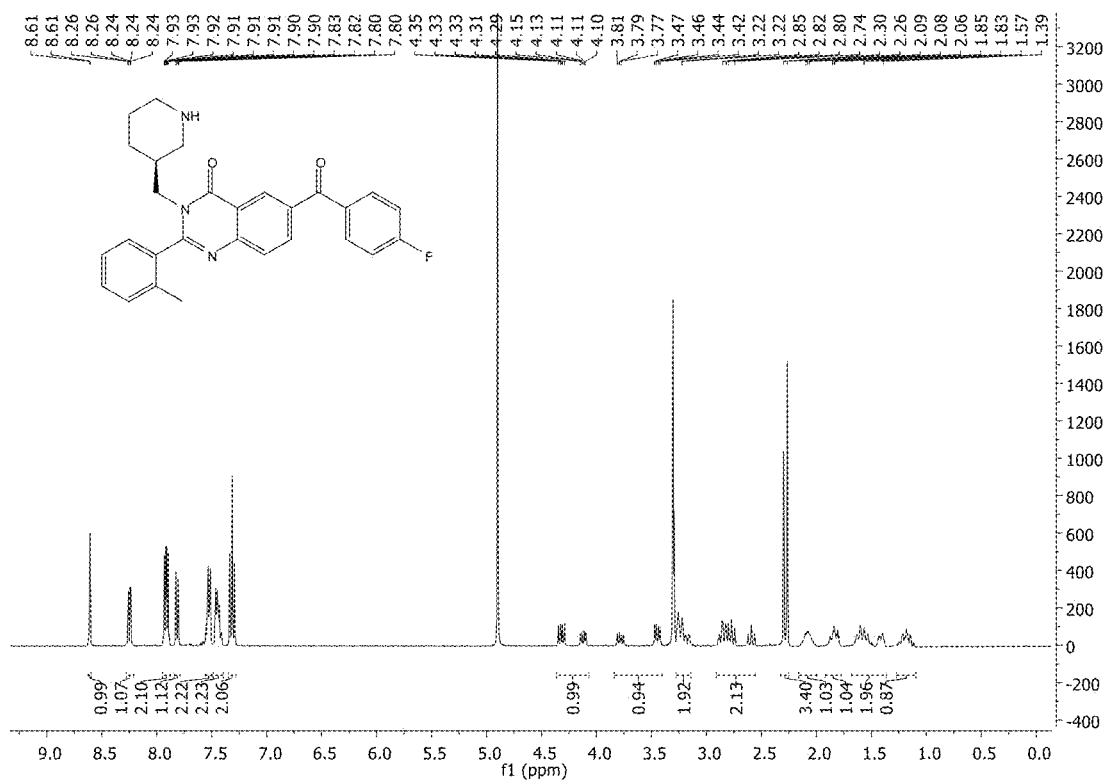
FIG. 51 is a 1H NMR spectrum for 19.
Figure 52:
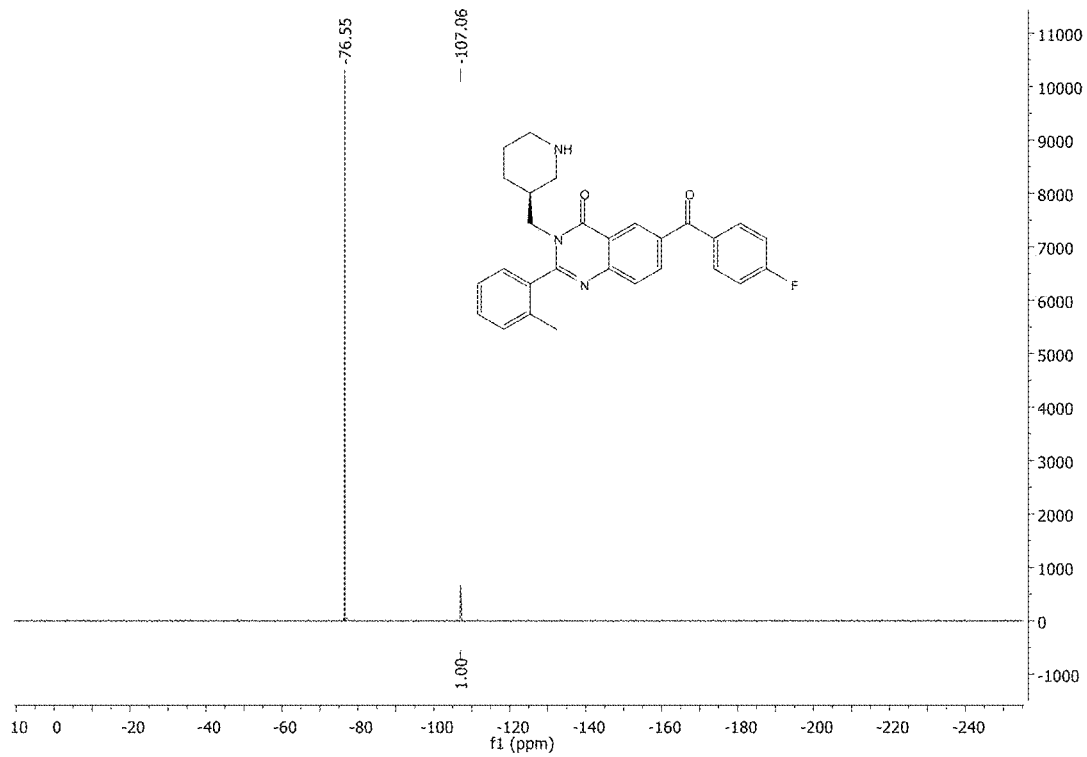
FIG. 52 is a 19F NMR spectrum for 19.
Figure 53:
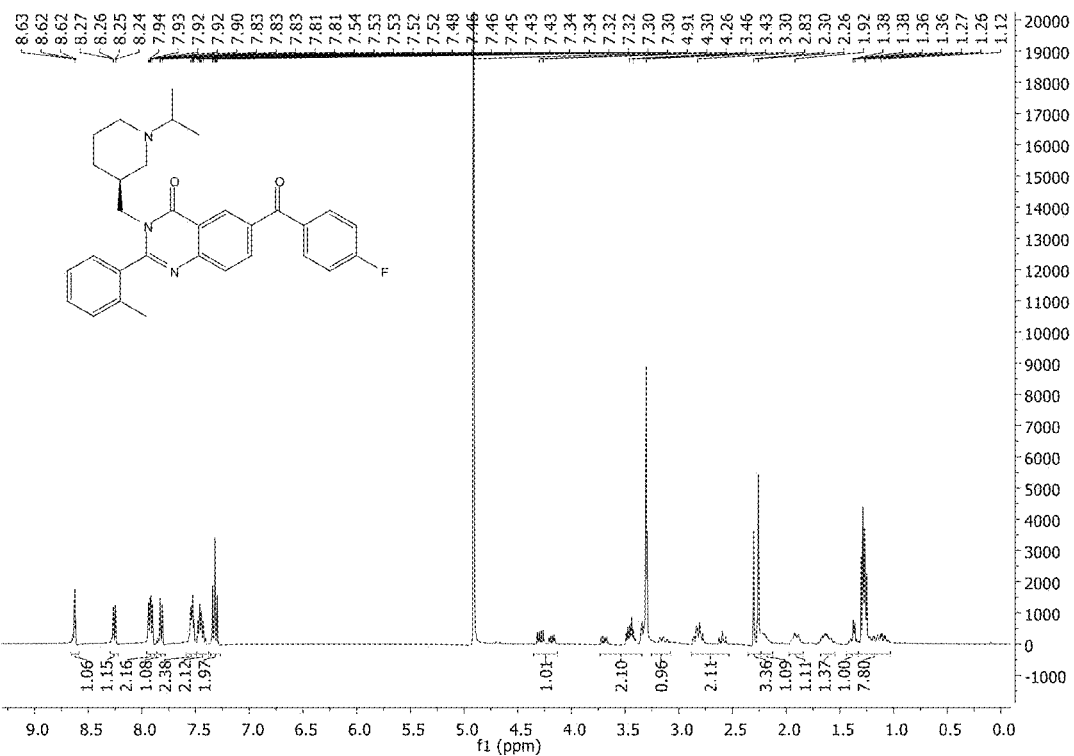
FIG. 53 is a 1H NMR spectrum for 20.
Figure 54:
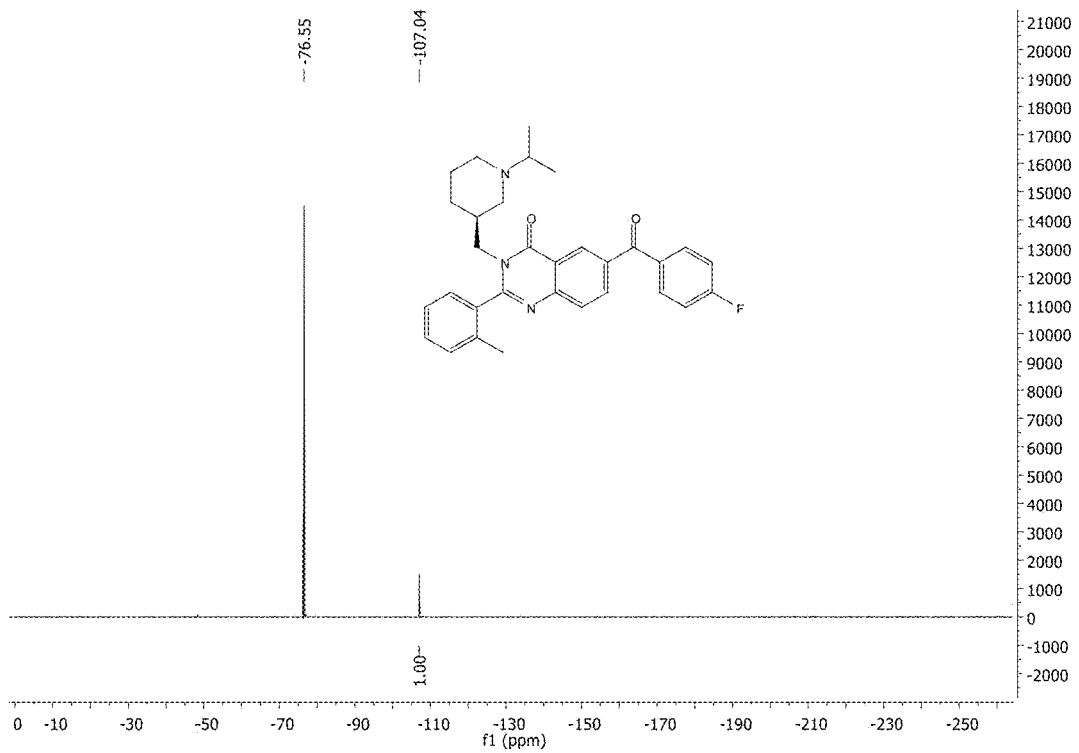
FIG. 54 is a 19F NMR spectrum for 20.
Figure 55:
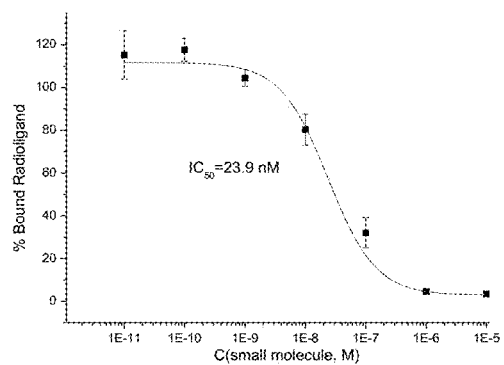
FIG. 55 is a binding curve for 5b.
Figure 56:
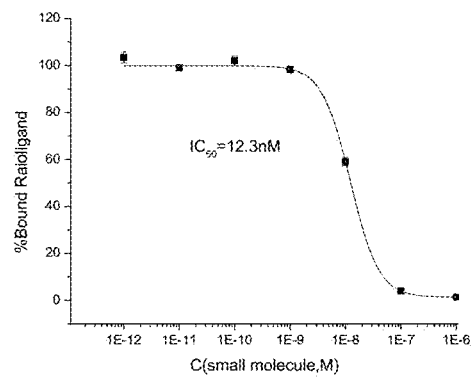
FIG. 56 is a binding curve for 5e.
Figure 57:
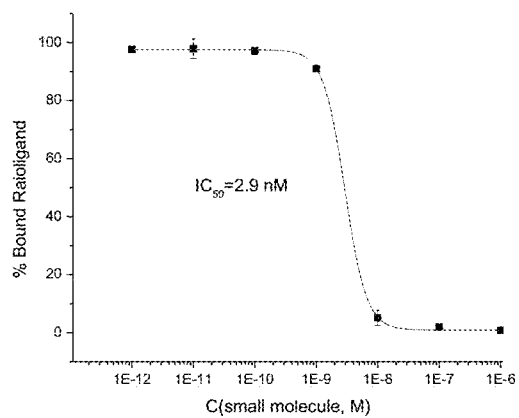
FIG. 57 is a binding curve for 5g.
Figure 58:
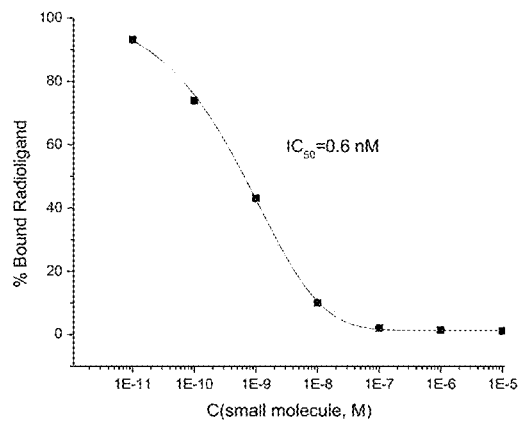
FIG. 58 is a binding curve for 5i.
Figure 59:
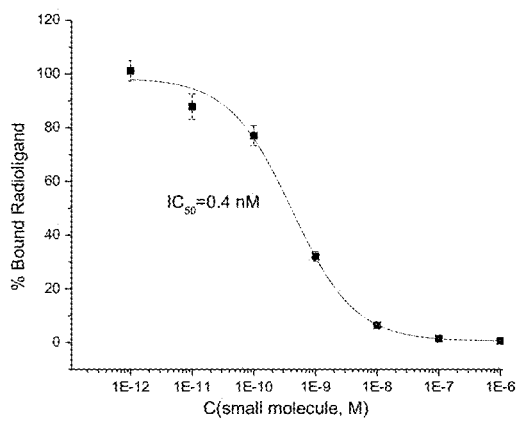
FIG. 59 is a binding curve for 10b.
Figure 60:
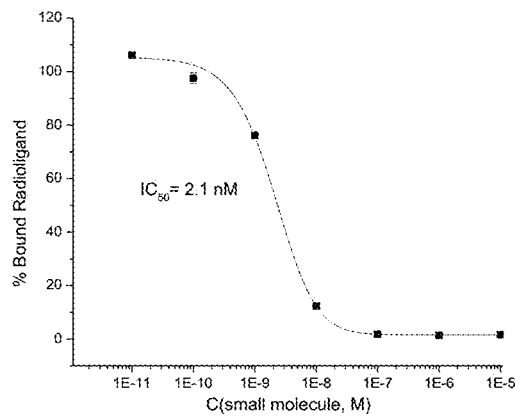
FIG. 60 is a binding curve for 15b.
Figure 61:
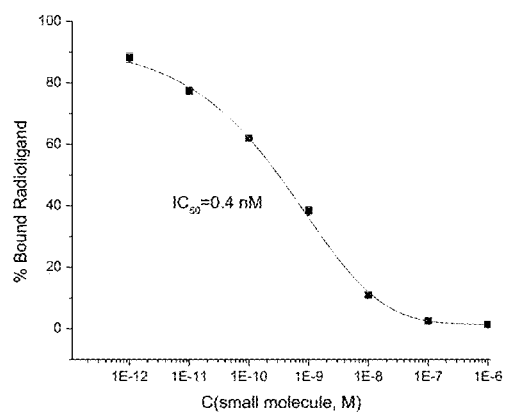
FIG. 61 is a binding curve for 17b.
Figure 62:
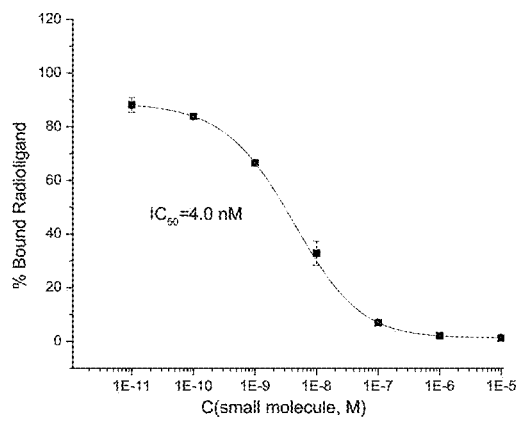
FIG. 62 is a binding curve for 19.
Figure 63:
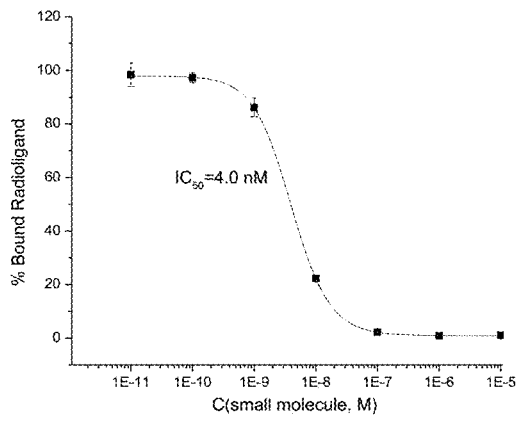
FIG. 63 is a binding curve for 20.
Figure 64:
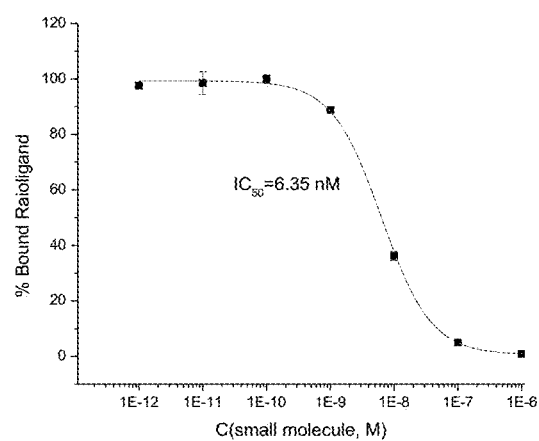
FIG. 64 is a binding curve for natural ghrelin.
Figure 65:
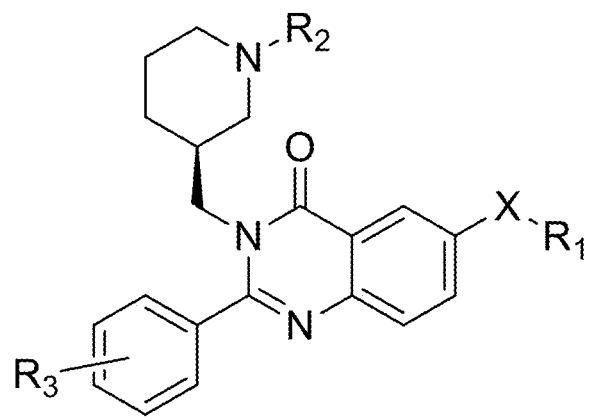
FIG. 65 is the chemical structure of general formula I.

FIGS. 42, 43, and 44 show $^1$H spectra of compounds 5e, 5g and 5i.

Methods

Synthesis of the 1$^{st}$ Serial of the Compounds 6-bromo-2-(o-tolyl)-4H-benzo[d][1,3]oxazin-4-one (1,JQ-2-67)

The compound was made according to literature procedures with some modifications. o-Toluoyl chloride (10.0 g, 64.7 mmol) was added slowly into a solution of 5-Bromoanthranilic Acid (12.7 g, 58.8 mmol) and triethylamine (24.6 mL, 176.4 mmol) in DCM (120 mL) at 0° C. The reaction mixture was stirred at room temperature (rt) for 16 h. After the solvent was removed under reduced pressure, water (80 ml) and DCM (80 ml) were added into the resulting product (yellow oil). The organic layer was washed with additional 80 ml of water, dried over $Na_2SO_4$ and filtered. Acetic anhydride (50 mL) was added in to the filtrate and the sk0olution was heated at 50° C. for 3 h. The reaction mixture was cooled to rt, diluted with DCM. Saturated $NaHCO_3$ was added slowly. The layer was separated and the organic layer was washed with brine, dried over $Na_2SO_4$ and filtered. The filtrate was concentrated under reduced pressure and the crude product was treated with ethanol and stirred for 10 mins. The solid was filtered and washed with additional ethanol, and then air dried for 3 h to give 13 g of the product with 70% yield. UP LC-MS (waters) method: 5-90% acetonitrile (0.1% TFA) in water (0.1% TFA), 3 mins run, RT (min) 2.58, m/z 316.9467; RT (min) 2.58.

(R)-tert-butyl 3-((5-bromo-2-(2-methylbenzamido) benzamido)methyl)piperidine-1-carboxylate (2,JQ-2-71)

The compound was made according to literature procedure with some modifications. Compound 1 (3 g, 9.5 mmol) was dissolved in toluene (20 ml). (R)-1-Boc-3-(aminomethyl)pyrrolidine (2.4 g, 11.4 mmol) was added and the solution was refluxed at 110° C. for 8 h. The resulting solution was cooled down at rt. The solvent was removed by around 90% and hexane (20 ml) was added. The precipitate was filtered out and washed with additional 10 ml hexane to give 4.9 g pure product. Yield: 97%; UP LC-MS (waters) method: 50-90% acetonitrile (0.1% TFA) in water (0.1% TFA), 3 mins run; Calculated m/z 530.1654 (MH$^+$), Found m/z: 530.1379; RT (min) 2.19.

(R)-tert-butyl 3-((6-bromo-4-oxo-2-(o-tolyl)quinazolin-3(4H)-yl)methyl)piperidine-1-carboxylate (3,JQ-2-129)

Compound 2a (2.50 g, 4.72 mmol) was added to microwave reaction vessel followed by ethylene glycol (12 mL) and LiOH (0.22 mg, 9.17 mmol). The resulting mixture was subjected to microwave irradiation with stirring for 30 minutes at 150° C., cooled to rt, and diluted with $CH_2Cl_2$ (50 ml) and water (50 ml). The organic layer was washed with brine (50 mL) twice. The combined organic layer was dried over $Mg_2SO_4$ and then concentrated under reduced pressure. Purification via silica gel column chromatography using a gradient elution from 25 to 50% ethyl acetate in hexanes to yield 1.93 g the product, Yield: 82%. UP LC-MS (waters) method: 50-90% acetonitrile (0.1% TFA) in water (0.1% TFA), 3 mins run; Calculated m/z 512.1549 (MH$^+$), Found m/z: 512.1022; RT (min) 1.86.

(S)-6-(4-fluorophenoxy)-3-(piperidin-3-ylmethyl)-2-(o-tolyl)quinazolin-4(3H)-one (4a,JQ-2-143)

The compound was made according to literature procedure with some modifications. Under a nitrogen atmosphere, compound 3a (512 mg, 1.00 mmol), copper(I) iodine (95 mg, 0.05 mmol), 2,2,6,6-tetramethylheptane-3,5-dione (TMHD) (46 mg, 0.25 mmol), 4-fluorophenol (168 mg, 1.5 mmol) and $Cs_2CO_3$ (652 mg, 2.00 mmol) were added to 1-methyl-2-pyrrolidone (2 mL). The reaction mixture was stirred for 16 h at 120° C., cooled, and filtered through Celite. The filtrate was concentrated under reduced pressure and purified via silica gel column chromatography using a gradient elution from 10 to 20% ethyl acetate in hexanes to give 300 mg of the product (Yield: 55%). The above product (300 mg, 0.55 mmol) was dissolved in $CH_2Cl_2$ (5 mL), followed by TFA (2 mL). The solution was stirred for 4 h at rt. The solvent was removed and saturated aqueous $NaHCO_3$ solution was added. The product was then extracted with EtOAc (2×). The combined organic layers were dried with $Na_2SO_4$ and filtered, and the solvent was removed under reduced pressure, and the crude compound was purified by reverse phase chromatography (Isolera One, HS—C18-30 g cartridge) with a gradient from 5 to 60% MeOH in water. It was lyophilized to give desired product as white powder with 85% yield. UP LC-MS (waters) method: 5-95% acetonitrile (0.1% TFA) in water (0.1% TFA), 3 mins run, RT (min) 1.65, Found m/z: 444.1. HRMS (ES$^+$) for $C_{27}H_{27}FN_3O_2$ (MH$^+$), calcd 444.2087; found 444.2094. $^1$H NMR (400 MHz, methanol-$d_4$) δ ppm 7.69 (d, J=8.9 Hz, 1H), 7.60 (d, J=2.7, 1H), 7.54 (dd, J=8.9, 2.7 Hz, 1H), 7.46-7.50 (m, 2H), 7.41-7.37 (m, 2H), 7.22-7.10 (m, 4H), 4.19-3.93 (m, 1H), 3.64-3.35 (m, 1H), 2.86-2.83 (m, 1H), 2.80-2.62 (m, 1H), 2.46-2.37 (m, 1H), 2.23-2.07 (m, 4H), 1.80-1.72 (m, 1H), 1.60-1.27 (m, 3H), 1.06-0.90 (m, 1H). $^{19}$F NMR (376 MHz, methanol-$d_4$) δ ppm −118.76--118.66 (m).

(S)-3-((1-(2-fluoroethyl)piperidin-3-yl)methyl)-6-(4-fluorophenoxy)-2-(o-tolyl)quinazolin-4(3H)-one (5a,JQ-1-47)

Compound 4a (160 mg, 0.36 mmol), 1-Fluoro-2-idoethane (313 mg, 1.80 mmol), and $K_2CO_3$ (200 mg, 1.45 mmol) were combined in acetonitrile (10 ml) and heated to 70° C. for 8 h. The solid was filtered off, and the filtrate was concentrated under reduced pressure. Saturated aqueous $NaHCO_3$ solution was added, and the product was extracted with EtOAc (2×). The combined organic layers were dried with $Na_2SO_4$ and filtered. The solvent was removed under reduced pressure, and the crude product was purified via silica gel column chromatography (2% MeOH in DCM) to give 80 mg of the product, Yield: 45%. UP LC-MS (waters) method: 20-60% acetonitrile (0.1% TFA) in water (0.1% TFA), 3 mins run, RT (min) 1.93, m/z 490.2. HRMS (ES$^+$) for $C_{29}H_{30}F_2N_3O_2$ (MH$^+$), calcd 490.2306; found 490.2308. $^1$H NMR (400 MHz, methanol-$d_4$) δ ppm 7.70 (d, J=8.9 Hz, 1H), 7.62 (d, J=2.9 Hz, 1H), 7.56 (dd, J=8.9, 2.9 Hz, 1H), 7.51-7.46 (m, 2H), 7.42-7.37 (m, 2H), 7.23-7.11 (m, 4H), 4.56-4.46 (m, 1H), 4.44-4.35 (m, 1H), 4.14-4.04 (m, 1H), 3.57-3.43 (m, 1H), 2.84-2.51 (m, 4H), 2.23 (d, J=2.5 Hz, 3H), 2.00-1.84 (m, 2H), 1.82-1.22 (m, 4H), 0.93-0.76 (m, 1H).

(S)-6-((5-fluoropyridin-2-yl)oxy)-3-(piperidin-3-ylmethyl)-2-(o-tolyl)quinazolin-4(3H)-one (4b,JQ-2-49)

The method similar for the preparation of compound 4a was used, except replacing 4-fluorophenol with 5-fluoro-2-pyridinol. The Boc-protected intermediate was purified via silica gel column chromatography using a gradient elution from 20 to 30% ethyl acetate in hexane and gave 44% yield. After Boc deprotection, the crude compound was purified by reverse phase chromatography (Isolera One, HS—C18-30 g cartridge) with a gradient from 30 to 100% MeOH in water. The product was lyophilized and obtained with 67% yield. UP LC-MS (waters) method: 5-95% acetonitrile (0.1% TFA) in water (0.1% TFA), 3 mins run, RT (min) 2.01, Found m/z: 445.2. HRMS (ES$^+$) for $C_{26}H_{26}FN_4O_2$ (MH$^+$), calcd 445.2040; found 445.2046. $^1$H NMR (400 MHz, methanol-$d_4$) δ ppm 8.04 (d, J=3.2 Hz, 1H), 7.90 (d, J=2.7 Hz, 1H), 7.75-7.68 (m, 2H), 7.62 (dd, J=8.9, 2.7 Hz, 1H), 7.53-7.46 (m, 2H), 7.44-7.37 (m, 2H), 7.15 (dd, J=8.9, 3.2 Hz, 1H), 4.23-3.99 (m, 1H), 3.66-3.37 (m, 1H), 2.90-2.65 (m, 2H), 2.41 (qd, J=11.9, 2.8 Hz, 1H), 2.27-2.07 (m, 4H), 1.85-1.72 (m, 1H), 1.64-1.24 (m, 3H), 1.10-0.90 (m, 1H).

(S)-3-((1-(2-fluoroethyl)piperidin-3-yl)methyl)-6-((5-fluoropyridin-2-yl)oxy)-2-(o-tolyl)quinazolin-4(3H)-one (5b,JQ-2-55)

The method similar for the preparation of compound 5a was used, except replacing compound 4a with 4b. The compound was purified by reverse phase chromatography (Isolera One, HS—C18-30 g cartridge) with a gradient from 30 to 100% MeOH in water. The product was lyophilized to give white power with 72% yield. UP LC-MS (waters) method: 5-95% acetonitrile (0.1% TFA) in water (0.1% TFA), 3 mins run, RT (min) 1.46, Found m/z: 491.2. HRMS (ESI$^+$) for $C_{28}H_{29}F_2N_4O_2$ (MH$^+$), calcd 491.2259, found 491.2260. $^1$H NMR (400 MHz, methanol-d4) δ ppm 7.99 (d, J=3.2 Hz, 1H), 7.86 (d, J=2.7 Hz, 1H), 7.71-7.63 (m, 2H), 7.57 (dd, J=8.8, 2.7 Hz, 1H), 7.50-7.42 (m, 2H), 7.39-7.33 (m, 2H), 7.10 (dd, J=9.0, 3.2 Hz, 1H), 4.48 (dd, J=11.5, 5.3 Hz, 1H), 4.36 (dd, J=11.5, 5.3 Hz, 1H), 4.14-4.01 (m, 1H), 3.58-3.41 (m, 1H), 2.75 (t, J=11.0 Hz, 1H), 2.71-2.45 (m, 3H), 2.20 (d, J=2.1 Hz, 3H), 1.90 (t, J=11.0 Hz, 2H), 1.80-1.21 (m, 4H), 0.92-0.71 (m, 1H). $^{19}$F NMR (376 MHz, methanol-$d_4$) δ ppm −134.69--135.69 (m, 1F), −217.01--218.50 (m, 1F).

(S)-6-((6-fluoropyridin-3-yl)oxy)-3-(piperidin-3-ylmethyl)-2-(o-tolyl)quinazolin-4(3H)-one (4c,JQ-2-21)

The method similar for the preparation of compound 4a was used, except replacing 4-fluorophenol with 6-fluoropyridin-3-ol. The Boc-protected intermediate was purified via silica gel column chromatography using elution of 30% ethyl acetate in hexane and gave 44% yield. After Boc deprotection, the crude compound was purified via aluminium oxide column chromatography using a gradient elution from 2 to 5% methanol in dichloromethane to give 95% yield. UP LC-MS (waters) method: 5-95% acetonitrile (0.1% TFA) in water (0.1% TFA), 3 mins run, RT (min) 1.25, m/z 445.2. HRMS (ESI$^+$) for $C_{26}H_{26}FN_4O_2$ (MH$^+$), calcd 445.2040, found 445.2047. $^1$H NMR (400 MHz, methanol-d4) δ ppm 8.07 (d, J=2.9 Hz, 1H), 7.79-7.72 (m, 2H), 7.70 (d, J=2.9 Hz, 1H), 7.63 (dd, J=8.9, 2.9 Hz, 1H), 7.53-7.46 (m, 2H), 7.44-7.37 (m, 2H), 7.17 (dd, J=9.2, 2.9 Hz, 1H), 4.22-4.00 (m, 1H), 3.65-3.38 (m, 1H), 2.86 (d, J=12.0 Hz, 1H), 2.82-2.64 (m, 1H), 2.43 (q, J=12.0 Hz, 1H), 2.28-2.08 (m, 4H), 1.83-1.73 (m, 1H), 1.62-1.24 (m, 3H), 1.06-0.93 (m, 1H).

(S)-3-((1-(2-fluoroethyl)piperidin-3-yl)methyl)-6-((6-fluoropyridin-3-yl)oxy)-2-(o-tolyl)quinazolin-4(3H)-one (5c,JQ-2-39)

The method similar for the preparation of compound 5a was used, except replacing compound 4a with 4c. The crude compound was purified by reverse phase chromatography (Isolera One, HS—C18-30 g cartridge) with a gradient from 5 to 100% MeOH in water. The product was lyophilized to give white power with 45% yield. UP LC-MS (waters) method: 5-95% acetonitrile (0.1% TFA) in water (0.1% TFA), 3 mins run, RT (min) 1.39, Found m/z: 491.2. HRMS (ESI$^+$) for $C_{28}H_{29}F_2N_4O_2$ (MH$^+$), calcd 491.2259, found 491.2259. $^1$H NMR (400 MHz, methanol-d4) δ ppm 8.07 (d, J=3.0 Hz, 1H), 7.78-7.72 (m, 2H), 7.69 (d, J=2.9 Hz, 1H), 7.62 (dd, J=8.9, 2.9 Hz, 1H), 7.52-7.46 (m, 2H), 7.44-7.37 (m, 2H), 7.16 (dd, J=8.8, 3.0 Hz, 1H), 4.56-4.46 (m, 1H), 4.46-4.33 (m, 1H), 4.11 (dt, J=13.9, 7.0 Hz, 1H), 3.64-3.43 (m, 1H), 2.86-2.53 (m, 4H), 2.23 (d, J=2.9 Hz, 3H), 2.01-1.84 (m, 2H), 1.85-1.23 (m, 4H), 0.93-0.75 (m, 1H). $^{19}$F NMR (376 MHz, methanol-d4) δ ppm −73.85 (s, 1F), −217.04−−218.61 (m, 1F)

(S)-6-((6-((5-fluoropyridin-2-yl)oxy)pyridin-3-yl)oxy)-3-(piperidin-3-ylmethyl)-2-(o-tolyl)quinazolin-4(3H)-one (4d,JQ-2-29)

Compound 4d was synthesized as a side product during the preparation of compound 4c with a yield of 34%. UP LC-MS (waters) method: 10-90% acetonitrile (0.1% TFA) in water (0.1% TFA), 3 mins run, RT (min) 1.48, Found m/z: 538.2. HRMS (ESI$^+$) for $C_{31}H_{29}FN_5O_3$ (MH$^+$), calcd 538.2254, found 538.2255. $^1$H NMR (400 MHz, methanol-d4) δ ppm 8.10 (s, 1H), 7.99 (d, J=2.9 Hz, 1H), 7.86-7.79 (m, 1H), 7.72 (d, J=8.8 Hz, 2H), 7.64 (d, J=2.9 Hz, 1H), 7.61 (dd, J=8.8, 2.9 Hz, 1H), 7.52-7.45 (m, 2H), 7.44-7.36 (m, 2H), 7.20 (d, J=8.8 Hz, 1H), 7.13 (dd, J=8.8, 2.9 Hz, 1H), 4.20-3.96 (m, 1H), 3.65-3.36 (m, 1H), 2.84 (d, J=11.9 Hz, 1H), 2.81-2.62 (m, 1H), 2.47-2.34 (m, 1H), 2.25-2.06 (m, 4H), 1.81-1.69 (m, 1H), 1.60-1.24 (m, 3H), 1.04-0.92 (m, 1H).

(S)-6-((6-((5-fluoropyridin-2-yl)oxy)pyridin-3-yl)oxy)-3-((1-(2-hydroxyethyl)piperidin-3-yl)methyl)-2-(o-tolyl)quinazolin-4(3H)-one (5d,JQ-2-37)

Compound 5d was purified by flash column chromatography (Al$_2$O) with a gradient elution from 1 to 2% methanol in DCM and was lyophilized to give the desire product with 23% yield. UP LC-MS (waters) method: 5-95% acetonitrile (0.1% TFA) in water (0.1% TFA), 3 mins run, RT (min) 1.46, Found m/z: 582.3. HRMS (ESI$^+$) for $C_{33}H_{33}FN_5O_4$ (MH$^+$), calcd 582.2517, found 582.2512. $^1$H NMR (400 MHz, methanol-d$_4$) δ ppm 8.10 (dd, J=2.8, 1.4 Hz, 1H), 7.99 (d, J=3.0 Hz, 1H), 7.86-7.79 (m, 1H), 7.74-7.69 (m, 2H), 7.68-7.64 (m, 1H), 7.64-7.59 (m, 1H), 7.54-7.47 (m, 2H), 7.44-7.38 (m, 2H), 7.20 (dd, J=8.8, 4.4 Hz, 1H), 7.14 (dd, J=8.9, 3.1 Hz, 1H), 4.24-4.03 (m, 1H), 3.70-3.41 (m, 3H), 3.08-2.77 (m, 2H), 2.73-2.59 (m, 2H), 2.31-1.90 (m, 6H), 1.72-1.61 (m, 1H), 1.59-1.24 (m, 2H), 1.00-0.86 (m, 1H).

(S)-6-(benzo[d]thiazol-6-yloxy)-3-(piperidin-3-ylmethyl)-2-(o-tolyl)quinazolin-4(3H)-one (4e,JQ-2-35)

The method similar for the preparation of compound 4a was used, except replacing 4-fluorophenol with 6-bezothiazolol. The Boc-protected intermediate was purified via silica gel column chromatography using an elution of 25% ethyl acetate in hexane and gave 14% yield. After Boc deprotection, the crude compound was purified via reverse phase chromatography (Isolera One, HS—C18-30 g cartridge) with a gradient from 30 to 100% MeOH in water. The product was lyophilized to give white power with 90% yield. UP LC-MS (waters) method: 5-95% acetonitrile (0.1% TFA) in water (0.1% TFA), 3 mins run, RT (min) 1.43, m/z 483.2. HRMS (ESI$^+$) for $C_{28}H_{27}N_4O_2S$ (MH$^+$), calcd 483.1855, found 483.1855. $^1$H NMR (400 MHz, methanol-d4) δ ppm 9.23 (s, 1H), 8.12 (d, J=8.9 Hz, 1H), 7.82 (d, J=2.3 Hz, 1H), 7.75 (dd, J=8.9, 1.4 Hz, 1H), 7.71-7.68 (m, 1H), 7.67-7.61 (m, 1H), 7.54-7.47 (m, 2H), 7.46-7.39 (m, 2H), 7.35 (dd, J=8.9, 2.3 Hz, 1H), 4.34-4.03 (m, 1H), 3.78-3.32 (m, 1H), 3.26-3.09 (m, 2H), 2.89-2.78 (m, 1H), 2.77-2.51 (m, 1H), 2.29-2.18 (m, 3H), 2.10-1.94 (m, 1H), 1.88-1.76 (m, 1H), 1.63-1.31 (m, 2H), 1.23-1.05 (m, 1H).

(S)-6-(benzo[d]thiazol-6-yloxy)-3-((1-(2-fluoroethyl)piperidin-3-yl)methyl)-2-(o-tolyl)quinazolin-4(3H)-one (5e,JQ-2-45)

The method similar for the preparation of compound 5a was used, except replacing compound 4a with 4e, for synthesis of compound 5e as a white power with a yield of 47%. UP LC-MS (waters) method: 5-95% acetonitrile (0.1% TFA) in water (0.1% TFA), 3 mins run, RT (min) 1.49, m/z 529.2. HRMS (ESI$^+$) for $C_{30}H_{30}FN_4O_2S$ (MH$^+$), calcd 529.2074, found 529.2073. $^1$H NMR (400 MHz, methanol-d4) δ ppm 9.21 (s, 1H), 8.10 (d, J=8.9 Hz, 1H), 7.80 (d, J=2.4 Hz, 1H), 7.72 (d, J=8.8 Hz, 1H), 7.69 (d, J=2.8 Hz, 1H), 7.60 (dd, J=8.8, 2.8 Hz, 1H), 7.52-7.45 (m, 2H), 7.43-7.37 (m, 2H), 7.35 (dd, J=8.9, 2.4 Hz, 1H), 4.58-4.49 (m, 1H), 4.47-4.35 (m, 1H), 4.15-4.03 (m, 1H), 3.58-3.45 (m, 1H), 2.88-2.55 (m, 4H), 2.22 (d, J=3.8 Hz, 3H), 2.04-1.22 (m, 6H), 0.95-0.75 (m, 1H). $^{19}$F NMR (376 MHz, methanol-d4) δ ppm −218.50 (s).−217.80−−219.41 (m, 1F)

(S)-6-(4-(4-acetylpiperazin-1-yl)phenoxy)-3-(piperidin-3-ylmethyl)-2-(o-tolyl)quinazolin-4(3H)-one (4f,JQ-2-95)

The method similar for the preparation of compound 4a was used, except replacing 4-fluorophenol with 1-acetyl-4-(4-hydroxyphenyl)piperazine. The Boc-protected intermediate was purified via reverse phase chromatography (Isolera One, HS—C18-30 g cartridge) with a gradient from 0 to 100% MeOH in water and gave 7% yield. After Boc deprotection, the crude compound was purified via reverse phase chromatography (Isolera One, HS—C18-30 g cartridge) with a gradient from 8 to 80% MeOH in water. The product was lyophilized to give white power with 90% yield. UP LC-MS (waters) method: 5-95% acetonitrile (0.1% TFA) in water (0.1% TFA), 3 mins run, RT (min) 1.38, m/z: 552.3. HRMS (ESI$^+$) for $C_{33}H_{38}FN_5O_3$ (MH$^+$), calcd 552.2975, found 552.2968. $^1$H NMR (400 MHz, methanol-d4) δ ppm 7.68 (d, J=9.3 Hz, 1H), 7.59-7.52 (m, 2H), 7.52-7.46 (m, 2H), 7.46-7.38 (m, 2H), 7.13-7.02 (m, 4H), 4.34-4.01 (m, 1H), 3.78-3.34 (m, 5H), 3.25-3.07 (m, 6H), 2.89-2.51 (m, 2H), 2.27-2.18 (m, 3H), 2.18-2.13 (m, 3H), 2.02 (s, 1H), 1.89-1.76 (m, 1H), 1.63-1.32 (m, 2H), 1.23-1.06 (m, 1H).

(S)-6-(4-fluorophenoxy)-3-((1-isopropylpiperidin-3-yl)methyl)-2-(o-tolyl)quinazolin-4(3H)-one (5f,JQ-1-39)

The compound was made according to literature procedure. UP LC-MS (waters) method: 20-80% acetonitrile (0.1% TFA) in water (0.1% TFA), 3 mins run, RT (min) 1.86, m/z: 486.2. HRMS (ESI$^+$) for $C_{30}H_{33}FN_3O_2$ (MH$^+$), calcd 486.2557, found 486.2556. $^1$H NMR (400 MHz, methanol-d$_4$) δ ppm 7.70 (d, J=8.9 Hz, 1H), 7.63 (d, J=2.9 Hz, 1H), 7.57 (dd, J=8.9, 2.9 Hz, 1H), 7.53-7.45 (m, 2H), 7.44-7.38 (m, 2H), 7.23-7.12 (m, 4H), 4.25-4.04 (m, 1H), 3.62-3.41 (m, 1H), 2.97-2.59 (m, 3H), 2.30-1.88 (m, 6H), 1.73-1.58 (m, 1H), 1.58-1.27 (m, 2H), 1.14-0.97 (m, 6H), 0.97-0.77 (m, 1H). $^{19}$F NMR (376 MHz, methanol-d$_4$) δ ppm −120.24−−120.39 (m, 1F).

(S)-6-(benzo[d]thiazol-6-yloxy)-3-((1-isopropylpiperidin-3-yl)methyl)-2-(o-tolyl)quinazolin-4(3H)-one (5g,JQ-4-15)

The method similar for the preparation of compound 5e was used, except replacing compound 1-fluoro-2-iodoethane with 2-bromopropane. Compound 5e was purified by reverse phase chromatography (Isolera One, HS—C18-30 g cartridge) with a gradient elution from 5 to 80% methanol (0.1% TFA) in water (0.1% TFA), and was lyophilized to give the desire product with 90% yield. UP LC-MS (waters) method: 5-95% acetonitrile (0.1% TFA) in water (0.1% TFA), 3 mins run, RT (min) 1.95, Found m/z: 525.1328. HRMS (ESI$^+$) for $C_{31}H_{33}N_4O_2S$ (MH$^+$), calcd 525.2324, found 525.2327. $^1$H NMR (400 MHz, methanol-d$_4$) δ ppm 9.23 (s, 1H), 8.13 (d, J=8.9 Hz, 1H), 7.84 (d, J=2.4 Hz, 1H), 7.74 (d, J=8.9 Hz, 1H), 7.71 (d, J=2.9 Hz, 1H), 7.64 (dd, J=8.9, 2.9 Hz, 1H), 7.53-7.47 (m, 2H), 7.45-7.39 (m, 2H), 7.38 (dd, J=8.9, 2.4 Hz, 1H), 4.21-4.03 (m, 1H), 3.56-3.41 (m, 1H), 2.91-2.52 (m, 3H), 2.24 (d, J=4.0 Hz, 3H), 2.18-2.05 (m, 1H), 2.00-1.72 (m, 2H), 1.67-1.58 (m, 1H), 1.44-1.27 (m, 2H), 1.06-0.94 (m, 6H), 0.93-0.81 (m, 1H).

(S)-6-((6-fluoropyridin-3-yl)oxy)-3-((1-(2-hydroxyethyl)piperidin-3-yl)methyl)-2-(o-tolyl)quinazolin-4(3H)-one (5h,JQ-3-59)

Compound 4c (200 mg, 0.45 mmol) was dissolved in dichloromethane (60 ml), 2-bromoethanol (288 mg, 2.25 mmol) was added, followed by TEA (227 mg, 2.25 mmol). The solution was stirred at room temperature for 8 days. Saturated NaHCO$_3$ was added into reaction solution and the organic layer was washed, collected, dried over Mg$_2$SO$_4$. The crude product was purified by reverse phase chromatography (Isolera One, HS—C18-30 g cartridge) with a gradient elution from 5 to 50% acetonitrile in water, and was lyophilized to give the desire product with 73% yield. UP LC-MS (waters) method: 5-95% acetonitrile (0.1% TFA) in water (0.1% TFA), 3 mins run, RT (min) 1.42, Found m/z: 489.2. HRMS (ESI$^+$) for $C_{28}H_{30}FN_4O_3$ (MH$^+$), calcd 489.2302, found 489.2312. $^1$H NMR (599 MHz, methanol-d$_4$) δ ppm 8.04 (d, J=3.2 Hz, 1H), 7.91 (d, J=2.7 Hz, 1H), 7.72 (d, J=8.8 Hz, 2H), 7.62 (dd, J=8.8, 2.7 Hz, 1H), 7.52-7.46 (m, 2H), 7.43-7.38 (m, 2H), 7.15 (dd, J=9.0, 3.2 Hz, 1H), 4.18-4.08 (m, 1H), 3.61-3.47 (m, 3H), 2.83-2.76 (m, 1H), 2.74-2.61 (m, 1H), 2.47-2.41 (m, 2H), 2.24 (d, J=5.5 Hz, 3H), 1.97-1.79 (m, 2H), 1.68-1.28 (m, 4H), 0.92-0.79 (m, 1H). 19F NMR (376 MHz, methanol-d$_4$) δ ppm −135.13−−135.29 (m, 1F).

(S)-6-(benzo[d]thiazol-6-yloxy)-3-((1-(2-hydroxyethyl)piperidin-3-yl)methyl)-2-(o-tolyl)quinazolin-4(3H)-one (5i,JQ-3-39)

The method similar for the preparation of compound 5h was used, except replacing compound 4b with 4e. Compound 5i was purified by reverse phase chromatography (Isolera One, HS—C18-30 g cartridge) with a gradient elution from 0 to 50% acetonitrile in water, and was lyophilized to give the desire product with 80% yield. UP LC-MS (waters) method: 5-95% acetonitrile (0.1% TFA) in water (0.1% TFA), 3 mins run, RT (min) 1.48, Found m/z: 527.2. HRMS (ESI$^+$) for $C_{30}H_{31}FN_4O_3S$ (MH$^+$), calcd 527.2117, found 527.2112. $^1$H NMR (400 MHz, methanol-d$_4$) δ ppm 9.19 (s, 1H), 8.09 (d, J=8.9 Hz, 1H), 7.79 (d, J=2.4 Hz, 1H), 7.70 (d, J=8.9 Hz, 1H), 7.67 (d, J=2.8 Hz, 1H), 7.59 (dd, J=8.9, 2.8 Hz, 1H), 7.50-7.44 (m, 2H), 7.40-7.35 (m, 2H), 7.33 (dd, J=8.9, 2.4 Hz, 1H), 4.18-3.99 (m, 1H), 3.62-3.39 (m, 3H), 2.94-2.66 (m, 2H), 2.58-2.45 (m, 2H), 2.20 (d, J=5.7 Hz, 3H), 2.13-1.91 (m, 2H), 1.80-1.18 (m, 4H), 0.93-0.75 (m, 1H).

3-(((3S)-1-(2-fluoropropanoyl)piperidin-3-yl)methyl)-6-((5-fluoropyridin-2-yl)oxy)-2-(o-tolyl)quinazolin-4(3H)-one (5j,JQ-2-113)

2-fluoropropionic acid (18.4 mg, 0.22 mmol), 1-Ethyl-3-(3-dimethylaminopropyl)carbodiimide (EDC) (38.4 mg, 0.22 mmol) and hydroxybenzotriazole (HOBt) (5 mg, 0.033 mmol) were added into DCM (5 ml). The solution was stirred for 5 minutes. Compound 4b (44 mg, 0.099 mmol) was then added. The resulting solution was stirred at room temperature for 24 hours. The solvent was removed and the product was subjected to reverse phase chromatography (Isolera One, HS—C18-30 g cartridge) with a gradient elution of 0-75% acetonitrile in water. The purified compound was lyophilized to give 35 mg white power with 69% yield. UP LC-MS (waters) method: 5-95% acetonitrile (0.1% TFA) in water (0.1% TFA), 3 mins run, RT (min) 2.09, Found m/z (MH$^+$): 519.1. HRMS (ESI$^+$) for $C_{29}H_{28}F_2N_4O_3Na$ (M+Na$^+$), calcd 541.2027, found 541.2031. $^1$H NMR (400 MHz, methanol-d$_4$) δ ppm 7.94 (d, J=2.9 Hz, 1H), 7.81 (d, J=2.7 Hz, 1H), 7.65-7.56 (m, 2H), 7.52 (dd, J=8.8, 2.7 Hz, 1H), 7.45-7.36 (m, 2H), 7.34-7.26 (m, 2H), 7.05 (dd, J=8.9, 2.9 Hz, 1H), 5.37-4.98 (m, 1H), 4.23-3.87 (m, 2H), 3.75-3.32 (m, 2H), 2.97-2.23 (m, 2H), 2.19-2.09 (m, 3H), 1.74-1.00 (m, 8H). 19F NMR (376 MHz, methanol-d$_4$) δ ppm −134.46−−135.77 (m, 1F), −177.27−−179.90 (m, 1F).

Synthesis of the 2$^{nd}$ Serial of the Compounds 6-bromo-2-(2-fluorophenyl)-4H-benzo[d][1,3]oxazin-4-one (6,JQ-2-91)

To a solution of 2-amino-5-bromobenzoic acid (5 g, 23 mmol) and triethylamine (10 ml; 70 mmol) in dichloromethane (50 ml) was added 2-fluorobenzoyl chloride (4.4 g, 28 mmol) drop wise at room temperature. After the suspension was stirred for 12 hours, the solvent was removed and acetic acid anhydride (45 ml) was added. The resulting suspension was stirred at 50° C. for 2 hours. After cooling down, the precipitate was collected by filtration and washed with ethanol (100 ml). The product was dried under vacuum for an hour to give 5.9 g light yellow powder with 80% yield. UP LC-MS (waters) method: 5-95% acetonitrile (0.1% TFA) in water (0.1% TFA), 3 mins run; Calculated m/z 319.9722 (MH$^+$), Found m/z: 319.9566; RT (min) 2.32.

(R)-tert-butyl 3-((5-bromo-2-(2-fluorobenzamido) benzamido)methyl)piperidine-1-carboxylate (7,JQ-2-97)

Compound 7 (2 g, 6.3 mmol) was dissolved in toluene (20 ml). (R)-1-Boc-3-(aminomethyl)pyrrolidine (1.62 g, 7.6 mmol) was added and the solution was refluxed at 125° C. for 16 h. The solvent was removed and the crude product was purified via silica gel column chromatography using 100% ethyl acetate to give the product as yellow oil with 89% yield. UP LC-MS (waters) method: 5-95% acetonitrile (0.1% TFA) in water (0.1% TFA), 3 mins run; Calculated m/z 534.1404 (MH$^+$), Found m/z: 534.1771; RT (min) 2.57.

(R)-tert-butyl 3-((6-bromo-2-(2-fluorophenyl)-4-oxoquinazolin-3(4H)-yl)methyl)piperidine-1-carboxylate (8,JQ-2-105)

Compound 7 (1.50 g, 2.80 mmol) was added to microwave reaction vessel, followed by ethylene glycol (6 mL) and LiOH (0.14 mg, 5.60 mmol). The resulting mixture was subjected to microwave irradiation with stirring for 30 minutes at 130° C., cooled to room temperature, and diluted with CH$_2$Cl$_2$ (50 ml) and water (50 ml). The organic layer was washed with brine (50 mL) twice. The combined organic layer was dried over Mg$_2$SO$_4$ and then concentrated under reduced pressure. The crude compound was purified via silica gel column chromatography using an elution of 25% ethyl acetate in hexanes to give 0.95 g of the product as yellow oil with 66% yield. UP LC-MS (waters) method: 5-95% acetonitrile (0.1% TFA) in water (0.1% TFA), 3 mins run; Calculated m/z 516.1298 (MH$^+$), Found m/z: 516.1048; RT (min) 2.81.

(S)-2-(2-fluorophenyl)-6-((5-fluoropyridin-2-yl)oxy)-3-(piperidin-3-ylmethyl)quinazolin-4(3H)-one (9a,JQ-3-81)

Under a nitrogen atmosphere, compound 8 (307 mg, 0.60 mmol), copper(I) chloride (30 mg, 0.30 mmol), 2,2,6,6-tetramethylheptane-3,5-dione (TMHD) (55 mg, 0.30 mmol), 5-fluoro-2-pyridinol (81 mg, 0.72 mmol) and Cs$_2$CO$_3$ (391 mg, 1.20 mmol) were added to 1-methyl-2-pyrrolidone (1 mL). The reaction mixture was stirred for 16 h at 110° C., cooled, and filtered through Celite. The filtrate was concentrated under reduced pressure and purified via silica gel column chromatography using a gradient elution from 20 to 25% ethyl acetate in hexanes to give 103 mg of Boc-protected intermediate with 31% yield. UP LC-MS (waters) method: 5-95% acetonitrile (0.1% TFA) in water (0.1% TFA), 3 mins run; Calculated m/z 549.2313 (MH$^+$), Found m/z: 549.2064; RT (min) 2.56. The Boc-protected intermediate (103 mg, 0.19 mmol) was dissolved in CH$_2$Cl$_2$ (10 mL). TFA (2 mL) was added. The solution was stirred for 3 hours at room temperature. The solvent was removed and saturated aqueous NaHCO$_3$ solution was added. The product was then extracted with EtOAc (2×). The combined organic layers were dried with Na$_2$SO$_4$ and filtered, and the solvent was removed under reduced pressure, and the crude compound was purified by reverse phase chromatography (Isolera One, HS—C18-30 g cartridge) with a gradient from 20 to 90% methanol in water. The product was lyophilized to yield 76 mg white powder with 90% yield. UP LC-MS (waters) method: 5-95% acetonitrile (0.1% TFA) in water (0.1% TFA), 3 mins run, RT (min) 1.39, Found m/z: 449.2. HRMS (ESI$^+$) for C$_{25}$H$_{23}$F$_2$N$_4$O$_2$ (MH$^+$), calcd 449.1789, found 449.1780. $^1$H NMR (400 MHz, methanol-d$_4$) δ ppm 8.05 (d, J=3.1 Hz, 1H), 7.90 (d, J=2.7 Hz, 1H), 7.77-7.62 (m, 5H), 7.46-7.40 (m, 1H), 7.36 (t, J=9.2 Hz, 1H), 7.16 (dd, J=9.0, 3.1 Hz, 1H), 4.27-4.01 (m, 1H), 3.79-3.52 (m, 1H), 2.89-2.66 (m, 2H), 2.46-2.31 (m, 1H), 2.27-2.02 (m, 1H), 1.84-1.69 (m, 1H), 1.61-1.50 (m, 1H), 1.46-1.21 (m, 2H), 1.07-0.85 (m, 1H). 19F NMR (376 MHz, methanol-d$_4$) δ ppm −114.29−−115.32 (m, 1F), −134.92−−135.09 (m, 1F)

(S)-2-(2-fluorophenyl)-6-((5-fluoropyridin-2-yl)oxy)-3-((1-isopropylpiperidin-3-yl)methyl)quinazolin-4(3H)-one (10a,JQ-4-99)

Compound 9a was treated with 2-bromopropane and potassium carbonate in acetonitrile at 70° C. for 16 h. The crude compound was purified by reverse phase chromatography (Isolera One, HS—C18-30 g cartridge) with a gradient from 05 to 70% methanol in water. The product was lyophilized to give the product as white powder with 47% yield. UP LC-MS (waters) method: 5-95% acetonitrile (0.1% TFA) in water (0.1% TFA), 3 mins run, RT (min) 1.59, Found m/z: 491.2. HRMS (ESI$^+$) for C$_{28}$H$_{29}$F$_2$N$_4$O$_2$ (MH$^+$), calcd 491.2259, found 491.2262. $^1$H NMR (400 MHz, methanol-d$_4$) δ ppm 8.05 (d, J=3.1 Hz, 1H), 7.93 (d, J=2.7 Hz, 1H), 7.78-7.63 (m, 5H), 7.49-7.34 (m, 2H), 7.17 (dd, J=9.0, 3.5 Hz, 1H), 4.33-4.02 (m, 1H), 3.97-3.65 (m, 1H), 3.52-3.38 (m, 1H), 3.27-3.18 (m, 1H), 2.86-2.60 (m, 2H), 2.28-2.12 (m, 1H), 1.91 (t, J=13.4 Hz, 1H), 1.69-1.41 (m, 2H), 1.39-1.01 (m, 8H). $^{19}$F NMR (376 MHz, methanol-d$_4$) δ ppm −114.55−−115.80 (m, 1F), −136.10−−136.17 (m, 1F).

(S)-6-(benzo[d]thiazol-6-yloxy)-2-(2-fluorophenyl)-3-(piperidin-3-ylmethyl)quinazolin-4(3H)-one (9b, JQ-2-115)

The method similar for the preparation of compound 9a was used, except replacing 5-fluoro-2-pyridinol with 6-benzothiazolol. The Boc-protected intermediate was purified via silica gel column chromatography using a gradient elution from 25 to 50% ethyl acetate in hexane and gave 18% yield. UP LC-MS (waters) method: 5-95% acetonitrile (0.1% TFA) in water (0.1% TFA), 3 mins run; Calculated m/z 587.2128 (MH$^+$), Found m/z: 587.0820; RT (min) 2.62. After Boc deprotection, the crude compound was purified by reverse phase chromatography (Isolera One, HS—C18-30 g cartridge) with a gradient from 0 to 100% methanol in water. The product was lyophilized to give the product as white powder with 57% yield. UP LC-MS (waters) method: 5-95% acetonitrile (0.1% TFA) in water (0.1% TFA), 3 mins run, RT (min) 1.43, Found m/z: 487.2. HRMS (ESI$^+$) for C$_{27}$H$_{24}$FN$_4$O$_2$S (MH$^+$), calcd 487.1604, found 487.1605. $^1$H NMR (400 MHz, methanol-d$_4$) δ ppm 9.22 (s, 1H), 8.12 (d, J=8.8 Hz, 1H), 7.83 (d, J=2.4 Hz, 1H), 7.75 (d, J=8.8 Hz, 1H), 7.71-7.59 (m, 4H), 7.46-7.39 (m, 1H), 7.39-7.31 (m, 2H), 4.23-3.98 (m, 1H), 3.78-3.52 (m, 1H), 2.87-2.65 (m, 2H), 2.43-2.31 (m, 1H), 2.22-2.00 (m, 1H), 1.81-1.68 (m, 1H), 1.58-1.49 (m, 1H), 1.44-1.20 (m, 2H), 1.04-0.86 (m, 1H). $^{19}$F NMR (376 MHz, methanol-d$_4$) δ ppm −114.05−−114.49 (m, 1F).

(S)-6-(benzo[d]thiazol-6-yloxy)-2-(2-fluorophenyl)-3-((1-isopropylpiperidin-3-yl)methyl)quinazolin-4(3H)-one (10b,JQ-2-127)

The method similar for the preparation of compound 10a was used, except replacing 9a with 9b. The crude compound was purified by reverse phase chromatography (Isolera One, HS—C18-30 g cartridge) with a gradient from 25 to 80% methanol in water. The product was lyophilized to give the product as white powder with 52% yield. UP LC-MS (waters) method: 5-95% acetonitrile (0.1% TFA) in water (0.1% TFA), 3 mins run, RT (min) 1.54, Found m/z: 529.2. HRMS (ESI$^+$) for $C_{30}H_{30}FN_4O_2S$ (MH$^+$), calcd 529.2074, found 529.2071. $^1$H NMR (400 MHz, methanol-$d_4$) δ ppm 9.21 (s, 1H), 8.11 (d, J=8.9 Hz, 1H), 7.82 (d, J=2.3 Hz, 1H), 7.74 (d, J=8.9 Hz, 1H), 7.69 (d, J=2.8 Hz, 1H), 7.68-7.63 (m, 2H), 7.61 (dd, J=8.9, 2.8 Hz, 1H), 7.42 (t, J=7.5 Hz, 1H), 7.38-7.32 (m, 2H), 4.17-4.03 (m, 1H), 3.75-3.61 (m, 1H), 2.86-2.59 (m, 3H), 2.22-2.05 (m, 1H), 1.99-1.75 (m, 2H), 1.68-1.56 (m, 1H), 1.55-1.32 (m, 2H), 1.04-0.95 (m, 6H), 0.91-0.73 (m, 1H). $^{19}$F NMR (376 MHz, methanol-$d_4$) δ ppm −113.78−−114.26 (m, 1F).

(S)-6-(benzo[d]thiazol-6-yloxy)-3-((1-(2-fluoroethyl)piperidin-3-yl)methyl)-2-(2-fluorophenyl)quinazolin-4(3H)-one (10c,JQ-4-13)

The method similar for the preparation of compound 10b was used, except replacing 2-bromopropane with 9b. The crude compound was purified by reverse phase chromatography (Isolera One, HS—C18-30 g cartridge) with a gradient (0.1% TFA) from 5 to 80% methanol in water. The product was lyophilized to give the product as TFA salt with 48% yield. UP LC-MS (waters) method: 5-95% acetonitrile (0.1% TFA) in water (0.1% TFA), 3 mins run, RT (min) 1.55, m/z: 533.2. HRMS (ESI$^+$) for $C_{29}H_{27}F_2N_4O_2S$ (MH$^+$), calcd 533.1823, found 533.1824. $^1$H NMR (400 MHz, methanol-$d_4$) δ ppm 9.23 (s, 1H), 8.13 (d, J=8.9 Hz, 1H), 7.83 (d, J=2.4 Hz, 1H), 7.76 (d, J=8.9 Hz, 1H), 7.71-7.61 (m, 4H), 7.43 (t, J=7.3 Hz, 1H), 7.40-7.33 (m, 2H), 4.74-4.64 (m, 1H), 4.61-4.52 (m, 1H), 4.31-4.02 (m, 1H), 3.87-3.58 (m, 1H), 3.21-2.93 (m, 4H), 2.60-1.98 (m, 3H), 1.82-1.31 (m, 3H), 1.14-0.84 (m, 1H). $^{19}$F NMR (376 MHz, methanol-$d_4$) δ ppm −114.77−−116.91 (m, 1F), −219.89−−222.07 (m, 1F).

Synthesis of the 3$^{rd}$ Serial of the Compounds

6-bromo-2-(2,4-difluorophenyl)-4H-benzo[d][1,3]oxazin-4-one (11,JQ-3-103)

The compound was made according to literature procedure. To a solution of 2-amino-5-bromobenzoic acid (5 g, 23 mmol) and triethylamine (10 ml; 70 mmol) in dichloromethane (50 ml) was added 2,4-difluorobenzoyl chloride (4.9 g, 28 mmol) drop wise at room temperature. After the suspension was stirred for 12 hours, the solvent was removed and acetic acid anhydride (45 ml) was added. The resulting suspension was stirred at 50° C. for 2 hours. After cooling down, the precipitate was collected by filtration and washed with methanol (100 ml). The product was dried under vacuum for an hour to give 6.6 g light yellow powder with 85% yield. UP LC-MS (waters) method: 5-95% acetonitrile (0.1% TFA) in water (0.1% TFA), 3 mins run; Calculated m/z 337.9628 (MH$^+$), Found m/z: 337.9193; RT (min): 2.38.

(R)-tert-butyl 3-((5-bromo-2-(2,4-difluorobenzamido)benzamido)methyl)piperidine-1-carboxylate (12,JQ-3-109)

The compound was made according to literature procedure with some modifications. Compound 11 (3.7 g, 10.98 mmol) was dissolved in toluene (125 ml). (R)-1-Boc-3-(aminomethyl)pyrrolidine (2.40 g, 11.21 mmol) was added and it was refluxed at 110° C. for 8 h. The reaction mixture was cooled down and solvent was removed. The precipitate was washed with hexane (50 ml) to give pure product as light yellow power with 98% yield. UP LC-MS (waters) method: 5-95% acetonitrile (0.1% TFA) in water (0.1% TFA), 3 mins run; Calculated m/z 552.1310 (MH$^+$), Found m/z: 552.1366; RT (min): 2.68.

(R)-tert-butyl 3-((5-bromo-2-(2,4-difluorobenzamido)benzamido)methyl)piperidine-1-carboxylate (13,JQ-3-113)

Compound 12 (1.50 g, 2.72 mmol) was added to microwave reaction vessel, followed by ethylene glycol (12 mL) and LiOH (0.13 mg, 5.44 mmol). The resulting mixture was subjected to microwave irradiation with stirring for 30 minutes at 150° C., cooled to room temperature, and diluted with $CH_2Cl_2$ (50 ml) and water (50 ml). The organic layer was washed with brine (50 mL) twice. The combined organic layer was dried over $Mg_2SO_4$ and then concentrated under reduced pressure. The crude compound was purified via silica gel column chromatography using an elution of 50% ethyl acetate in hexanes to give 0.61 g of the product as white foam with 38% yield. UP LC-MS (waters) method: 5-95% acetonitrile (0.1% TFA) in water (0.1% TFA), 3 mins run; Calculated m/z 576.1509 (MH$^+$), Found m/z: 576.1633; RT (min): 2.34.

(S)-2-(2-fluoro-4-(2-hydroxyethoxy)phenyl)-6-((5-fluoropyridin-2-yl)oxy)-3-(piperidin-3-ylmethyl)quinazolin-4(3H)-one (14a,JQ-3-135)

Under a nitrogen atmosphere, compound 13 (623 mg, 1.08 mmol), copper(I) chloride (107 mg, 1.08 mmol), 2,2,6,6-tetramethylheptane-3,5-dione (TMHD) (100 mg, 0.54 mmol), 5-fluoro-2-pyridinol (184 mg, 1.63 mmol) and $Cs_2CO_3$ (704 mg, 2.16 mmol) were added to 1-methyl-2-pyrrolidinone (3 mL). The reaction mixture was stirred for 16 h at 115° C., cooled, and passed through a Celite bed. The filtrate was diluted with DCM (50 ml) and washed with brine (50 ml×2). The organic layer was dried over $Mg_2SO_4$, filtered and concentrated under reduced pressure. The crude product was purified by reverse phase chromatography (Isolera One, HS—C18-30 g cartridge) with a gradient from 0 to 70% acetonitrile in water. The product was lyophilized to give 213 mg of the Boc-protected intermediate as white powder with 32% yield. UP LC-MS (waters) method: 5-95% acetonitrile (0.1% TFA) in water (0.1% TFA), 3 mins run; Calculated m/z: 609.2525 (MH$^+$), Found m/z: 609.2766; RT (min): 2.18. The Boc-protected intermediate (70 mg, 0.12 mmol) was dissolved in $CH_2Cl_2$ (5 mL). TFA (1 mL) was added. The solution was stirred for 3 hours at room temperature. The solvent was removed and saturated aqueous $NaHCO_3$ solution was added. The product was then extracted with EtOAc (2×). The combined organic layers were dried with $Na_2SO_4$ and filtered, and the solvent was removed under reduced pressure, and the crude compound was purified by reverse phase chromatography (Isolera One, HS—C18-30 g cartridge) with a gradient from 05 to 60% methanol in water. The product was lyophilized to yield 40 mg white powder with 66% yield. UP LC-MS (waters) method: 5-95% acetonitrile (0.1% TFA) in water (0.1% TFA), 3 mins run, RT (min) 1.29, m/z 509.2; HRMS (ES+) for $C_{27}H_{27}F_2N_4O_4$ (MH$^+$), calcd 509.2000, found 509.2003. $^1$H NMR (400 MHz, methanol-d$_4$) δ ppm 8.05 (d, J=3.1 Hz, 1H), 7.91 (d, J=2.7 Hz, 1H), 7.78-7.71 (m, 2H), 7.65 (dd, J=8.9, 2.8 Hz, 1H), 7.57 (t, J=8.4 Hz, 1H), 7.17 (dd, J=9.0, 3.5 Hz, 1H), 7.05-6.97 (m, 2H), 4.38-4.03 (m, 3H), 4.02-3.66 (m, 3H), 3.26-3.14 (m, 2H), 2.92-2.75 (m, 1H), 2.75-2.52 (m, 1H), 2.14-2.01 (m, 1H), 1.92-1.77 (m, 1H), 1.67-1.48 (m, 2H), 1.27-1.10 (m, 1H). $^{19}$F NMR (3 76 MHz, methanol-d$_4$) δ ppm −112.58−−113.26 (m), −136.07−−136.26 (m).

(S)-2-(2-fluoro-4-(2-hydroxyethoxy)phenyl)-6-(4-fluorophenoxy)-3-(piperidin-3-ylmethyl)quinazolin-4(3H)-one (14b,JQ-4-59)

The method similar for the preparation of compound 14a was used, except replacing 5-fluoro-2-pyridinol with 4-fluorophenol. The crude Boc-protected intermediate was purified via silica gel column chromatography using a elution of 30% ethyl acetate in hexanes to give 308 mg of the product with 61% yield. UP LC-MS (waters) method: 5-95% acetonitrile (0.1% TFA) in water (0.1% TFA), 3 mins run; Calculated m/z: 608.2572 (MH$^+$), Found m/z: 609.2756; RT (min): 2.50. After Boc-deprotection, the final product was purified by reverse phase chromatography (Isolera One, HS—C18-30 g cartridge) with a gradient from 05 to 60% methanol in water. The product was lyophilized to yield 200 mg white powder with 77% yield. UP LC-MS (waters) method: 5-95% acetonitrile (0.1% TFA) in water (0.1% TFA), 3 mins run, RT (min): 1.61, Found m/z: 508.2. HRMS (ESI$^+$) for $C_{28}H_{28}F_2N_3O_4$ (MH$^+$), calcd 508.2048, found 508.2046. $^1$H NMR (400 MHz, methanol-d$_4$) δ ppm 7.72 (d, J=8.8 Hz, 1H), 7.62-7.51 (m, 3H), 7.24-7.11 (m, 4H), 7.05-6.95 (m, 2H), 4.37-3.99 (m, 3H), 3.95-3.60 (m, 3H), 3.27-3.10 (m, 2H), 2.82 (t, J=12.2 Hz, 1H), 2.74-2.53 (m, 1H), 2.10-1.98 (m, 1H), 1.89-1.76 (m, 1H), 1.69-1.43 (m, 2H), 1.28-1.05 (m, 1H). $^{19}$F NMR (376 MHz, methanol-d$_4$) δ ppm −112.36−−113.15 (m, 1F), −119.48−−119.85 (m, 1F).

(S)-2-(2-fluoro-4-(2-hydroxyethoxy)phenyl)-6-((5-fluoropyridin-2-yl)oxy)-3-((1-isopropylpiperidin-3-yl)methyl)quinazolin-4(3H)-one (15a,JQ-3-143)

Compound 14a (127 mg, 0.25 mmol), 2-bromopropane (308 mg, 2.5 mmol), and K$_2$CO$_3$ (345 mg, 2.5 mmol) were combined in acetonitrile (5 ml) and three drops of water was added and the resulting mixture was heated to 80° C. for 8 h. The solid was filtered off, and the filtrate was concentrated under reduced pressure. Saturated aqueous NaHCO$_3$ solution was added, and the product was extracted with EtOAc (2×). The combined organic layers were dried with Na$_2$SO$_4$ and filtered. The solvent was removed under reduced pressure, and the crude product was purified by reverse phase chromatography (Isolera One, HS—C18-30 g cartridge) with a gradient from 05 to 90% methanol in water. The product was lyophilized to yield 100 mg white powder with 73% yield. UP LC-MS (waters) method: 5-95% acetonitrile (0.1% TFA) in water (0.1% TFA), 3 mins run, RT (min): 1.38, Found m/z: 551.3. HRMS (ESI$^+$) for $C_{30}H_{33}F_2N_4O_4$ (MH$^+$), calcd 551.2470, found 551.2464. $^1$H NMR (400 MHz, methanol-d$_4$) δ ppm 8.05 (d, J=3.1 Hz, 1H), 7.92 (d, J=2.7 Hz, 1H), 7.79-7.71 (m, 2H), 7.65 (dd, J=8.8, 2.7 Hz, 1H), 7.58 (t, J=8.4 Hz, 1H), 7.17 (dd, J=9.0, 3.6 Hz, 1H), 7.05-6.97 (m, 2H), 4.31-4.09 (m, 3H), 3.96-3.71 (m, 3H), 3.50-3.39 (m, 1H), 3.28-3.16 (m, 1H), 2.91-2.60 (m, 2H), 2.31-2.13 (m, 1H), 2.01-1.86 (m, 1H), 1.71-1.49 (m, 2H), 1.37-1.00 (m, 8H). $^{19}$F NMR (376 MHz, methanol-d$_4$) δ ppm −112.28−−113.79 (m, 1F), −136.06−−136.64 (m, 1F).

(S)-2-(2-fluoro-4-(2-hydroxyethoxy)phenyl)-6-(4-fluorophenoxy)-3-((1-isopropylpiperidin-3-yl)methyl)quinazolin-4(3H)-one (15b,JQ-4-63)

The method similar for the preparation of compound 15a was used, except compound 14a with 14b. The crude product was purified by reverse phase chromatography (Isolera One, HS—C18-30 g cartridge) with a gradient elution from 05 to 90% methanol (0.1% TFA) in water (0.1% TFA). The product was lyophilized to yield white powder with 70% yield. UP LC-MS (waters) method: 05-95% acetonitrile (0.1% TFA) in water (0.1% TFA), 3 mins run, RT (min) 1.65, m/z: 550.3; HRMS (ESI$^+$) for $C_{31}H_{34}F_2N_3O_4$ (MH$^+$), calcd 550.2517; found 550.2502. $^1$H NMR (400 MHz, methanol-d$_4$) δ ppm 7.73 (d, J=8.8 Hz, 1H), 7.62-7.52 (m, 3H), 7.24-7.12 (m, 4H), 7.07-6.96 (m, 2H), 4.30-4.01 (m, 3H), 3.95-3.68 (m, 3H), 3.49-3.39 (m, 1H), 3.28-3.14 (m, 1H), 2.88-2.57 (m, 2H), 2.25-2.12 (m, 1H), 1.96-1.83 (m, 1H), 1.68-1.37 (m, 2H), 1.34-0.91 (m, 8H). $^{19}$F NMR (376 MHz, methanol) δ ppm −112.52−−113.48 (m, 1F), −119.91−−120.02 (M, 1F).

(S)-2-(3-fluoro-4-(6-((5-fluoropyridin-2-yl)oxy)-3-((1-isopropylpiperidin-3-yl)methyl)-4-oxo-3,4-dihydroquinazolin-2-yl)phenoxy)ethyl 4-methylbenzenesulfonate (16a,JQ-4-37)

To a solution of p-Toluenesulfonic anhydride (95 mg, 0.29 mmol) in dry dichloromethane (3 ml) was added Ytterbium(III) trifluoromethanesulfonate (Yb(OTf)$_3$) (93 mg, 0.15 mmol) and the suspension was stirred for five minutes until most of the solid was dissolved. Compound 15a (80 mg, 0.15 mmol) was added and the resulting mixture was subjected to microwave irradiation with stirring for one hour at 90° C., cooled to room temperature and passed through a celite bed. The crude product was purified by reverse phase chromatography (Isolera One, HS—C18-30 g cartridge) with a gradient elution from 20 to 80% methanol (0.1% TFA) in water (0.1% TFA). The product was lyophilized to yield 100 mg of white powder with 95% yield. UP LC-MS (waters) method: 05-95% acetonitrile (0.1% TFA) in water (0.1% TFA), 3 mins run; Calculated m/z: 705.2558 (MH$^+$), Found m/z: 705.2344; RT (min): 1.96. $^1$H NMR (400 MHz, methanol-d$_4$) δ ppm 8.04 (d, J=3.0 Hz, 1H), 7.91 (d, J=2.7 Hz, 1H), 7.81 (d, J=8.3 Hz, 2H), 7.78-7.69 (m, 2H), 7.64 (dd, J=8.9, 2.7 Hz, 1H), 7.57 (t, J=8.3 Hz, 1H), 7.47 (d, J=8.3 Hz, 2H), 7.16 (dd, J=8.9, 3.5 Hz, 1H), 6.97-6.86 (m, 2H), 4.44-4.35 (m, 2H), 4.33-4.27 (m, 2H), 4.28-4.05 (m, 1H), 3.94-3.66 (m, 1H), 3.49-3.37 (m, 1H), 3.27-3.13 (m, 1H), 2.87-2.59 (m, 2H), 2.47 (s, 3H), 2.29-2.12 (m, 1H), 1.99-1.81 (m, 1H), 1.70-1.47 (m, 2H), 1.37-1.00 (m, 8H). $^{19}$F NMR (376 MHz, methanol-d$_4$) δ ppm −111.80−−113.41 (m, 1F), −133.11−−136.25 (m, 1F).

(S)-2-(3-fluoro-4-(6-(4-fluorophenoxy)-3-((1-isopropylpiperidin-3-yl)methyl)-4-oxo-3,4-dihydroquinazolin-2-yl)phenoxy)ethyl 4-methylbenzenesulfonate (16b,JQ-4-69)

The method similar for the preparation of compound 16a was used, except replacing compound 15a with 15b. The crude product was purified by reverse phase chromatography (Isolera One, HS—C18-30 g cartridge) with a gradient elution from 20 to 80% methanol (0.1% TFA) in water (0.1% TFA). The product was lyophilized to yield white powder with 75% yield. UP LC-MS (waters) method: 05-95% acetonitrile (0.1% TFA) in water (0.1% TFA), 3 mins run; Calculated m/z: 704.2606 (MH$^+$), Found m/z: 704.2416; RT (min): 2.11. $^1$H NMR (400 MHz, methanol-d$_4$) δ ppm 7.81 (d, J=8.3 Hz, 2H), 7.73 (d, J=8.8 Hz, 1H), 7.62-7.52 (m, 3H), 7.47 (d, J=8.0 Hz, 2H), 7.20 (s, 4H), 6.96-6.87 (m, 2H), 4.42-4.37 (m, 2H), 4.33-4.27 (m, 2H), 4.27-4.05 (m, 1H), 3.94-3.64 (m, 1H), 3.49-3.36 (m, 1H), 3.27-3.11 (m, 1H), 2.86-2.76 (m, 1H), 2.74-2.56 (m, 1H), 2.47 (s, 3H), 2.26-2.11 (m, 1H), 1.97-1.85 (m, 1H), 1.66-1.44 (m, 2H), 1.43-0.89 (m, 7H). $^{19}$F NMR (376 MHz, methanol-d$_4$) δ ppm −112.65--113.59 (m, 1F), −120.27--120.38 (m, 1F).

(S)-2-(2-fluoro-4-(2-fluoroethoxy)phenyl)-6-((5-fluoropyridin-2-yl)oxy)-3-((1-isopropylpiperidin-3-yl)methyl)quinazolin-4(3H)-one (17a,JQ-4-51)

Tetrabutylammonium fluoride (45 mg, 0.17 mmol) was added into compound 16a (60 mg, 0.09 mmol) in acetonitrile (3 ml). The solution was stirred at 90° C. for 3 hours. The solvent was removed under reduced pressure. Dichloromethane was added and washed with saturated NaHCO$_3$. The organic layer was dried over Mg$_2$SO$_4$ and filtered. The crude product was purified by reverse phase chromatography (Isolera One, HS—C18-30 g cartridge) with a gradient elution from 20 to 60% methanol (0.1% TFA) in water (0.1% TFA). The product was lyophilized to yield 12 mg of white powder with 26% yield. UP LC-MS (waters) method: 05-95% acetonitrile (0.1% TFA) in water (0.1% TFA), 3 mins run, RT (min): 1.64, Found m/z: 553.2. HRMS (ESI$^+$) for C$_{30}$H$_{32}$F$_3$N$_4$O$_3$ (MH$^+$), calcd 553.2427, found 553.2438. $^1$H NMR (400 MHz, methanol-d$_4$) δ ppm 8.05 (d, J=3.1 Hz, 1H), 7.92 (d, J=2.7 Hz, 1H), 7.78-7.71 (m, 2H), 7.65 (dd, J=8.8, 2.7 Hz, 1H), 7.60 (t, J=8.8 Hz, 1H), 7.17 (d, J=9.0 Hz, 1H), 7.07-7.00 (m, 2H), 4.85-4.81 (m, 1H), 4.73-4.70 (m, 1H), 4.40-4.36 (m, 1H), 4.32-4.29 (m, 1H), 4.28-4.07 (m, 1H), 3.99-3.72 (m, 1H), 3.49-3.40 (m, 1H), 3.27-3.12 (m, 1H), 2.91-2.61 (m, 2H), 2.29-2.15 (m, 1H), 1.97-1.88 (m, 1H), 1.70-1.51 (m, 2H), 1.38-1.03 (m, 8H). $^{19}$F NMR (376 MHz, methanol-d$_4$) δ −112.33--113.44 (m, 1F), −136.23--136.47 (m, 1F), −224.60--225.32 (m, 1F).

(S)-2-(2-fluoro-4-(2-fluoroethoxy)phenyl)-6-(4-fluorophenoxy)-3-((1-isopropylpiperidin-3-yl)methyl)quinazolin-4(3H)-one (17b,JQ-4-81)

The method similar for the preparation of compound 17a was used. The crude product was purified by reverse phase chromatography (Isolera One, HS—C18-30 g cartridge) with a gradient elution from 5 to 80% methanol (0.1% TFA) in water (0.1% TFA). The product was lyophilized to yield white powder with 33% yield. UP LC-MS (waters) method: 05-95% acetonitrile (0.1% TFA) in water (0.1% TFA), 3 mins run, RT (min): 1.86, Found m/z: 552.3. HRMS (ESI$^+$) for C$_{31}$H$_{33}$F$_3$N$_3$O$_3$ (MH$^+$), calcd 552.2474, found 552.2471. $^1$H NMR (400 MHz, methanol-d$_4$) δ ppm 7.73 (d, J=8.7 Hz, 1H), 7.64-7.55 (m, 3H), 7.24-7.12 (m, 4H), 7.02 (t, J=8.7 Hz, 2H), 4.84-4.78 (m, 1H), 4.73-4.65 (m, 1H), 4.40-4.33 (m, 1H), 4.33-4.28 (m, 1H), 4.28-4.04 (m, 1H), 3.95-3.67 (m, 1H), 3.49-3.36 (m, 1H), 3.26-3.11 (m, 1H), 2.89-2.58 (m, 2H), 2.23 (s, 1H), 1.98-1.84 (m, 1H), 1.68-1.46 (m, 2H), 1.36-0.99 (m, 8H). $^{19}$F NMR (376 MHz, methanol-d$_4$) δ ppm −112.24--113.04 (m, 1F), −119.47--120.05 (m, 1F), −224.61--225.31 (m, 1F)

Synthesis of the 4$^{th}$ Serial of the Compounds (R)-tert-butyl 3-((4-oxo-2-(o-tolyl)-6-(tributylstannyl)quinazolin-3(4H)-yl)methyl)piperidine-1-carboxylate (17,JQ-4-33)

Tetrakis(triphenylphosphine)palladium(0) (127 mg, 0.13 mmol) and Bis(tributyltin) (1.50 g, 2.56 mmol) was added to compound 3 (655 mg, 1.28 mmol) in in toluene (50 ml). The resulting mixture was heated to 110° C. for 18 h. The reaction mixture was cooled down and passed through Celite. The solvent was removed under reduced pressure. The crude compound was purified via silica gel column chromatography using an elution of 10% ethyl acetate in hexanes to give 0.42 g of the product as oil with 56% yield. UP LC-MS (waters) method: 5-95% acetonitrile (0.1% TFA) in water (0.1% TFA), 3 mins run, RT (min): 1.74.

(R)-tert-butyl 3-((6-(4-fluorobenzoyl)-4-oxo-2-(o-tolyl)quinazolin-3(4H)-yl)methyl)piperidine-1-carboxylate (18,JQ-3-147)

4-fluorobenzoyl chloride (115 mg, 0.72 mmol) and Bis (triphenylphosphine)palladium(II) dichloride (35.1 mg, 0.05 mmol) were added to compound 17 (347 mg, 0.48 mmol) in toluene (5 ml). The resulting mixture was heated to 110° C. for 6 h. The reaction mixture was cooled down and passed through Celite. The solvent was removed under reduced pressure. The crude product was purified by reverse phase chromatography (Isolera One, HS—C18-30 g cartridge) with a gradient from 20 to 90% acetonitrile in water. The product was lyophilized to give 110 mg of the product as white powder with 42% yield. UP LC-MS (waters) method: 5-95% acetonitrile (0.1% TFA) in water (0.1% TFA), 3 mins run; Calculated m/z: 556.2606 (MH$^+$), Found m/z: 556.2849; RT (min): 2.73.

(S)-6-(4-fluorobenzoyl)-3-(piperidin-3-ylmethyl)-2-(o-tolyl)quinazolin-4(3H)-one (19,JQ-4-71)

Compound 18 (50 mg, 0.09 mmol) was dissolved in CH$_2$Cl$_2$ (5 mL). TFA (1 mL) was added. The solution was stirred for 3 hours at room temperature. The solvent was removed and saturated aqueous NaHCO$_3$ solution was added. The product was then extracted with EtOAc (2×). The combined organic layers were dried with Na$_2$SO$_4$ and filtered, and the solvent was removed under reduced pressure, and the crude compound was purified by reverse phase chromatography (Isolera One, HS—C18-30 g cartridge) with a gradient from 10 to 95% acetonitrile (0.1% TFA) in water (0.1% TFA). The product was lyophilized to yield 34 mg white powder with 83% yield. UP LC-MS (waters) method: 5-95% acetonitrile (0.1% TFA) in water (0.1% TFA), 3 mins run, RT (min): 1.55, Found m/z: 456.2. HRMS (ESI$^+$) for C$_{28}$H$_{27}$FN$_3$O$_2$ (MH$^+$), calcd 456.2087, found 456.2075. $^1$H NMR (400 MHz, methanol-d$_4$) δ ppm 8.61 (d, J=1.8 Hz, 1H), 8.28-8.21 (m, 1H), 7.95-7.88 (m, 2H), 7.81 (dd, J=8.5, 1.3 Hz, 1H), 7.56-7.50 (m, 2H), 7.49-7.40 (m, 2H), 7.35-7.28 (m, 2H), 4.37-4.07 (m, 1H), 3.84-3.40 (m, 1H), 3.27-3.14 (m, 2H), 2.91-2.55 (m, 2H), 2.28 (d, J=13.3 Hz, 3H), 2.16-2.00 (m, 1H), 1.92-1.78 (m, 1H), 1.68-1.36

(m, 2H), 1.27-1.09 (m, 1H). $^{19}$F NMR (376 MHz, methanol-$d_4$) δ ppm −106.97−−107.12 (m, 1F).

(S)-6-(4-fluorobenzoyl)-3-((1-isopropylpiperidin-3-yl)methyl)-2-(o-tolyl)quinazolin-4(3H)-one (20,JQ-4-5)

Compound 19 (10 mg, 0.02 mmol), 2-bromopropane (20 mg, 0.22 mmol), and $K_2CO_3$ (21 mg, 0.22 mmol) were combined in acetonitrile (2 ml) and heated to 70° C. for 8 h. The solid was filtered off, and the filtrate was concentrated under reduced pressure. Purification was performed by preparative reverse-phase C18 HPLC (gradient 35-95% acetonitrile in water, 0.1% TFA). The product was lyophilized to yield 9 mg white powder with 75% yield. UPLC-MS (waters) method: 5-95% acetonitrile (0.1% TFA) in water (0.1% TFA), 3 mins run, RT (min): 1.66, Found m/z: 498.3. HRMS (ESI$^+$) for $C_{31}H_{33}FN_3O_2$ (MH$^+$), calcd 498.2557, found 498.2559. $^1$H NMR (400 MHz, methanol-$d_4$) δ ppm 8.66-8.59 (m, 1H), 8.25 (dd, J=8.5, 2.0 Hz, 1H), 7.96-7.88 (m, 2H), 7.86-7.78 (m, 1H), 7.59-7.49 (m, 2H), 7.49-7.38 (m, 2H), 7.36-7.27 (m, 2H), 4.35-4.13 (m, 1H), 3.73-3.34 (m, 2H), 3.26-3.08 (m, 1H), 2.88-2.53 (m, 2H), 2.28 (d, J=17.2 Hz, 3H), 2.23-2.12 (m, 1H), 1.97-1.84 (m, 1H), 1.68-1.55 (m, 1H), 1.44-1.33 (m, 1H), 1.33-1.03 (m, 8H). $^{19}$F NMR (376 MHz, methanol-$d_4$) δ ppm −106.96−−107.30 (m, 1F).

Radiochemistry

Production of [$^{18}$F]Fluoride

The [$^{18}$F$^-$]anion was produced by the PET cyclotron (St. Joseph's Health Care London Ontario, Canada) as a result of the $^{18}$O(p,n)$^{18}$F reaction involving proton bombardment of [$^{18}$O]H$_2$O. A Waters Sep-Pak® Accell™ PlusLight (46 mg) QMA Carbonate cartridge was pre-activated by slowly treating with EtOH (10 ml) and Milli-Q® water (10 ml) and then flushing with air. The radioactive [$^{18}$F$^-$]anion was then trapped by drawing up the [$^{18}$O]H$_2$O solution containing it through the Sep-Pak.

Synthesis of [$^{18}$F]Fluoroethyl Tosylate

To potassium carbonate (3.0 mg) and Kryptofix 222 (10.0 mg) was added water (200 μl) and MeCN (800 μl) and the resulting solution used to elute the Sep-Pak® containing [$^{18}$F]fluoride into a glass vial. The mixture was dried azeotropically (120° C.). The drying step was repeated twice more after the drop-wise addition of anhydrous MeCN (1 ml). Ethylene glycol ditosylate (6.5 mg in 0.5 mL of MeCN) was added to the aforementioned mixture, and the mixture was heated at 125° C. for 10 min under sealed conditions. The reaction mixture was cooled, diluted with 6 ml hexane/diethyl ether (3:1) and loaded onto a Sep-Pak Silica Plus column (Waters). The last 3 ml of eluate was collected, and the cartridge was then eluted with 10 mL of hexane/diethyl ether (3:1). Eluate was collected and evaporated on a spin-vap (HI volatile, pressure: 100 psi, temp.: 36° C.).

Synthesis of [$^{18}$F]5b

The [$^{18}$F]fluoroethyl tosylate in 0.5 ml MeCN was transferred to the second reactor, which had been preloaded with 4b (1 mg) and $Cs_2CO_3$ (15 mg). The reaction mixture was heated at 150° C. for 20 min. After cooling, saturated $K_2CO_3$ solution (10 ml) was added and it was passed through sep-pak C18 plus cartridge, followed by 5 ml water. The product was eluted out with 1.5 ml MeCN. Azeotropically removed 0.5 ml MeCN and 0.5 ml water (0.5 ml, 0.1% TFA) was added. The radiolabelled compound was purified by semi-prep HPLC using 35-50% MeCN in Water (0.1% TFA, flow rate: 4.5 ml/min, 15 min run, 2 min wash).

Synthesis of [$^{18}$F]5e

The [$^{18}$F]fluoroethyl tosylate in 0.5 ml MeCN was transferred to the second reactor, which had been preloaded with 4e (1 mg) and $Cs_2CO_3$ (15 mg). The reaction mixture was heated at 140° C. for 20 min. After cooling, saturated $K_2CO_3$ solution (10 ml) was added and it was passed through sep-pak C18 plus cartridge, followed by 5 ml water. The product was eluted out with 1.5 ml MeCN. Azeotropically removed 0.5 ml MeCN and 0.5 ml water (0.5 ml, 0.1% TFA) was added. The radiolabelled compound was purified by semi-prep HPLC using 40% MeCN in Water (0.1% TFA, flow rate: 4.5 ml/min, 17 min run, 2 min wash).

Synthesis of [$^{18}$F]17b

To potassium carbonate (3.0 mg) and Kryptofix 222 (10.0 mg) was added water (200 μl) and MeCN (800 μl) and the resulting solution used to elute the Sep-Pak® containing [$^{18}$F]fluoride into a glass vial. The mixture was dried azeotropically (120° C.). The drying step was repeated twice more after the drop-wise addition of anhydrous MeCN (1 ml). 16b (2.0 mg in 0.5 mL of MeCN) was added to the aforementioned mixture, and the mixture was heated at 100° C. for 10 min under sealed conditions. 0.5 ml of water containing 0.1% TFA as added. The radiolabelled compound was purified by semi-prep HPLC using 40-80% MeCN in Water (0.1% TFA, flow rate: 4.5 ml/min, 15 min run, 2 min wash).

Radioligand Binding Assay

The affinity for GHS-R1a was determined using a radioligand binding assay. Assays were performed using GHS-R1a transfected HEK293 cells as the receptor source and human [$^{125}$I-His$^9$]ghrelin(1-28) (PerkinElmer Inc.) as the radioligand. Human ghrelin (1-28) (purchased from Abcam) was used as a reference to ensure the validity of the results. Test peptides (at concentrations of 10$^{-5}$M, 10$^{-6}$M, 10$^{-7}$M, 10$^{-8}$M, 10$^{-9}$M, 10$^{-10}$M and 10$^{-11}$M) and [$^{125}$I-His$^9$]ghrelin (15 pM per assay tube) were mixed in binding buffer (25 mM HEPES, 5 mM magnesium chloride, 1 mM calcium chloride, 2.5 mM EDTA, and 0.4% BSA, pH 7.4). The HEK293 cells (50,000 cells per assay tube) was added to the assay tube containing test peptides and [$^{125}$I]-ghrelin. The resulting suspension was incubated for 20 min with shaking (550 rpm). Unbound [$^{125}$I]-ghrelin was washed off and the amount of [$^{125}$I-His$^9$]ghrelin bound to GHS-R1a was measured by a Gamma counter (cobra II auto gamma counter/Perkin Elmer). All binding assays were performed in triplicate.

REFERENCES

[1] Jeffery, P. L.; Herington, A. C.; Chopin, L. K., J Endocrinol 2002, 172 (3), R7-11.

[2] 1. Tovmassian, D.; Abdul Razak, M.; London, K, Int J Surg Oncol 2016, 2016, 6162182.

[3] Lu, C.; McFarland, M. S.; Nesbitt, R. L.; Williams, A. K.; Chan, S.; Gomez-Lemus, J.; Autran-Gomez, A. M.; Al-Zahrani, A.; Chin, J. L.; Izawa, J. I.; Luyt, L. G.; Lewis, J. D., Prostate 2012, 72 (8), 825-33.

[4] Douglas, G. A.; McGirr, R.; Charlton, C. L.; Kagan, D. B.; Hoffman, L. M.; Luyt, L. G.; Dhanvantari, S., Peptides 2014, 54, 81-8.

[5] Rudolph, J.; Esler, W. P.; O'Connor, S.; Coish, P. D.; Wickens, P. L.; Brands, M.; Bierer, D. E.; Bloomquist, B. T.; Bondar, G.; Chen, L.; Chuang, C. Y.; Claus, T. H.; Fathi, Z.; Fu, W.; Khire, U. R.; Kristie, J. A.; Liu, X. G.; Lowe, D. B.; McClure, A. C.; Michels, M.; Ortiz, A. A.; Ramsden, P. D.; Schoenleber, R. W.; Shelekhin, T. E.; Vakalopoulos, A.; Tang, W.; Wang, L.; Yi, L.; Gardell, S. J.; Livingston, J. N.; Sweet, L. J.; Bullock, W. H., J Med Chem 2007, 50 (21), 5202-16.

[6] Esler, W. P.; Rudolph, J.; Claus, T. H.; Tang, W.; Barucci, N.; Brown, S. E.; Bullock, W.; Daly, M.; Decarr, L.; Li, Y.; Milardo, L.; Molstad, D.; Zhu, J.; Gardell, S. J.; Livingston, J. N.; Sweet, L. J., Endocrinology 2007, 148 (11), 5175-85.

[7] Hanrahan, P.; Bell, J.; Bottomley, G.; Bradley, S.; Clarke, P.; Curtis, E.; Davis, S.; Dawson, G.; Horswill, J.; Keily, J.; Moore, G.; Rasamison, C.; Bloxham, J., Bioorg Med Chem Lett 2012, 22 (6), 2271-8.

[8] Potter, R.; Horti, A. G.; Ravert, H. T.; Holt, D. P.; Finley, P.; Scheffel, U.; Dannals, R. F.; Wahl, R. L., Bioorg Med Chem 2011, 19 (7), 2368-72.

[9] Vodnik, M.; Strukelj, B.; Lunder, M., *Horm Metab Res* 2016, 48 (1), 1-15.

[10] Nikolopoulos, D.; Theocharis, S.; Kouraklis, G., Regul Pept 2010, 163 (1-3), 7-17.

Through the embodiments that are illustrated and described, the currently contemplated best mode of making and using the invention is described. Without further elaboration, it is believed that one of ordinary skill in the art can, based on the description presented herein, utilize the present invention to the full extent. Alterations, modifications and variations can be effected to the particular embodiments by those skill in the art without departing from the scope of the disclosure, which is defined solely by the claims appended hereto.

What is claimed is:

1. A growth hormone (GH) secretagogue receptor (GHS-R1a) ligand, the GHS-R1a ligand being selected from:

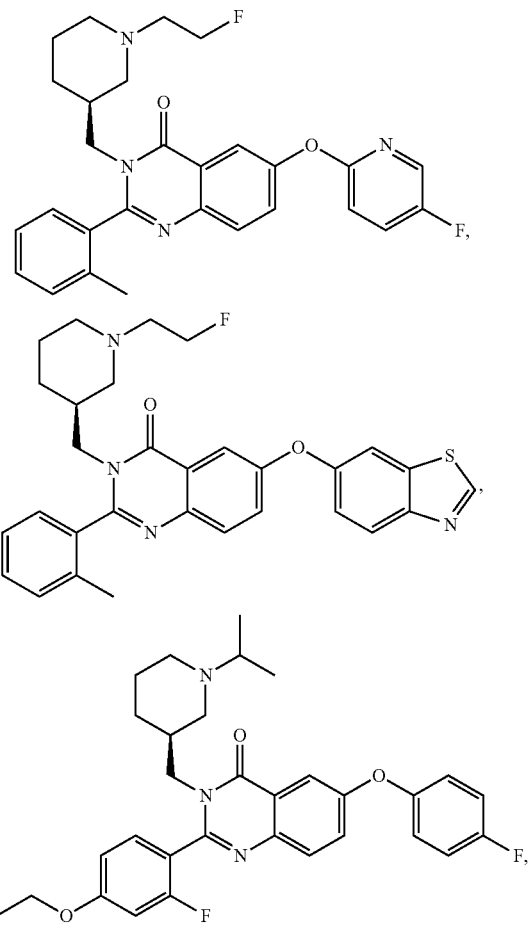

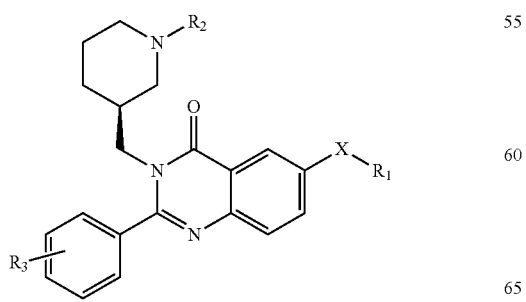

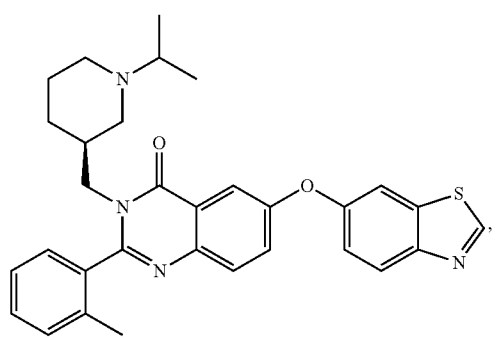

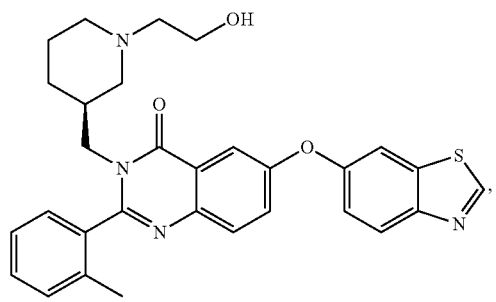

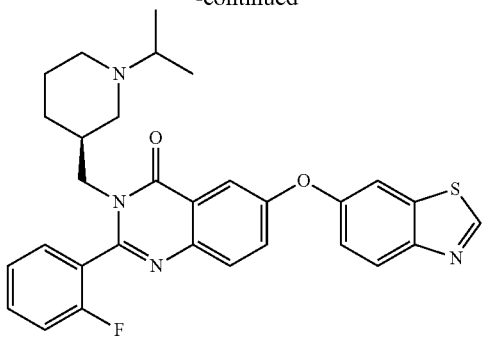

or a pharmaceutically acceptable salt thereof.

2. The GHS-R1a ligand of claim 1, wherein the GHS-R1a ligand includes a $^{18}$F detectable label.

3. The GHS-R1a ligand of claim 1, wherein the GHS-R1a ligand includes a detectable label, and wherein said detectable label includes $^{76}$Br, $^{123}$I, $^{125}$I, and $^{131}$I.

4. The GHS-R1a ligand of claim 1, wherein the GHS-R1a ligand is conjugated to other molecular entities or nanoparticles.

5. The GHS-R1a ligand of claim 1, wherein the GHS-R1a ligand is conjugated to or incorporated within a nanoparticle.

6. The GHS-R1a ligand of claim 5, wherein the nanoparticle is selected from a group comprising: gold nanoparticles, dendrimers, iron oxide particles, liposomes, protein nanoparticles, or other polymeric nanoparticles.

7. The GHS-R1a ligand of claim 1, wherein the GHS-R1a ligand is conjugated to a cytotoxic molecule.

8. The GHS-R1a ligand of claim 7, wherein the cytotoxic molecule is selected from a group comprising: anthracyclins, taxanes, nucleotide analogues, platinum complexes, and kinase inhibitors.

9. A method of detecting ghrelin receptors at a target site of a subject, the method comprising:
(a) providing the GHS-R1a ligand of claim 1 having a detectable label; (b) administering a concentration of the GHS-R1a ligand having the detectable label of step (a) to the subject effective to detect the growth hormone receptors at the target site; (c) allowing the GHS-R1a ligand having the detectable label to accumulate at the target site within the subject; and (d) detecting the GHS-R1a ligand having the detectable label at the target site thereby detecting the ghrelin receptors at the target site.

10. A method of assessing the malignancy of a tumor, the method comprising: (a) contacting the tumor with a GHS-R1a ligand of claim 1 having a detectable label, (b) detecting the expression of the GHS-R1a ligand having the detectable label in the tumor, (c) comparing the expression of step (b) with the expression of said GHS-R1ligand having the detectable label in a control tissue, and (d) assessing the malignancy of the tumor based on the comparison.

11. A method of imaging cancer cells, cardiac tissue or a ghrelin receptor, the method comprising (a) contacting the cancer cells, cardiac tissue or ghrelin receptor with a GHS-R1a ligand of claim 1 having a detectable label, and (b) detecting the expression of the GHS-R1a ligand having the detectable label in the cancer cells, cardiac tissue or ghrelin receptor.

12. A method of imaging, diagnosing or staging cancer, or heart disease, the method comprising (a) contacting the cancer cells, cardiac tissue or ghrelin receptor with a GHS-R1a ligand of claim 1 having a detectable label, (b) detecting the expression of the GHS-R1a ligand having the detectable label in the cancer cells, cardiac tissue or ghrelin receptor thereby imaging the cancer or heart disease, (c) comparing the expression of step (b) with the expression of said GHS-R1a ligand having the detectable label in a control tissue, and (d) diagnosing or staging said cancer or heart disease based on the comparison.

13. A pharmaceutical composition comprising a GHS-R1a ligand of claim 1, and a pharmaceutically acceptable carrier.

14. A method of increasing the level of endogenous growth hormone in a subject comprising administering to the subject a pharmaceutically effective amount of the pharmaceutical composition of claim 13.

15. A method for treating a subject of a GHS-R1a receptor related disorder, the method comprising administering to the subject a pharmaceutically effective amount of the pharmaceutical composition of claim 13.

16. The method of claim 15, wherein the disorder is selected from the group consisting of: GH deficiency, cachexia in patient with cancer or chronic obstructive pulmonary disease, obesity, GI motility, gastric emptying, ulcer or gastroparesis, anorexia nervosa, heart failure, diabetes mellitus or Type 1 and Type 2 diabetes mellitus complications, constipation and Parkinson's disease.

17. The GHS-R1a ligand of claim 1, wherein the GHS-R1a ligand has a cLogD below 2.8.

18. The GHS-R1a ligand of claim 1, wherein the GHS-R1a ligand has an $IC_{50}$ below 0.5 nM.

19. The GHS-R1a ligand of claim 1, wherein the GHS-R1a ligand has an IC50 below 1.8 nM and a cLogD below 2.8.

* * * * *